US010980860B2

(12) United States Patent
Vetter et al.

(10) Patent No.: US 10,980,860 B2
(45) Date of Patent: Apr. 20, 2021

(54) DIAGNOSIS, PREVENTION AND TREATMENT OF DISEASES OF THE JOINT

(71) Applicant: Ascendis Pharma A/S, Hellerup (DK)

(72) Inventors: Dirk Vetter, Heidelberg (DE); Ulrich Hersel, Heidelberg (DE); Kennett Sprogøe, Palo Alto, CA (US); Nora Kaluza, Heidelberg (DE); Oliver Keil, Berlin (DE); Guillaume Maitro, Mannheim (DE); Harald Rau, Dossenheim (DE)

(73) Assignee: Ascendis Pharma A/S, Hellerup (DK)

( * ) Notice: Subject to any disclaimer, the term of this patent is extended or adjusted under 35 U.S.C. 154(b) by 0 days.

(21) Appl. No.: 14/435,367

(22) PCT Filed: Oct. 8, 2013

(86) PCT No.: PCT/EP2013/070949
§ 371 (c)(1),
(2) Date: Apr. 13, 2015

(87) PCT Pub. No.: WO2014/056915
PCT Pub. Date: Apr. 17, 2014

(65) Prior Publication Data
US 2015/0290337 A1 Oct. 15, 2015

(30) Foreign Application Priority Data

Oct. 11, 2012 (EP) .................................. 12188227

(51) Int. Cl.
| | |
|---|---|
| A61K 47/50 | (2017.01) |
| A61K 47/56 | (2017.01) |
| A61K 47/60 | (2017.01) |
| A61K 47/69 | (2017.01) |
| A61K 38/20 | (2006.01) |
| A61K 38/00 | (2006.01) |
| A61K 39/395 | (2006.01) |
| A61P 19/02 | (2006.01) |
| A61K 9/00 | (2006.01) |
| C07K 14/545 | (2006.01) |

(52) U.S. Cl.
CPC ........ *A61K 38/2006* (2013.01); *A61K 9/0019* (2013.01); *A61K 38/00* (2013.01); *A61K 39/395* (2013.01); *A61K 47/50* (2017.08); *A61K 47/56* (2017.08); *A61K 47/60* (2017.08); *A61K 47/6903* (2017.08); *A61P 19/02* (2018.01); *C07K 14/545* (2013.01)

(58) Field of Classification Search
CPC ........ A61K 47/50; A61K 47/56; A61K 47/60; A61K 47/6903; A61K 38/00; A61K 39/395; A61P 19/02
See application file for complete search history.

(56) References Cited

U.S. PATENT DOCUMENTS

| | | | |
|---|---|---|---|
| 7,393,953 B2 | 7/2008 | Zhao et al. | |
| 7,585,837 B2 | 9/2009 | Shechter et al. | |
| 8,088,916 B2 * | 1/2012 | Ikeya ................. | A61K 47/4823 536/53 |
| 2006/0233855 A1 | 10/2006 | Seliktar et al. | |
| 2011/0097302 A1 | 4/2011 | Yuan et al. | |
| 2011/0112021 A1 | 5/2011 | Rau et al. | |
| 2012/0156259 A1 * | 6/2012 | Rau ...................... | A61K 9/0024 424/400 |
| 2012/0156260 A1 * | 6/2012 | Rau .................. | A61K 47/48215 424/400 |

FOREIGN PATENT DOCUMENTS

| | | | |
|---|---|---|---|
| CN | 102413843 | 4/2012 | |
| WO | WO 2001/47562 | 7/2001 | |
| WO | WO 2002/089789 | 11/2002 | |
| WO | WO 2005/099768 | 10/2005 | |
| WO | WO 2006/003014 | 1/2006 | |
| WO | WO 2006/136586 | 12/2006 | |
| WO | WO 2009/045539 | 4/2009 | |
| WO | WO 2009/095479 | 8/2009 | |
| WO | WO-2009095479 A2 * | 8/2009 | ....... A61K 47/48215 |
| WO | WO 2010/100220 | 9/2010 | |
| WO | WO 2011/012715 | 2/2011 | |
| WO | WO 2011/012721 | 2/2011 | |
| WO | WO 2011/012722 | 2/2011 | |
| WO | WO 2011/089214 | 7/2011 | |
| WO | WO 2011/089215 | 7/2011 | |
| WO | WO 2011/089216 | 7/2011 | |
| WO | WO 2012/125914 | * 9/2012 | |

OTHER PUBLICATIONS

Burrage et al., Front. Biosci., 2006, vol. 11:529-543.*
Chevalier et al., J. Rheumatol., 2005, vol. 32:1317-1323.*
Gossec et al., Ann. Rheum. Dis., 2004, vol. 63:478-482.*
International Search Reportissued in corresponding International Aprlication No. PCT/EP2013/070949 dated Dec. 12, 2013, 4 pages.
International Written Opinion issued in corresponding International Application No. PCT/EP2013/070949, dated Apr. 14, 2015.
International Preliminary Report on Patentability issued in corresponding International Application PCT/EP2013/070949 dated Apr. 14, 2015.
Xavier Chevalier et al., "Safety Study of Intraarticular Injection of Interleukin 1Receptor Antagonist in Patients with Painful Knee Osteoarthritis: A Multicenter Study", The Journal of Rheumatology, 2005, pp. 1317-1323, vol. 32, No. 7.
Pascal Richette et al., "A High Interleukin 1 Receptor Antagonist/ IL-1β Ratio Occurs Naturally in Knee Osteoarthritis", The Journal of Rheumatology, 2008, pp. 1650-1654, vol. 35, No. 8.

(Continued)

*Primary Examiner* — Xiaozhen Xie

(74) *Attorney, Agent, or Firm* — Haug Partners LLP

(57) ABSTRACT

The present invention relates to a polymeric prodrug for use in the treatment, prevention and/or diagnosis a disease of the joint and pharmaceutical compositions and medical devices comprising said polymeric prodrugs.

15 Claims, 1 Drawing Sheet

(56) References Cited

OTHER PUBLICATIONS

Rachel E. Whitmire et al., "Self-assembling nanoparficles for intra-articular delivery of anti-inflammatory proteins", Biomaterials, 2012, pp. 7665-7675. vol. 33, No. 30.
K.S. Kim, et al., "Injectable hyaluronic acid-tyramine hydrogels for the treatment of rheumatoid arthritis", Acta Biomaterialia, Elseviers, Amsterdam, NL, 2011, pp. 666-674, XP027577077, vol. 7, No. 2.
Xin-Ming Liu et al., "Syntheses of Click PEG-Dexamethasone Conjugates for the Treatment of Rheumatoid Arthritis", Biomacromolecules, 2010, pp. 2621-2628, XP055090588, vol. 11, No. 10.
Yu P. et al., "PEGylation of rhIL-IRA increased its solution stability at room temperature" Process Biochemistry, Elseviers, NL, pp. 1340-1345, XP026708839, vol. 44, No. 12, (2009).

\* cited by examiner

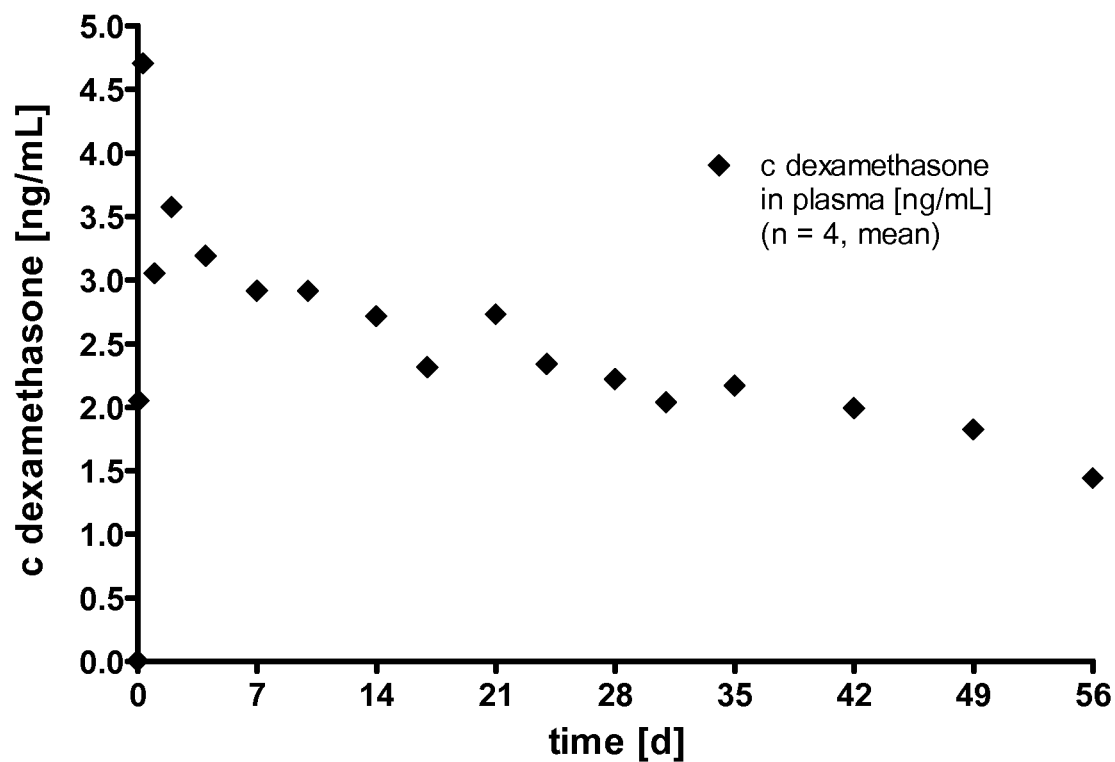

ND TREATMENT OF DISEASES OF THE JOINT

The present application claims priority from PCT Patent Application No. PCT/EP2013/070949 filed on Oct. 8, 2013, which claims priority from European Patent Application No. EP 12188227.8 filed on Oct. 11, 2012, the disclosures of which are incorporated herein by reference in their entirety.

Diseases of the joint pose a significant burden on the patient as mobility of legs or fingers may be significantly affected. A common disease of the joints is arthropathy of which one form is arthritis. More than 100 different forms of arthritis are known. The most common form is osteoarthritis, a degenerative joint disease, which may result from trauma to the joint, infection of the joint, or age. Other arthritis forms are rheumatoid arthritis, psoriatic arthritis, and related autoimmune diseases. Septic arthritis is caused by joint infection.

Patients of arthropathy suffer from joint pain which is often long lasting and may be localized to the affected joint(s). In the affected joint(s) the pain may occur due to inflammation that occurs around or inside the joint, damage to the joint from disease, daily wear and tear of joint, muscle strains caused by forceful movements against stiff, painful joints and fatigue.

In the US arthritis is the most common cause of disability and more than 20 million patients experience limitations in their everyday life. Absence from work and frequent physician visits of arthritis patients cause significant costs which is estimated to be close to $100 billion of which nearly 50% accounts from lost earnings.

Many forms of arthropathy cannot be cured and the exact treatment depends on the specific type of joint disease. Treatment includes physical therapy, lifestyle changes, orthopedic bracing, medications and occasionally joint replacement surgery. Medications can help reduce inflammation in the joint which decreases pain. Moreover, by decreasing inflammation, the joint damage may be slowed.

Arthropathy may be addressed by either systemic or local administration of suitable drugs or a combination of systemic and localized administration. Examples for systemic drugs used in the treatment of rheumatoid arthritis are etanercept (Enbrel) and infliximab (Remicade) or methotrexate.

An example for a localized treatment is the injection of cortisone into the affected joint. Localized administration of drugs to the joints is preferable for many reasons. Systemic side effects may be suppressed or entirely avoided and therapeutic concentrations at the affected site are much more readily achieved. Unfortunately though, the efflux of drugs injected into a joint is very high, and synovial clearance may result in wash out of the drug within a day from the joint region.

For instance it has been found that injection into the joint of IL-1ra was not significantly reducing the symptoms of osteoarthritis (Chevalier et al, J. Rheumatol 32 (2005) 1317-23), and the poor efficacy seen was related to the short half-life of IL-1ra in the synovium (Richette et al. J Rheumatol 35 (2008) 1650-4).

Consequently, the therapeutic efficacy is greatly reduced and repeated frequent administration is required which is posing a challenge as injections into the joints are cumbersome procedures both for the patient as well as for the health care professional performing the administration.

Various approaches have been tested to provide for long-lasting delivery of therapeutic agents in a localized manner to treat diseases of the joint such as depot formulations or gene therapy. However, significant setbacks have been experienced in testing such delivery systems. Obstacles remain in the administration of a small volume as the joint space available for intraarticular injection may hold only a ml of synovial fluid or less. For the same reason, both viscosity of the injectable and needle size must match the requirement of injection into the small space of a joint. Furthermore, efficient control of the time-action profile of a disease-modifying agent must be achieved.

In view of the above, there exists a need to provide a form of administration that overcomes these drawbacks at least partially.

This objective is achieved with a polymeric prodrug and/or a pharmaceutical composition comprising a polymeric prodrug for use in the prevention, diagnosis and/or treatment of a disease of the joint.

Preferred is the prevention and/or treatment of a disease of the joint.

The invention further relates to a polymeric prodrug and/or a pharmaceutical composition comprising a polymeric prodrug for use for intra-articular injection.

The invention also relates to a polymeric prodrug and/or a pharmaceutical composition comprising a polymeric prodrug for use for intra-articular injection in the prevention, diagnosis and/or treatment of a disease of the joint.

It was now surprisingly found that polymeric prodrugs provide a long-lasting depot which is beneficial for the prevention, diagnosis and/or treatment of a disease of the joint. Such polymeric prodrugs are carrier-linked prodrugs in which the carrier is a polymer and to which biologically active moieties are connected through reversible prodrug linkers and which biologically active moieties are released from the polymeric prodrug in the form of a drug.

The invention also relates to a method of preventing, diagnosing and/or treating a disease of the joint, wherein said method comprises the step of administering a therapeutically effective amount of a polymeric prodrug or pharmaceutical composition of the present invention to a patient in need thereof.

As the drug is released in therapeutically effective concentrations over an extended period of time, overconcentration of the drug is avoided.

Within the present invention the terms are used with the meaning as follows

As used herein, a "disease of the joint" is any disease, condition or illness affecting one or more joints of a mammal.

The term "intra-articular injection" refers to an injection into a joint. Types of joints for intra-articular administration are fibrous joints, cartilaginous joint and synovial joints. Anatomically, joints suitable for intraarticular administration according to the invention are articulations of the hand, elbow joints, wrist joints, axillary articulations, sternoclavicular joints, vertebral articulations, temporomandibular joints, sacroiliac joints, hip joints, knee joints, articulations of the foot.

Administration of the polymeric depot of the invention may be performed in a monoarticular or polyarticular fashion, i.e. injections may be performed on one or more than one joint.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "reagent" means a chemical compound which comprises at least one functional group for reaction with the functional group of another reagent or moiety.

As used herein, the term "backbone reagent" means a reagent, which is suitable as a starting material for forming hydrogels. As used herein, a backbone reagent preferably does not comprise biodegradable linkages. A backbone reagent may comprise a "branching core" which refers to an atom or moiety to which more than one other moiety is attached.

As used herein, the term "crosslinker reagent" means a linear or branched reagent, which is suitable as a starting material for crosslinking backbone reagents. Preferably, the crosslinker reagent is a linear chemical compound. A crosslinker reagent comprises at least two biodegradable linkages.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a biologically active moiety is released from a prodrug as a drug.

Accordingly, the phrase "in bound form" is used to refer to the corresponding moiety of a reagent, i.e. "lysine in bound form" refers to a lysine moiety which lacks one or more atom(s) of the lysine reagent and is part of a molecule.

As used herein, the term "functional group" means a group of atoms which can react with other functional groups. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxy (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine.

If a chemical functional group is coupled to another functional group, the resulting chemical structure is referred to as "linkage". For example, the reaction of an amine group with a carboxyl group results in an amide linkage.

As used herein, the term "activated functional group" means a functional group, which is connected to an activating group, i.e. a functional group was reacted with an activating reagent. Preferred activated functional groups include but are not limited to activated ester groups, activated carbamate groups, activated carbonate groups and activated thiocarbonate groups. Preferred activating groups are selected from formulas ((f-i) to (f-vi):

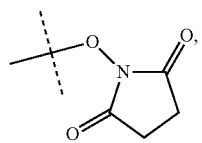
(f-i)

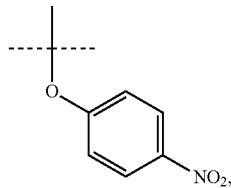
(f-ii)

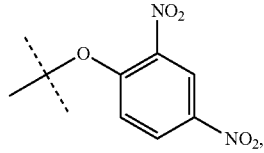
(f-iii)

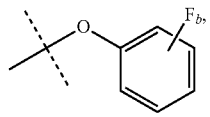
(f-iv)

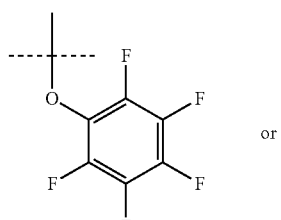
or
(f-v)

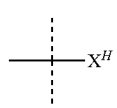
(f-vi)

wherein
the dashed lines indicate attachment to the rest of the molecule;
b is 1, 2, 3 or 4; and
$X^H$ is Cl, Br, I, or F.

Accordingly, a preferred activated ester has the formula

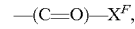

wherein
$X^F$ is selected from formula (f-i), (f-ii), (f-iii), (f-iv), (f-v) and (f-vi).

Accordingly, a preferred activated carbamate has the formula

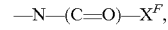

wherein
$X^F$ is selected from formula (f-i), (f-ii), (f-iii), (f-iv), (f-v) and (f-vi).

Accordingly, a preferred activated carbonate has the formula

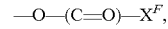

wherein
$X^F$ is selected from formula (f-i), (f-ii), (f-iii), (f-iv), (f-v) and (f-vi).

Accordingly, a preferred activated thioester has the formula

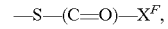

wherein
$X^F$ is selected from formula (f-i), (f-ii), (f-iii), (f-iv), (f-v) and (f-vi).

Accordingly, an "activated end functional group" is an activated functional group which is localized at the end of a moiety or molecule, i.e. is a terminal activated functional group.

As used herein, the term "capping group" means a moiety which is irreversibly, i.e. permanently, connected to a functional group to render it incapable of reacting with functional groups of other reagents or moieties.

As used herein, the term "protecting group" means a moiety which is reversibly connected to a functional group to render it incapable of reacting with, for example, another functional group. Suitable alcohol (—OH) protecting groups are, for example, acetyl, benzoyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, trityl, trimethylsilyl, tert-butyldimethylsilyl, tri-iso-propylsilyloxymethyl, triisopropylsilyl ether, methyl ether, and ethoxyethyl ether. Suitable amine protecting groups are, for example, carbobenzyloxy, p-methoxybenzyl carbonyl, tert-butyloxycarbonyl, 9-fluorenylmethyloxyarbonyl, acetyl, benzoyl, benzyl, carbamate, p-methoxybenzyl, 3,4-dimethoxybenzyl, p-methoxyphenyl, and tosyl. Suitable carbonyl protecting groups are, for example, acetals and ketals, acylals and dithianes. Suitable carboxylic acid protecting groups are, for example, methyl esters, benzyl esters, tert-butyl esters, 2,6-dimethylphenol, 2,6-diisopropylphenol, 2,6.-di-tert-butylphenol, silyl esters, orthoesters, and oxazoline. Suitable phosphate protecting groups are, for example, 2-cyanoethyl and methyl.

As used herein, the terms "work-up" and "working-up" refer to the series of manipulations required to isolate and purify the product(s) of a chemical reaction, in particular of a polymerization.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may for example also comprise functional groups or capping moieties. Preferably, a polymer has a molecular weight of at least 0.5 kDa, e.g. a molecular weight of at least 1 kDa, a molecular weight of at least 2 kDa, a molecular weight of at least 3 kDa or a molecular weight of at least 5 kDa.

As used herein, the term "polymeric" means a reagent or a moiety comprising one or more polymer(s).

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "polymerization" or "polymerizing" means the process of reacting monomer or macromonomer reagents in a chemical reaction to form polymer chains or networks, including but not limited to hydrogels.

As used herein, the term "macromonomer" means a molecule that was obtained from the polymerization of monomer reagents.

As used herein, the term "condensation polymerization" or "condensation reaction" means a chemical reaction, in which the functional groups of two reagents react to form one single molecule, i.e. the reaction product, and a low molecular weight molecule, for example water, is released.

As used herein, the term "suspension polymerization" means a heterogeneous and/or biphasic polymerization reaction, wherein the monomer reagents are dissolved in a first solvent, forming the disperse phase which is emulsified in a second solvent, forming the continuous phase. In the present invention, the monomer reagents are the at least one backbone reagent and the at least one crosslinker reagent. Both the first solvent and the monomer reagents are not soluble in the second solvent. Such emulsion is formed by stirring, shaking, exposure to ultrasound or Microsieve™ emulsification, more preferably by stirring or Microsieve™ emulsification and more preferably by stirring. This emulsion is stabilized by an appropriate emulsifier. The polymerization is initiated by addition of a base as initiator which is soluble in the first solvent. A suitable commonly known base suitable as initiator may be a tertiary base, such as tetramethylethylenediamine (TMEDA).

As used herein, the term "inert" refers to a moiety which is not chemically reactive, i.e. it does not react with other moieties or reagents. The person skilled in the art understands that the term "inert" does not per se exclude the presence of functional groups, but understands that the functional groups potentially present in an inert moiety are not reactive with functional groups of moieties/reagents brought in contact with the inert moiety in, for example, subsequent reactions. In particular, the inert moiety Z does not react with $A^{x0}$ or $A^{x2}$ or with functional groups present, for example, in reversible prodrug linker reagents, drugs, reversible prodrug linker moiety-biologically active moiety conjugate reagents or spacer reagents which may be covalently conjugated to the hydrogel of the present invention to obtain the hydrogel-linked prodrug of the present invention.

As used herein, the term "immiscible" means the property where two substances are not capable of combining to form a homogeneous mixture.

As used herein, the term "polyamine" means a reagent or moiety comprising more than one amine (—NH— and/or —NH$_2$), e.g. from 2 to 64 amines, from 4 to 48 amines, from 6 to 32 amines, from 8 to 24 amines, or from 10 to 16 amines. Particularly preferred polyamines comprise from 2 to 32 amines.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties especially selected from the following substituents and linkages:

$C_{1-50}$ alkyl, $C_{2-50}$ alkenyl, $C_{2-50}$ alkynyl, $C_{3-10}$ cycloalkyl, 4- to 7-membered heterocyclyl, 8- to 11-membered heterobicyclyl, phenyl; naphthyl; indenyl; indanyl; and tetralinyl; and linkages selected from the group comprising

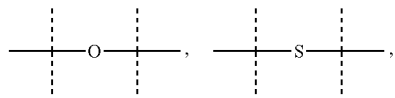

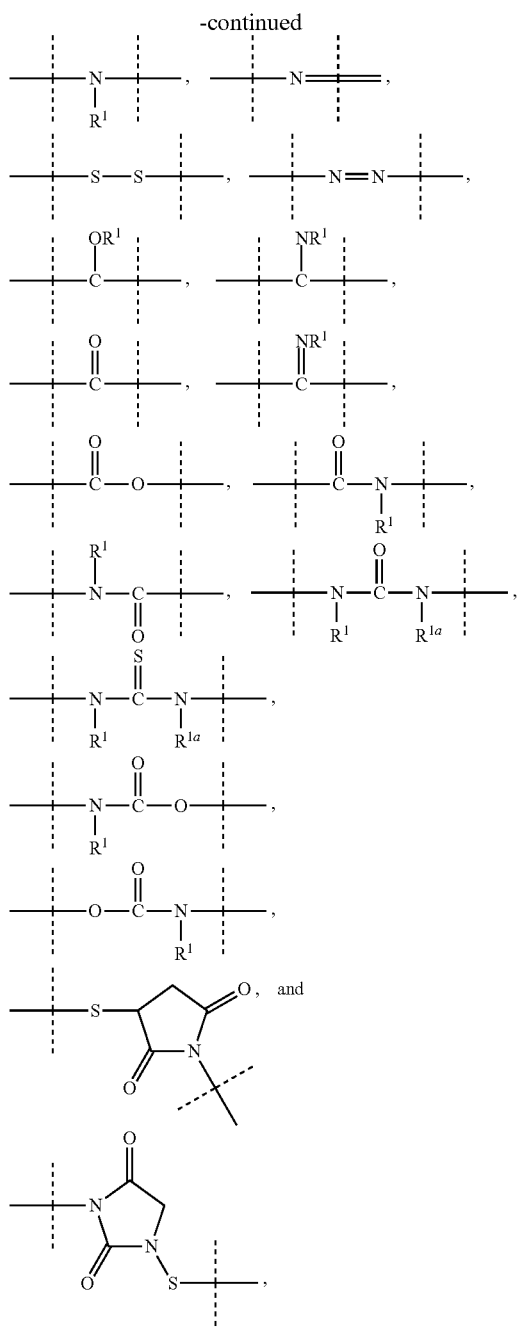

wherein
dashed lines indicate attachment to the remainder of the moiety or reagent, and
$R^1$ and $R^{1a}$ are independently of each other selected from H and $C_{1-6}$ alkyl.

The term "hyaluronic acid-based" as understood herein means that the mass proportion of hyaluronic acid chains in the hydrogel according to the invention is at least 10% by weight, preferably at least 20% by weight, and even more preferably at least 25% by weight based on the total weight of the hydrogel according to the invention. The remainder can be made up of other polymers.

As used herein, the term "$C_{1-4}$ alkyl" alone or in combination means a straight-chain or branched alkyl group having 1 to 4 carbon atoms. If present at the end of a molecule, examples of straight-chain and branched $C_{1-4}$ alkyl groups are methyl, ethyl, n-propyl, isopropyl, n-butyl, isobutyl, sec-butyl and tert-butyl. When two moieties of a molecule are linked by the $C_{1-4}$ alkyl group, then examples for such $C_{1-4}$ alkyl groups are —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, —$CH_2$—$CH_2$—$CH_2$—$CH_2$—, and —$CH_2$—$CH_2$—$CH_2(CH_3)$—. Each hydrogen atom of a $C_{1-4}$ alkyl group may be replaced by a substituent as defined below.

As used herein, the term "$C_{1-6}$ alkyl" alone or in combination means a straight-chain or branched alkyl group having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ alkyl group may be replaced by a substituent as defined below.

Accordingly, as used herein, the term "$C_{1-20}$ alkyl" alone or in combination means a straight-chain or branched alkyl group having 1 to 20 carbon atoms. The term "$C_{8-18}$ alkyl" alone or in combination means a straight-chain or branched alkyl group having 8 to 18 carbon atoms.

Accordingly, as used herein, the term "$C_{1-50}$ alkyl" alone or in combination means a straight-chain or branched alkyl group having 1 to 50 carbon atoms. Each hydrogen atom of a $C_{1-20}$ alkyl group, a $C_{8-18}$ alkyl group and $C_{1-50}$ alkyl group may be replaced by a substituent. In each case the alkyl group may be present at the end of a molecule or two moieties of a molecule may be linked by the alkyl group.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —$CH=CH_2$, —$CH=CH$—$CH_3$, —$CH_2$—$CH=CH_2$, —$CH=CHCH_2$—$CH_3$ and —$CH=CH$—$CH=CH_2$. When two moieties of a molecule are linked by the $C_{2-6}$ alkenyl group, then an example for such $C_{2-6}$ alkenyl is —$CH=CH$—. Each hydrogen atom of a $C_{2-6}$ alkenyl group may be replaced by a substituent as defined below. Optionally, one or more triple bond(s) may occur.

Accordingly, as used herein, the term "$C_{2-20}$ alkenyl" alone or in combination means a straight-chain or branched hydrocarbon residue comprising at least one carbon-carbon double bond having 2 to 20 carbon atoms. The term "$C_{2-50}$ alkenyl" alone or in combination means a straight-chain or branched hydrocarbon residue comprising at least one carbon-carbon double bond having 2 to 50 carbon atoms. If present at the end of a molecule, examples are —$CH=CH_2$, —$CH=CH$—$CH_3$, —$CH_2$—$CH=CH_2$, —$CH=CHCH_2$—$CH_3$ and —$CH=CH$—$CH=CH_2$. When two moieties of a molecule are linked by the alkenyl group, then an example is e.g. —$CH=CH$—. Each hydrogen atom of a $C_{2-20}$ alkenyl or $C_{2-50}$ alkenyl group may be replaced by a substituent as defined below. Optionally, one or more triple bond(s) may occur.

As used herein, the term "$C_{2-6}$ alkynyl" alone or in combination means straight-chain or branched hydrocarbon residue comprising at least one carbon-carbon triple bond having 2 to 6 carbon atoms. If present at the end of a molecule, examples are —$C\equiv CH$, —$CH_2$—$C\equiv CH$, $CH_2$—

$CH_2$—C≡CH and $CH_2$—C≡C—$CH_3$. When two moieties of a molecule are linked by the alkynyl group, then an example is: —C≡C—. Each hydrogen atom of a $C_{2-6}$ alkynyl group may be replaced by a substituent as defined below. Optionally, one or more double bond(s) may occur.

Accordingly, as used herein, the term "$C_{2-20}$ alkynyl" alone or in combination means a straight-chain or branched hydrocarbon residue comprising at least one carbon-carbon triple bond having 2 to 20 carbon atoms and "$C_{2-50}$ alkynyl" alone or in combination means a straight-chain or branched hydrocarbon residue comprising at least one carbon-carbon triple bond having 2 to 50 carbon atoms. If present at the end of a molecule, examples are —C≡CH, —$CH_2$—C≡CH, $CH_2$—$CH_2$—C≡CH and $CH_2$—C≡C—$CH_3$. When two moieties of a molecule are linked by the alkynyl group, then an example is —C≡C—. Each hydrogen atom of a $C_{2-20}$ alkynyl or $C_{2-50}$ alkynyl group may be replaced by a substituent as defined below. Optionally, one or more double bond(s) may occur.

As used herein, the terms "$C_{3-8}$ cycloalkyl" or "$C_{3-8}$ cycloalkyl ring" means a cyclic alkyl chain having 3 to 8 carbon atoms, which may be saturated or unsaturated, e.g. cyclopropyl, cyclobutyl, cyclopentyl, cyclohexyl, cyclohexenyl, cycloheptyl, cyclooctyl. Each hydrogen atom of a cycloalkyl carbon may be replaced by a substituent as defined below. The term "$C_{3-8}$ cycloalkyl" or "$C_{3-8}$ cycloalkyl ring" also includes bridged bicycles like norbornane or norbornene. Accordingly, "$C_{3-5}$ cycloalkyl" means a cycloalkyl having 3 to 5 carbon atoms and $C_{3-10}$ cycloalkyl having 3 to 10 carbon atoms.

Accordingly, as used herein, the term "$C_{3-10}$ cycloalkyl" means a carbocyclic ring system having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

As used herein, the term "halogen" means fluoro, chloro, bromo or iodo. Particularly preferred is fluoro or chloro.

As used herein, the term "4- to 7-membered heterocyclyl" or "4- to 7-membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 4- to 7-membered heterocycles include but are not limited to azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 4- to 7-membered heterocyclyl or 4- to 7-membered heterocyclic group may be replaced by a substituent as defined below.

As used herein, the term "8- to 11-membered heterobicyclyl" or "8- to 11-membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

The term "substituted" means that one or more —H atom(s) of a molecule or moiety are replaced by a different atom or a group of atoms, which are referred to as "substituent". Suitable substituents are selected from the group consisting of halogen; CN; COOR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more R$^{10}$, which are the same or different and wherein $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

wherein

R$^9$, R$^{9a}$, R$^{9b}$ are independently selected from the group consisting of H; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more R$^{10}$, which are the same or different and wherein $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N(R$^{11}$)—, —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; $C_{3-10}$ cycloalkyl; 4 to 7 membered heterocyclyl; or 8- to 11-membered heterobicyclyl, wherein T is optionally substituted with one or more R$^{10}$, which are the same or different;

R$^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N(R$^{12a}$R$^{12b}$); OC(O)N(R$^{12}$R$^{12a}$);

or $C_{1-6}$ alkyl, wherein $C_{1-6}$ alkyl is optionally substituted with one or more halogen, which are the same or different;

$R^{11}, R^{11a}, R^{12}, R^{12a}, R^{12b}$ are independently selected from the group consisting of H; or $C_{1-6}$ alkyl, wherein $C_{1-6}$ alkyl is optionally substituted with one or more halogen, which are the same or different.

In one embodiment $R^9$, $R^{9a}$, $R^{9b}$ may be independently of each other H.

In one embodiment $R^{10}$ is $C_{1-6}$ alkyl.

In one embodiment T is phenyl.

Preferably, a maximum of 6-H atoms of a molecule are independently replaced by a substituent, e.g. 5-H atoms are independently replaced by a substituent, 4-H atoms are independently replaced by a substituent, 3-H atoms are independently replaced by a substituent, 2-H atoms are independently replaced by a substituent, or 1-H atom is replaced by a substituent.

As used herein, the term "interrupted" means that between two carbon atoms or at the end of a carbon chain between the respective carbon atom and the hydrogen atom one or more atom(s) are inserted.

As used herein, the term "prodrug" means a compound that undergoes biotransformation before exhibiting its pharmacological effects. Prodrugs can thus be viewed as biologically active moieties connected to specialized non-toxic protective groups used in a transient manner to alter or to eliminate undesirable properties in the parent molecule, i.e. in a prodrug a biologically active moiety is conjugated through a reversible linkage to a specialized group. This also includes the enhancement of desirable properties in the drug and the suppression of undesirable properties.

As used herein, the term "carrier-linked prodrug" means a prodrug that contains a temporary linkage of a biologically active moiety with a transient carrier group that produces improved physicochemical or pharmacokinetic properties and that can be easily removed in vivo, usually by a hydrolytic cleavage, i.e. in a carrier-linked prodrug a biologically active moiety is conjugated through a reversible linkage to a carrier moiety and which carrier moiety produces improved physicochemical or pharmacokinetic properties. Upon cleavage of the reversible linkage the biologically active moiety is released as the corresponding drug.

Accordingly, a "polymeric prodrug" is a carrier-linked prodrug in which the carrier is polymeric.

As used herein, the term "promoiety" means the part of the prodrug which is not the drug, thus linker and carrier and/or any optional spacer moieties.

As used herein, the term "reversible prodrug linker moiety" means a moiety which on its one end is attached to a biologically active moiety D through a reversible linkage and on another end is attached through a permanent linkage, which in the present invention is formed by the reaction of an amine functional group of a backbone moiety or $A^{x2}$ with $A^{y1}$, thereby linking the biologically active moiety to the hydrogel carrier in the carrier-linked prodrugs of the present invention. A "reversible linkage" is a linkage that is non-enzymatically hydrolytically degradable, i.e. cleavable, under physiological conditions (aqueous buffer at pH 7.4, 37° C.) with a half-life ranging from one hour to twelve months.

In contrast, a "permanent linkage" or "stable linkage" is non-enzymatically hydrolytically degradable under physiological conditions (aqueous buffer at pH 7.4, 37° C.) with half-lives of more than twelve months.

A "biodegradably linkage" is a linkage that is enzymatically and/or non-enzymatically hydrolytically degradable, i.e. cleavable, under physiological conditions (aqueous buffer at pH 7.4, 37° C.) with a half-life ranging from one hour to twelve months. Preferably, also a biodegradable linkage is non-enzymatically hydrolytically degradable under physiological conditions.

As used herein, the term "traceless prodrug linker" means a reversible prodrug linker which upon cleavage releases the drug in its free form. As used herein, the term "free form" of a drug means the drug in its unmodified, pharmacologically active form.

As used herein, the term "peptide" means a short polymer of amino acid monomers linked by peptide bonds. The term "polypeptide" means a peptide comprising up to and including 50 amino acid monomers. The term "protein" means a peptide of more than 50 amino acid monomers.

As used herein, the term "oligonucleotide" means a short nucleic acid polymer of up to 100 bases.

As used herein, the term "pharmaceutical composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the carrier-linked prodrug of the present invention and one or more pharmaceutically acceptable excipient(s).

As used herein, the term "excipient" refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the drug or biologically active moiety, together with a suitable amount of excipient so as to provide the form for proper administration to the patient. The formulation should suit the mode of administration.

The term "pharmaceutically acceptable" means approved by a regulatory agency such as the EMEA (Europe) and/or the FDA (US) and/or any other national regulatory agency for use in animals, preferably in humans.

In general the term "comprise" or "comprising" also encompasses "consist of" or "consisting of".

This invention relates to a polymeric prodrug and/or a pharmaceutical composition comprising a polymeric prodrug for use in the prevention, diagnosis and/or treatment of a disease of the joint.

The invention further relates to a polymeric prodrug and/or a pharmaceutical composition comprising a polymeric prodrug for use for intra-articular injection.

The invention also relates to a polymeric prodrug and/or a pharmaceutical composition comprising a polymeric prodrug for use for intra-articular injection in the prevention, diagnosis and/or treatment of a disease of the joint.

Preferably, this invention relates to a polymeric prodrug
(i) wherein the polymeric prodrug comprises a polymeric carrier comprising at least one polymer, and
(ii) wherein one or more biologically active moieties are reversibly connected through reversible prodrug linker moieties to said polymeric carrier.

In a preferred embodiment, the present invention relates to a polymeric prodrug or a pharmaceutical comprising a polymeric prodrug of the present invention, for use in the prevention, diagnosis and/or treatment of a disease of the joint,
(i) wherein the polymeric prodrug comprises a polymeric carrier comprising at least one polymer, and
(ii) wherein one or more biologically active moieties are reversibly connected through reversible prodrug linker moieties to said polymeric carrier.

The polymeric prodrug or pharmaceutical composition comprising one or more polymeric prodrugs for use in the prevention, diagnosis and/or treatment of a disease of the joint preferably is injectable into a joint.

Thus, in a preferred embodiment, the present invention relates to a polymeric prodrug or pharmaceutical composition of the present invention, for use for injection into a joint.

The polymeric prodrug comprises a polymeric carrier which carrier comprises at least one polymer and to which polymeric carrier one or more biologically active moieties are reversibly connected through reversible prodrug linker moieties, and which biologically active moieties are released from said polymeric prodrug as drugs upon intra-articular administration, i.e. administration into a joint.

The polymeric carrier comprises, preferably consist of at least one polymer which is more preferably selected from the group of polypeptides, poly(acrylic acids), poly(acrylates), poly(acrylamides), poly(alkyloxy) polymers, poly(amides), poly(amidoamines), poly(amino acids), poly(anhydrides), poly(aspartamide), poly(butyric acid), poly(caprolacton), poly(carbonates), poly(cyanoacrylates), poly(dimethylacrylamide), poly(esters), poly(ethylene), poly(ethylene glycol), poly(ethylene oxide), poly(ethyloxazoline), poly(glycolic acid), poly(hydroxyethyl acrylate), poly(hydroxyethyloxazoline), poly(hydroxypropylmethacrylamide), poly(hydroxypropyl methacrylate), poly(hydroxypropyloxazoline), poly(iminocarbonates), poly(N-isopropylacrylamide), poly(lactic acid), poly(lactic-co-glycolic acid), poly(methacrylamide), poly(methacrylates), poly(methyloxazoline), poly(propylene fumarate), poly(organophosphazenes), poly(ortho esters), poly(oxazolines), poly(propylene glycol), poly(siloxanes), poly(urethanes), poly(vinylalcohols), poly(vinylamines), poly(vinylmethylether), poly(vinylpyrrolidone), silicones, ribonucleic acids, desoxynucleic acid, albumins, antibodies and fragments thereof, blood plasma protein, collagens, elastin, fascin, fibrin, keratins, polyaspartate, polyglutamate, prolamins, transferrins, cytochromes, flavoprotein, glycoproteins, hemoproteins, lipoproteins, metalloproteins, phytochromes, phosphoproteins, opsins, agar, agarose, alginate, arabinans, arabinogalactans, carrageenan, cellulose, carbomethyl cellulose, hydroxypropyl methylcellulose and other carbohydrate-based polymers, chitosan, dextran, dextrin, gelatin, hyaluronic acid and derivatives, mannan, pectins, rhamnogalacturonans, starch, hydroxyalkyl starch, xylan, and copolymers and functionalized derivatives thereof.

In one embodiment the polymeric carrier is a soluble polymeric carrier. In this embodiment it is preferred that the soluble polymeric carrier comprises, preferably consists of, a linear, branched or dendrimeric PEG-based chain.

In another embodiment the polymeric carrier is a water-insoluble polymeric carrier. In this embodiment it is preferred that the water-insoluble polymeric carrier comprises, preferably consists of, a hydrogel, more preferably a hyaluronic acid-based hydrogel or a PEG-based hydrogel. Most preferably, the water-insoluble polymeric carrier is a PEG-based hydrogel.

The hydrogel is a shaped article, preferably in the shape of microparticles. More preferably, the hydrogel is in the shape of microparticulate beads. Even more preferably, such microparticulate beads have a diameter of 1 to 1000 μm, more preferably of 5 to 500 μm, more preferably of 10 to 100 μm, even more preferably of 20 to 80 μm. Equally preferred are microparticulate beads with a diameter of 10 to 250 μm, more preferably of 10 to 200 μm, even more preferably of 30 to 190 μm and most preferably of 50 to 180 μm. Bead diameters are measured when the microparticulate beads are suspended in an isotonic aqueous buffer.

Such hydrogel may be polymerized in different ways, such as through radical polymerization, ionic polymerization or ligation reactions. Preferred hydrogels, hydrogel-linked prodrugs and their methods of polymerization are disclosed in WO-A 2006/003014 and WO-A 2011/012715, which are hereby enclosed by reference in their entirety.

In a particularly preferred embodiment, the carrier of the polymeric prodrug is a hydrogel obtainable by a process comprising the steps of:
(a) providing a mixture comprising
   (a-i) at least one backbone reagent, wherein the at least one backbone reagent has a molecular weight ranging from 1 to 100 kDa, and comprises at least three amines (—NH$_2$ and/or —NH—);
   (a-ii) at least one crosslinker reagent, wherein the at least one crosslinker reagent has a molecular weight ranging from 0.5 kDa to 40 kDa or ranging from 0.5 kDa to 15 kDa, preferably from 1 kDa to 40 kDa or from 1 kDa to 10 kDa, even more preferably from 2 to 40 kDa or from 2 kDa to 5 kDa, even more preferably from 6 to 40 kDa, the at least one crosslinker reagent comprising
      (i) at least two carbonyloxy groups (—(C=O)—O— or —O—(C=O)—), and additionally
      (ii) at least two activated functional end groups selected from the group consisting of activated ester groups, activated carbamate groups, activated carbonate groups and activated thiocarbonate groups, and being PEG-based comprising at least 70% PEG; and (a-iii) a first solvent and at least a second solvent, which second solvent is immiscible in the first solvent, in a weight ratio of the at least one backbone reagent to the at least one crosslinker reagent ranging from 1:99 to 99:1;

(b) polymerizing the mixture of step (a) in a suspension polymerization to a hydrogel; and (c) optionally working-up the hydrogel.

The mixture of step (a) comprises a first solvent and at least a second solvent. Said first solvent is preferably selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof.

The at least one backbone reagent and at least one crosslinker reagent are dissolved in the first solvent, i.e. the disperse phase of the suspension polymerization. In one embodiment the backbone reagent and the crosslinker reagent are dissolved separately, i.e. in different containers, using either the same or different solvent and preferably using the same solvent for both reagents. In another embodiment, the backbone reagent and the crosslinker reagent are dissolved together, i.e. in the same container and using the same solvent.

A suitable solvent for the backbone reagent is an organic solvent. Preferably, the solvent is selected from the group consisting of dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof. More preferably, the backbone reagent is dissolved in a solvent selected from the group comprising acetonitrile, dimethyl sulfoxide, methanol or mixtures thereof. Most preferably, the backbone reagent is dissolved in dimethylsulfoxide.

In one embodiment the backbone reagent is dissolved in the solvent in a concentration ranging from 1 to 300 mg/ml, more preferably from 5 to 60 mg/ml and most preferably from 10 to 40 mg/ml.

A suitable solvent for the crosslinker reagent is an organic solvent. Preferably, the solvent is selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol, water or mixtures thereof. More preferably, the crosslinker reagent is dissolved in a solvent selected from the group comprising dimethylformamide, acetonitrile, dimethyl sulfoxide, methanol or mixtures thereof. Most preferably, the crosslinker reagent is dissolved in dimethylsulfoxide.

In one embodiment the crosslinker reagent is dissolved in the solvent in a concentration ranging from 5 to 500 mg/ml, more preferably from 25 to 300 mg/ml and most preferably from 50 to 200 mg/ml.

The at least one backbone reagent and the at least one crosslinker reagent are mixed in a weight ratio ranging from 1:99 to 99:1, e.g. in a ratio ranging from 2:98 to 90:10, in a weight ratio ranging from 3:97 to 88:12, in a weight ratio ranging from 3:96 to 85:15, in a weight ratio ranging from 2:98 to 90:10 and in a weight ratio ranging from 5:95 to 80:20; particularly preferred in a weight ratio from 5:95 to 80:20, wherein the first number refers to the backbone reagent and the second number to the crosslinker reagent.

Preferably, the ratios are selected such that the mixture of step (a) comprises a molar excess of amine groups from the backbone reagent compared to the activated functional end groups of the crosslinker reagent. Consequently, the hydrogel resulting from the process of the present invention has free amine groups which can be used to couple a prodrug linker reagent to the hydrogel, either directly or through a spacer moiety.

The at least one second solvent, i.e. the continuous phase of the suspension polymerization, is preferably an organic solvent, more preferably an organic solvent selected from the group comprising linear, branched or cyclic $C_{5-30}$ alkanes; linear, branched or cyclic $C_{5-30}$ alkenes; linear, branched or cyclic $C_{5-30}$ alkynes; linear or cyclic poly (dimethylsiloxanes); aromatic $C_{6-20}$ hydrocarbons; and mixtures thereof. Even more preferably, the at least second solvent is selected from the group comprising linear, branched or cyclic $C_{5-16}$ alkanes; toluene; xylene; mesitylene; hexamethyldisiloxane; or mixtures thereof. Most preferably, the at least second solvent selected from the group comprising linear $C_{7-11}$ alkanes, such as heptane, octane, nonane, decane and undecane.

Preferably, the mixture of step (a) further comprises a detergent. Preferred detergents are Cithrol DPHS, Hypermer 70A, Hypermer B246, Hypermer 1599A, Hypermer 2296, and Hypermer 1083.

Preferably, the detergent has a concentration of 0.1 g to 100 g per 1 L total mixture, i.e. disperse phase and continuos phase together. More preferably, the detergent has a concentration of 0.5 g to 10 g per 1 L total mixture, and most preferably, the detergent has a concentration of 0.5 g to 5 g per 1 L total mixture.

Preferably, the mixture of step (a) is an emulsion.

The polymerization in step (b) is initiated by adding a base. Preferably, the base is a non-nucleophilic base soluble in alkanes, more preferably the base is selected from N,N,N',N'-tetramethylethylene diamine (TMEDA), 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, triethylamine, DIPEA, trimethylamine, N,N-dimethylethylamine, N,N,N',N'-tetramethyl-1,6-hexanediamine, N,N,N',N'',N''-pentamethyldiethylenetriamine, 1,8-diazabicyclo[5.4.0]undec-7-ene, 1,5-diazabicyclo[4.3.0]non-5-ene, and hexamethylenetetramine. Even more preferably, the base is selected from TMEDA, 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, 1,8-diazabicyclo[5.4.0]undec-7-ene, 1,5-diazabicyclo[4.3.0]non-5-ene, and hexamethylenetetramine. Most preferably, the base is TMEDA.

The base is added to the mixture of step (a) in an amount of 1 to 500 equivalents per activated functional end group in the mixture, preferably in an amount of 5 to 50 equivalents, more preferably in an amount of 5 to 25 equivalents and most preferably in an amount of 10 equivalents.

In process step (b), the polymerization of the hydrogel of the present invention is a condensation reaction, which preferably occurs under continuous stirring of the mixture of step (a). Preferably, the tip speed (tip speed=π×stirrer rotational speed×stirrer diameter) ranges from 0.2 to 10 meter per second (m/s), more preferably from 0.5 to 4 m/s and most preferably from 1 to 2 m/s.

In a preferred embodiment of step (b), the polymerization reaction is carried out in a cylindrical vessel equipped with baffles. The diameter to height ratio of the vessel may range from 4:1 to 1:2, more preferably the diameter to height ratio of the vessel ranges from 2:1 to 1:1.

Preferably, the reaction vessel is equipped with an axial flow stirrer selected from the group comprising pitched blade stirrer, marine type propeller, or Lightnin A-310. More preferably, the stirrer is a pitched blade stirrer.

Step (b) can be performed in a broad temperature range, preferably at a temperature from −10° C. to 100° C., more preferably at a temperature of 0° C. to 80° C., even more preferably at a temperature of 10° C. to 50° C. and most preferably at ambient temperature. "Ambient temperature" refers to the temperature present in a typical laboratory environment and preferably means a temperature ranging from 17 to 25° C.

Preferably, the hydrogel obtained from the polymerization is a shaped article, such as a coating, mesh, stent, nanoparticle or a microparticle. More preferably, the hydrogel is in the form of microparticular beads having a diameter from 1 to 500 micrometer, more preferably with a diameter from 10 to 300 micrometer, even more preferably with a diameter from 20 and 150 micrometer and most preferably with a diameter from 30 to 130 micrometer. The afore-mentioned diameters are measured when the hydrogel microparticles are fully hydrated in water.

Optional step (c) comprises one or more of the following step(s):
(c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c6) drying the hydrogel,
(c7) transferring the hydrogel into a specific solvent suitable for sterilization, and
(c8) sterilizing the hydrogel, preferably by gamma radiation Preferably, optional step (c) comprises all of the following steps
(c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c7) transferring the hydrogel into a specific solvent suitable for sterilization, and
(c8) sterilizing the hydrogel, preferably by gamma radiation.

The at least one backbone reagent has a molecular weight ranging from 1 to 100 kDa, preferably from 2 to 50 kDa, more preferably from 5 and 30 kDa, even more preferably from 5 to 25 kDa and most preferably from 5 to 15 kDa.

Preferably, the backbone reagent is PEG-based comprising at least 10% PEG, more preferably comprising at least 20% PEG, even more preferably comprising at least 30% PEG and most preferably comprising at least 40% PEG.

In one embodiment the backbone reagent is present in the form of its acidic salt, preferably in the form of an acid addition salt. Suitable acid addition salts are formed from acids which form non-toxic salts. Examples include but are not limited to the acetate, aspartate, benzoate, besylate, bicarbonate, carbonate, bisulphate, sulphate, borate, camsylate, citrate, edisylate, esylate, formate, fumarate, gluceptate, gluconate, glucuronate, hexafluorophosphate, hibenzate, hydrochloride, hydrobromide, hydroiodide, isethionate, lactate, malate, maleate, malonate, mesylate, methylsulphate, naphthylate, nicotinate, nitrate, orotate, oxalate, palmitate, pamoate, phosphate, hydrogen phosphate, dihydrogen phosphate, sacharate, stearate, succinate, tartrate and tosylate. Particularly preferred, the backbone reagent is present in the form of its hydrochloride salt.

In one embodiment, the at least one backbone reagent is selected from the group consisting of a compound of formula (a-I)

$$B(-(A^0)_{x1}-(SP)_{x2}-A^1-P-A^2-Hyp^1)_x \qquad \text{(a-I)},$$

wherein

B is a branching core,

SP is a spacer moiety selected from the group consisting of $C_{1-6}$ alkyl, $C_{2-6}$ alkenyl and $C_{2-6}$ alkynyl, P is a PEG-based polymeric chain comprising at least 80% PEG, preferably at least 85% PEG, more preferably at least 90% PEG and most preferably at least 95% PEG, $Hyp^1$ is a moiety comprising an amine ($-NH_2$ and/or $-NH-$) or a polyamine comprising at least two amines ($-NH_2$ and/or $-NH-$), x is an integer from 3 to 16, x1, x2 are independently of each other 0 or 1, provided that x1 is 0, if x2 is 0, $A^0$, $A^1$, $A^2$ are independently of each other selected from the group consisting of

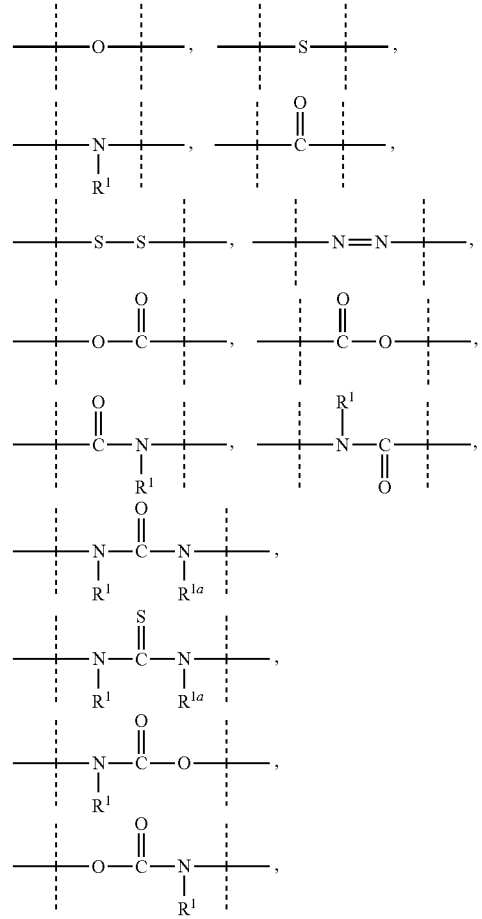

-continued

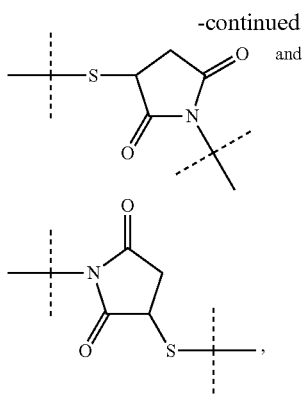

wherein $R^1$ and $R^{1a}$ are independently of each other selected from H and $C_{1-6}$ alkyl;

a compound of formula (a-II)

$$Hyp^2\text{-}A^3\text{-}P\text{-}A^4\text{-}Hyp^3 \qquad \text{(a-II)},$$

wherein

P is defined as above in the compound of formula (a-I), $Hyp^2$, $Hyp^3$ are independently of each other a polyamine comprising at least two amines ($-NH_2$ and/or $-NH-$), and $A^3$ and $A^4$ are independently selected from the group consisting of

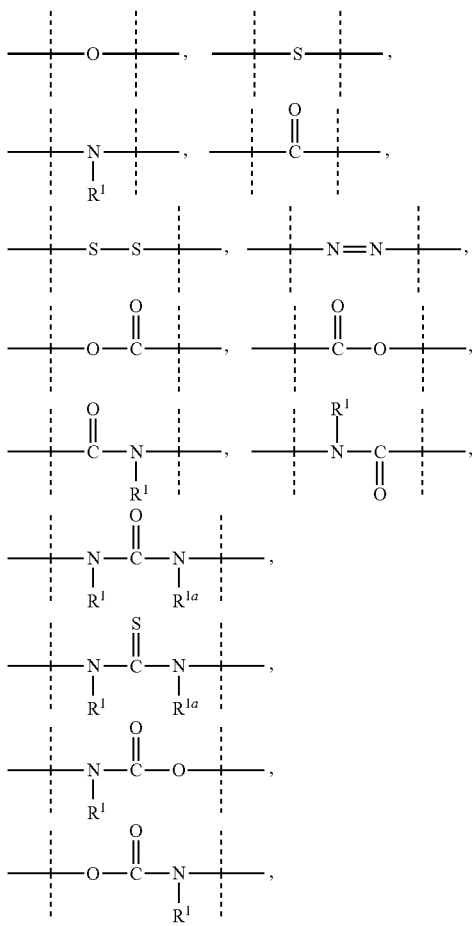

-continued

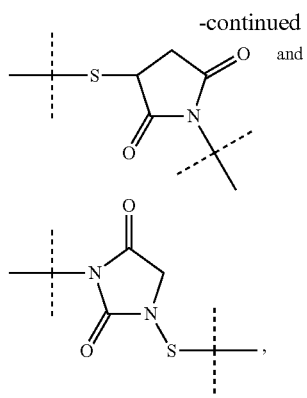

wherein $R^1$ and $R^{1a}$ are independently of each other selected from H and $C_{1-6}$ alkyl;

a compound of formula (a-III)

$$P^1\text{-}A^5\text{-}Hyp^4 \qquad \text{(a-III)},$$

wherein $P^1$ is a PEG-based polymeric chain comprising at least 80% PEG, preferably at least 85% PEG, more preferably at least 90% PEG and most preferably at least 95% PEG, $Hyp^4$ is a polyamine comprising at least three amines ($-NH_2$ and/or $-NH-$), and $A^5$ is selected from the group consisting of

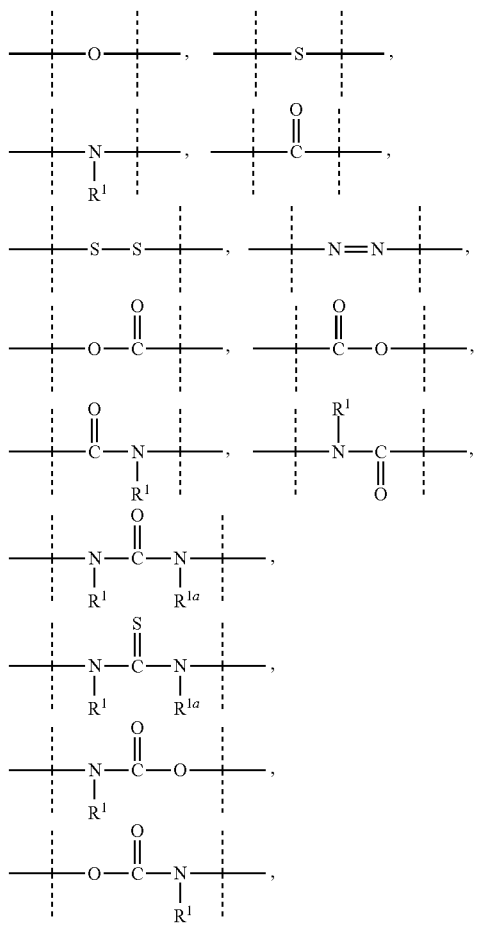

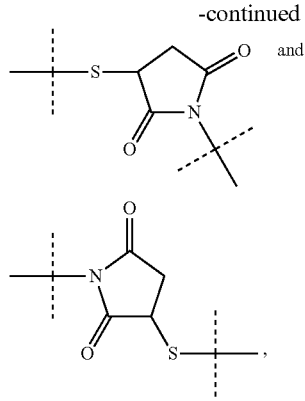

wherein R¹ and R¹ᵃ are independently of each other selected from H and $C_{1-6}$ alkyl;
and
a compound of formula (a-IV), $$T^1\text{-}A^6\text{-}Hyp^5 \qquad (a\text{-}IV),$$

wherein $Hyp^5$ is a polyamine comprising at least three amines (—NH₂ and/or —NH—), and $A^6$ is selected from the group consisting of

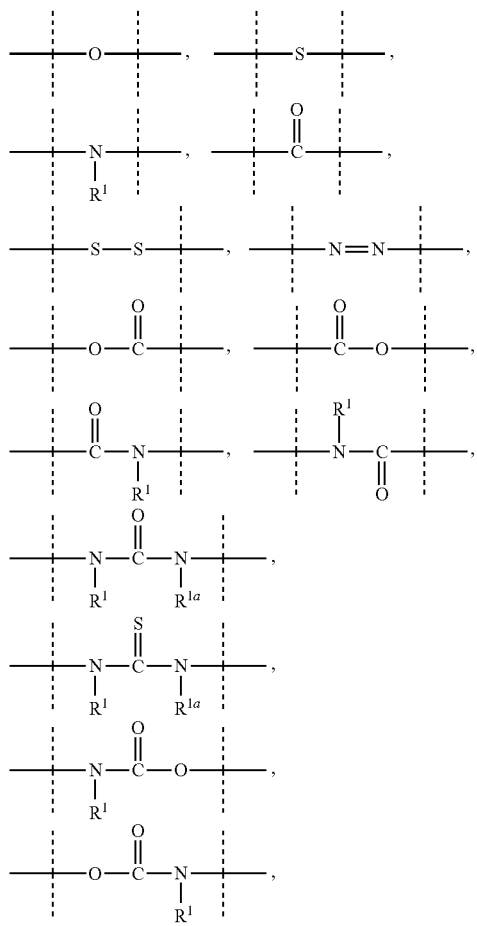

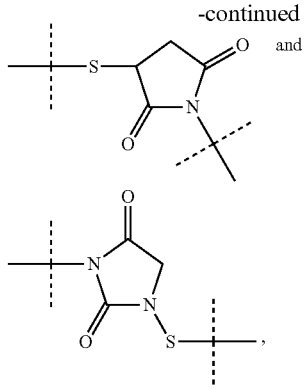

wherein R¹ and R¹ᵃ are independently of each other selected from H and $C_{1-6}$ alkyl; and $T^1$ is selected from the group consisting of $C_{1-50}$ alkyl, $C_{2-50}$ alkenyl or $C_{2-50}$ alkynyl, which fragment is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)₂—, 4- to 7-membered heterocyclyl, phenyl or naphthyl.

In the following sections the term "Hypˣ" refers to $Hyp^1$, $Hyp^2$, $Hyp^3$, $Hyp^4$ and $Hyp^5$ collectively.

Preferably, the backbone reagent is a compound of formula (a-I), (a-II) or (a-III), more preferably the backbone reagent is a compound of formula (a-I) or (a-III), and most preferably the backbone reagent is a compound of formula (a-I).

In a preferred embodiment, in a compound of formula (a-I), x is 4, 6 or 8. Preferably, in a compound of formula (a-I) x is 4 or 8, most preferably, x is 4.

In a preferred embodiment in the compounds of the formulas (a-I) to (a-IV), $A^0$, $A^1$, $A^2$, $A^3$, $A^4$, $A^5$ and $A^6$ are selected from the group comprising

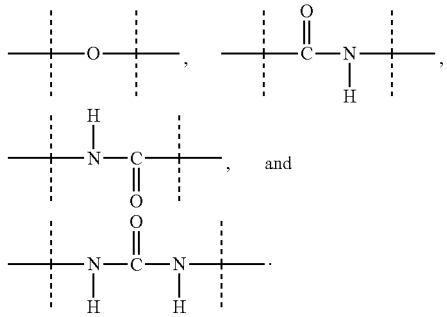

Preferably, in a compound of formula (a-I), $A^0$ is

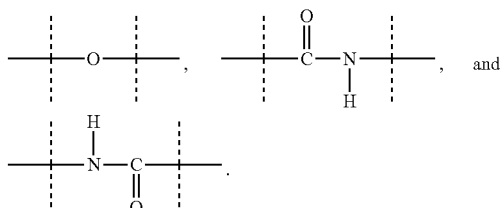

Preferably, in a compound of formula (a-I), $A^1$ is

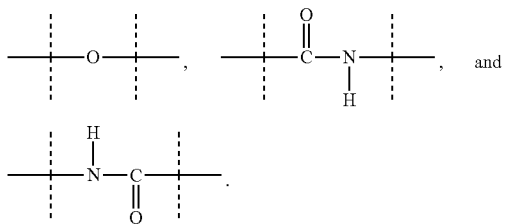

Preferably, in a compound of formula (a-I), $A^2$ is

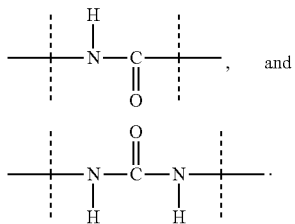

Preferably, in a compound of formula (a-II), $A^3$

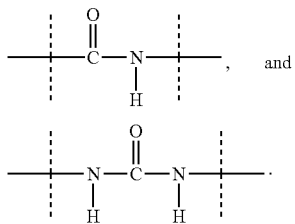

and $A^4$ is

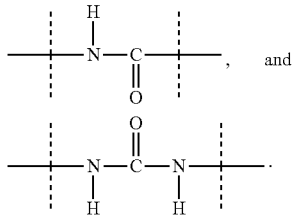

Preferably, in a compound of formula (a-III), $A^5$

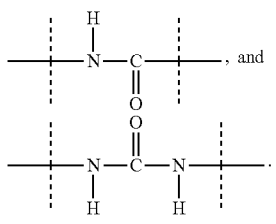

Preferably, in a compound of formula (a-IV), $A^6$ is

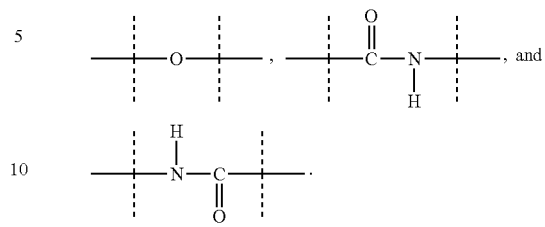

Preferably, in a compound of formula (a-IV), $T^1$ is selected from H and $C_{1-6}$ alkyl.

In one embodiment, in a compound of formula (a-I), the branching core B is selected from the following structures:

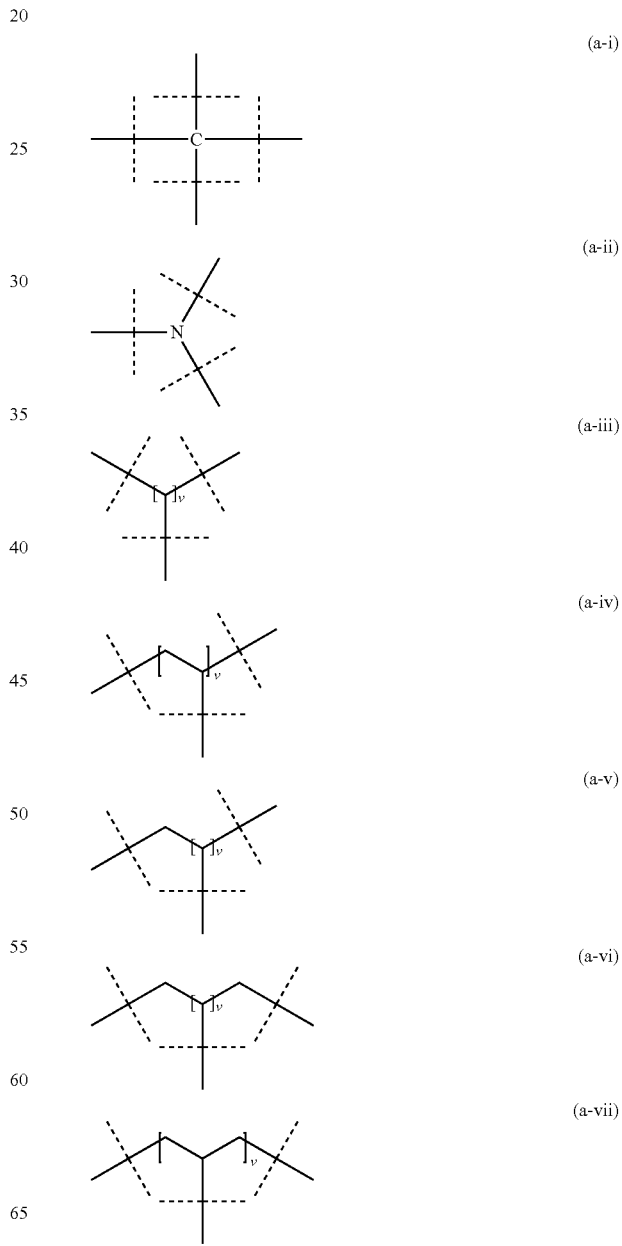

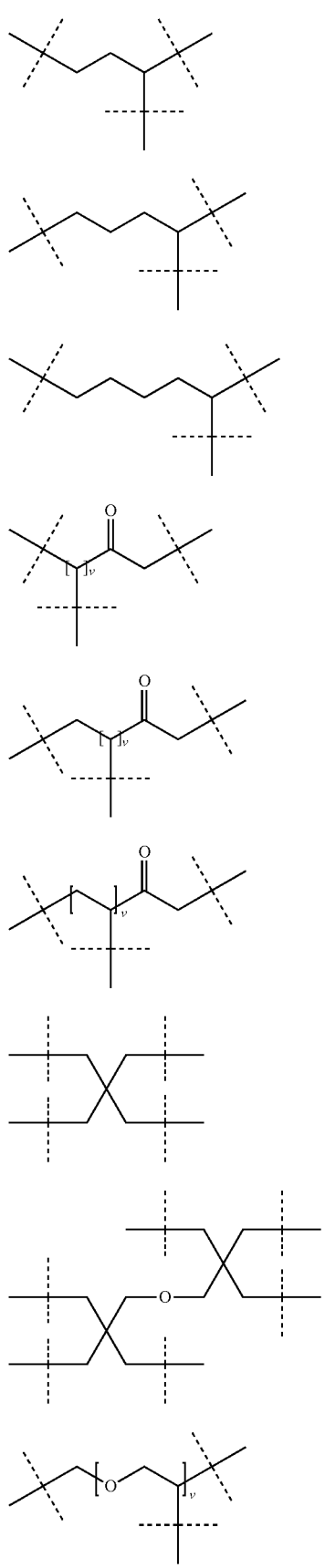
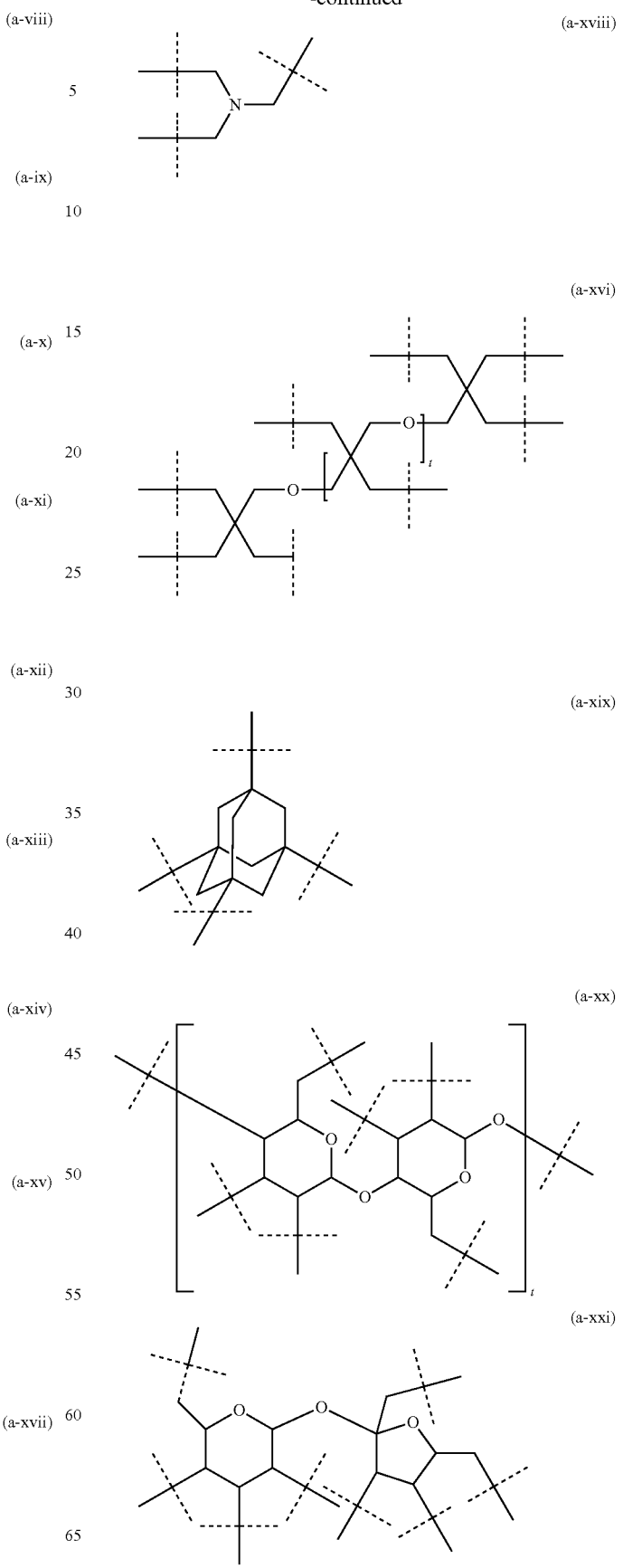

(a-xxii)

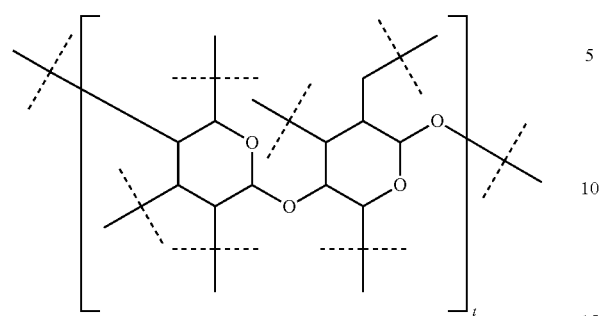

(a-xxiii)

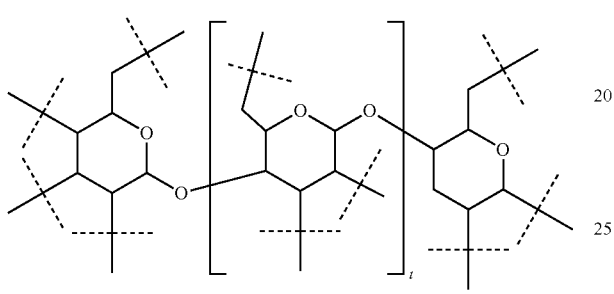

wherein dashed lines indicate attachment to $A^0$ or, if x1 and x2 are both 0, to $A^1$, t is 1 or 2; preferably t is 1, v is 1, 2, 3, 4, 5, 6, 7, 8, 9, 10, 11, 12, 13 or 14; preferably, v is 2, 3, 4, 5, 6; more preferably, v is 2, 4 or 6; most preferably, v is 2.

In a preferred embodiment, B has a structure of formula (a-i), (a-ii), (a-iii), (a-iv), (a-v), (a-vi), (a-vii), (a-viii), (a-ix), (a-x), (a-xiv), (a-xv) or (a-xvi). More preferably, B has a structure of formula (a-iii), (a-iv), (a-v), (a-vi), (a-vii), (a-viii), (a-ix), (a-x) or (a-iv). Most preferably, B has a structure of formula (a-xiv).

A preferred embodiment is a combination of B and $A^0$, or, if x1 and x2 are both 0 a preferred combination of B and $A^1$, which is selected from the following structures:

(b-i)

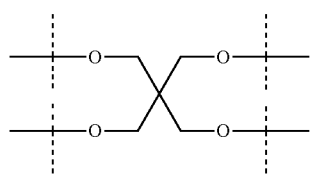

(b-ii)

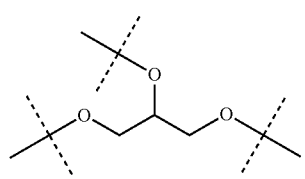

(b-iii)

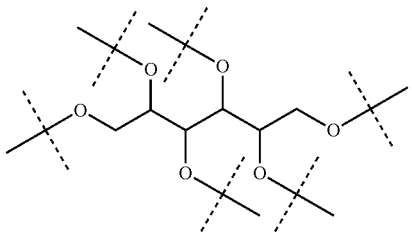

(b-iv)

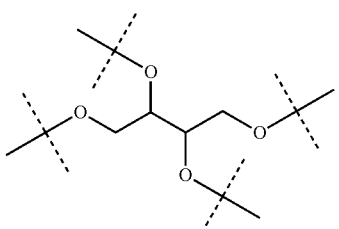

(b-v)

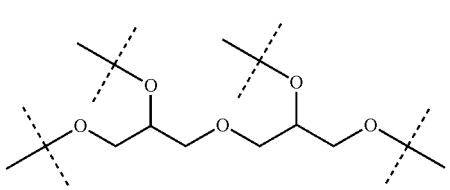

(b-vi)

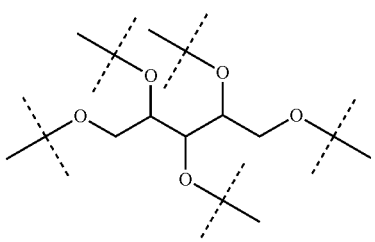

(b-vii)

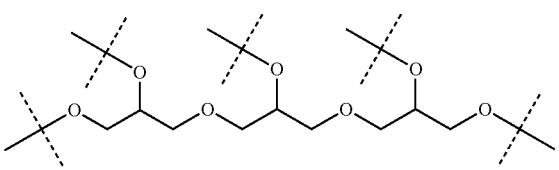

wherein dashed lines indicate attachment to SP or, if x1 and x2 are both 0, to P.

More preferably, the combination of B and $A^0$ or, if x1 and x2 are both 0, the combination of B and $A^1$, has a structure of formula of formula (b-i), (b-iv), (b-vi) or (b-viii) and most preferably has a structure of formula of formula (b-i).

In one embodiment, x1 and x2 of formula (a-I) are 0.

In one embodiment, the PEG-based polymeric chain P has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably P has a molecular weight from 1 to 10 kDa.

In one embodiment, the PEG-based polymeric chain $P^1$ has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably $P^1$ has a molecular weight from 1 to 10 kDa.

In one embodiment, in the compounds of formulas (a-I) or (a-II), P has the structure of formula (c-i):

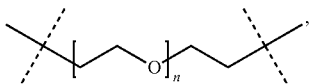

(c-i)

wherein n ranges from 6 to 900, more preferably n ranges from 20 to 700 and most preferably n ranges from 20 to 250.

In one embodiment, in the compounds of formulas (a-III), $P^1$ has the structure of formula (c-ii):

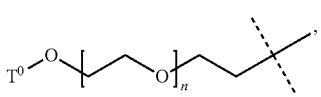

(c-ii)

wherein n ranges from 6 to 900, more preferably n ranges from 20 to 700 and most preferably n ranges from 20 to 250;

$T^0$ is selected from the group comprising $C_{1-6}$ alkyl, $C_{2-6}$ alkenyl and $C_{2-6}$ alkynyl, which is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)— or —S(O)$_2$—.

In one embodiment, in the compounds of formulas (a-I) to (a-IV), the moiety $Hyp^x$ is a polyamine and preferably comprises in bound form and, where applicable, in R- and/or S-configuration a moiety of the formulas (d-i), (d-ii), (d-iii) and/or (d-iv):

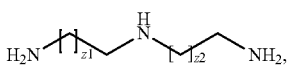

(d-i)

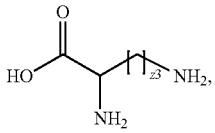

(d-ii)

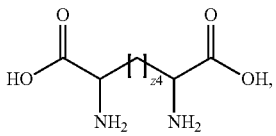

(d-iii)

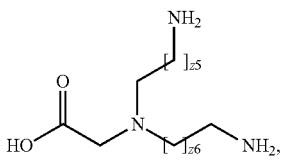

(d-iv)

wherein z1, z2, z3, z4, z5, z6 are independently of each other 1, 2, 3, 4, 5, 6, 7 or 8.

More preferably, $Hyp^x$ comprises in bound form and in R- and/or S-configuration lysine, ornithine, diaminoproprionic acid and/or diaminobutyric acid. $Hyp^x$ comprises in bound form and in R- and/or S-configuration lysine.

$Hyp^x$ has a molecular weight from 40 Da to 30 kDa, preferably from 0.3 kDa to 25 kDa, more preferably from 0.5 kDa to 20 kDa, even more preferably from 1 kDa to 20 kDa and most preferably from 2 kDa to 15 kDa.

$Hyp^x$ is preferably selected from the group consisting of a moiety of formula (e-i)

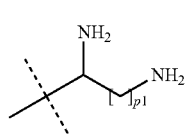

(e-i)

wherein p1 is an integer from 1 to 5, preferably p1 is 4, and the dashed line indicates attachment to $A^2$ if the backbone reagent has a structure of formula (a-I) and to $A^3$ or $A^4$ if the backbone reagent has the structure of formula (a-II);

a moiety of formula (e-ii)

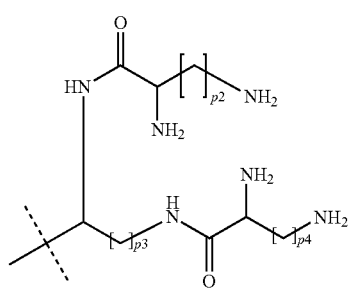

(e-ii)

wherein p2, p3 and p4 are identical or different and each is independently of the others an integer from 1 to 5, preferably p2, p3 and p4 are 4, and the dashed line indicates attachment to $A^2$ if the backbone reagent has a structure of formula (a-I), to $A^3$ or $A^4$ if the backbone reagent has a structure of formula (a-II), to $A^5$ if the backbone reagent has a structure of formula (a-III) and to $A^6$ if the backbone reagent has a structure of formula (a-IV);

a moiety of formula (e-iii)

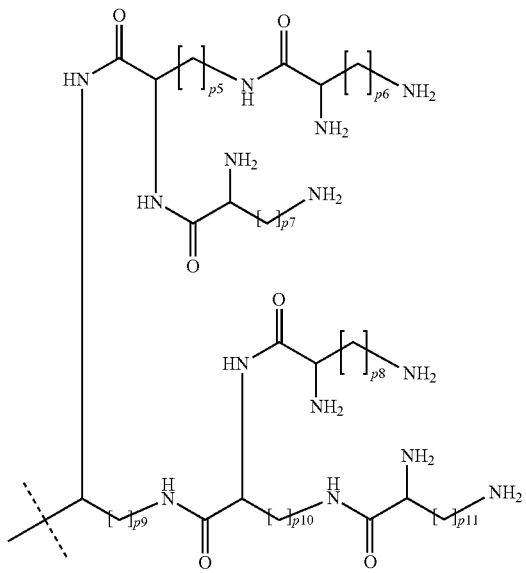

(e-iii)

wherein
p5 to p11 are identical or different and each is independently of the others an integer from 1 to 5, preferably p5 to p11 are 4, and
the dashed line indicates attachment to $A^2$ if the backbone reagent is of formula (a-I), to $A^3$ or $A^4$ if the backbone reagent is of formula (a-II), to $A^5$ if the backbone reagent is of formula (a-III) and to $A^6$ if the backbone reagent is of formula (a-IV);
a moiety of formula (e-iv)

(e-iv)

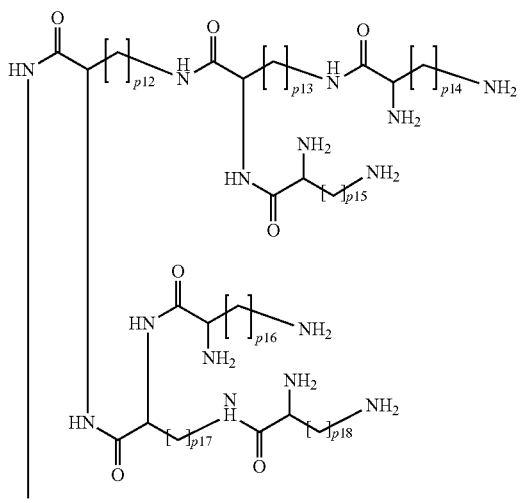

-continued

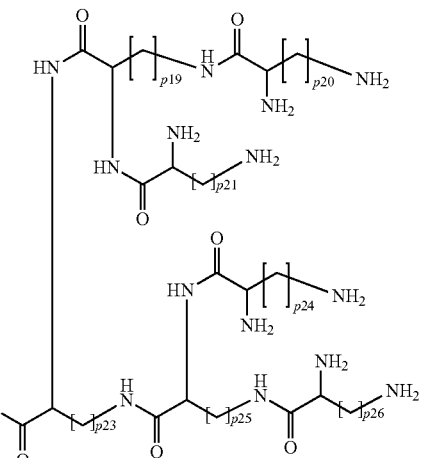

wherein
p12 to p26 are identical or different and each is independently of the others an integer from 1 to 5, preferably p12 to p26 are 4, and
the dashed line indicates attachment to $A^2$ if the backbone reagent has a structure of formula (a-I), to $A^3$ or $A^4$ if the backbone reagent has a structure of formula (a-II), to $A^5$ if the backbone reagent has a structure of formula (a-III) and to $A^6$ if the backbone reagent has a structure of formula (a-IV);
a moiety of formula (e-v)

(e-v)

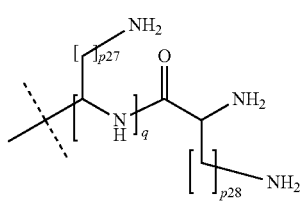

wherein
p27 and p28 are identical or different and each is independently of the other an integer from 1 to 5, preferably p27 and p28 are 4,
q is an integer from 1 to 8, preferably q is 2 or 6 and most preferably 1 is 6, and
the dashed line indicates attachment to $A^2$ if the backbone reagent has a structure of formula (a-I), to $A^3$ or $A^4$ if the backbone reagent has a structure of formula (a-II), to $A^5$ if the backbone reagent has a structure of formula (a-III) and to $A^6$ if the backbone reagent has a structure of formula (a-IV);
a moiety of formula (e-vi)

(e-vi)

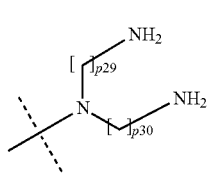

wherein
p29 and p30 are identical or different and each is independently of the other an integer from 2 to 5, preferably p29 and p30 are 3, and
the dashed line indicates attachment to $A^2$ if the backbone reagent has the structure of formula (a-I), to $A^3$ or $A^4$ if the backbone reagent has the structure of formula (a-II), to $A^5$ if the backbone reagent has the structure of formula (a-III) and to $A^6$ if the backbone reagent has the structure of formula (a-IV);
a moiety of formula (e-vii)

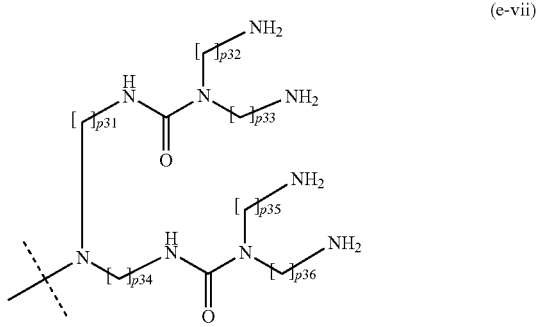

(e-vii)

wherein
p31 to p36 are identical or different and each is independently of the others an integer from 2 to 5, preferably p31 to p36 are 3, and
the dashed line indicates attachment to $A^2$ if the backbone reagent has a structure of formula (a-I), to $A^3$ or $A^4$ if the backbone reagent has a structure of formula (a-II), to $A^5$ if the backbone reagent has a structure of formula (a-III) and to $A^6$ if the backbone reagent has a structure of formula (a-IV);
a moiety of formula (e-viii)

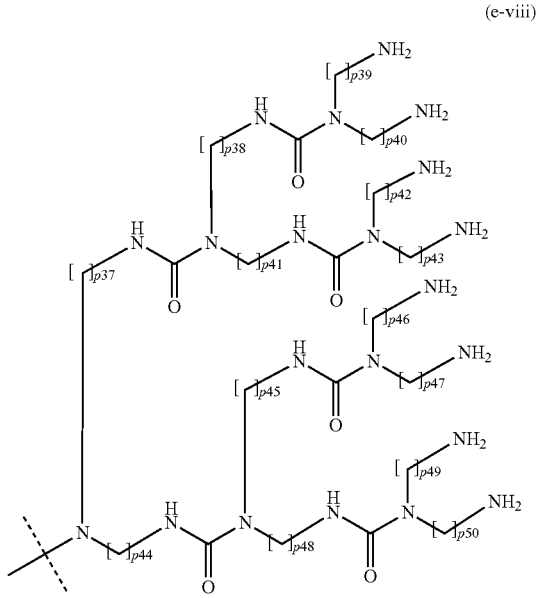

(e-viii)

wherein
p37 to p50 are identical or different and each is independently of the others an integer from 2 to 5, preferably p37 to p50 are 3, and the dashed line indicates attachment to $A^2$ if the backbone reagent has a structure of formula (a-I), to $A^3$ or $A^4$ if the backbone reagent has a structure of formula (a-II), to $A^5$ if the backbone reagent has a structure of formula (a-III) and to $A^6$ if the backbone reagent has a structure of formula (a-IV); and
a moiety of formula (e-ix):

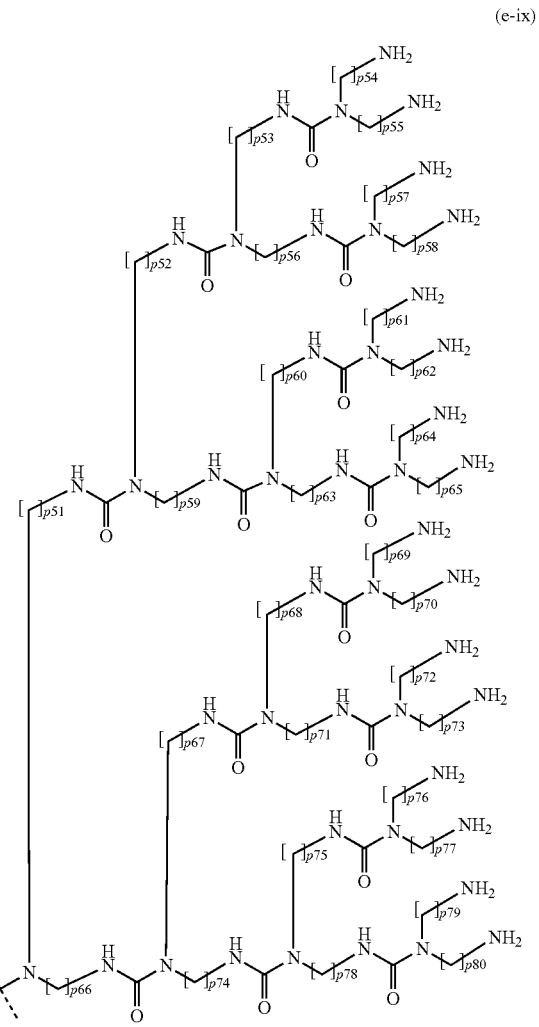

(e-ix)

wherein
p51 to p80 are identical or different and each is independently of the others an integer from 2 to 5, preferably p51 to p80 are 3, and
the dashed line indicates attachment to $A^2$ if the backbone reagent has a structure of formula (a-I), to $A^3$ or $A^4$ if the backbone reagent has a structure of formula (a-II), to $A^5$ if the backbone reagent has a structure of formula (a-III) and to $A^6$ if the backbone reagent has a structure of formula (a-IV); and
wherein the moieties (e-i) to (e-v) may at each chiral center be in either R- or S-configuration, preferably, all chiral centers of a moiety (e-i) to (e-v) are in the same configuration.
Preferably, $Hyp^x$ is has a structure of formulas (e-i), (e-ii), (e-iii), (e-iv), (e-vi), (e-vii), (e-viii) or (e-ix). More preferably, $Hyp^x$ has a structure of formulas (e-ii), (e-iii), (e-iv), (e-vii), (e-viii) or (e-ix), even more preferably $Hyp^x$ has a structure of formulas (e-ii), (e-iii), (e-vii) or (e-viii) and most preferably Hyp$^x$ has the structure of formula (e-iii).

If the backbone reagent has a structure of formula (a-I), a preferred moiety -A$^2$-Hyp$^1$ is a moiety of the formula

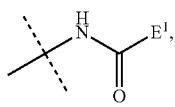

wherein
the dashed line indicates attachment to P; and
E$^1$ is selected from formulas (e-i) to (e-ix).

If the backbone reagent has a structure of formula (a-II) a preferred moiety Hyp$^2$-A$^3$- is a moiety of the formula

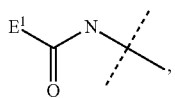

wherein
the dashed line indicates attachment to P; and
E$^1$ is selected from formulas (e-i) to (e-ix);
and a preferred moiety -A$^4$-Hyp$^3$ is a moiety of the formula

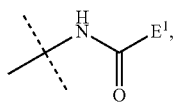

wherein
the dashed line indicates attachment to P; and
E$^1$ is selected from formulas (e-i) to (e-ix).

If the backbone reagent has a structure of formula (a-III), a preferred moiety -A$^5$-Hyp$^4$ is a moiety of the formula

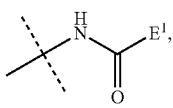

wherein
the dashed line indicates attachment to P$^1$; and
E$^1$ is selected from formulas (e-i) to (e-ix).

More preferably, the backbone reagent has a structure of formula (a-I) and B is has a structure of formula (a-xiv).

Even more preferably, the backbone reagent has the structure of formula (a-I), B has the structure of formula (a-xiv), x1 and x2 are 0, and A$^1$ is —O—.

Even more preferably, the backbone reagent has the structure of formula (a-I), B has the structure of formula (a-xiv), A$^1$ is —O—, and P has a structure of formula (c-i).

Even more preferably, the backbone reagent is formula (a-I), B is of formula (a-xiv), x1 and x2 are 0, A$^1$ is —O—, P is of formula (c-i), A$^2$ is —NH—(C=O)— and Hyp$^1$ is of formula (e-iii).

Most preferably, the backbone reagent has the following formula:

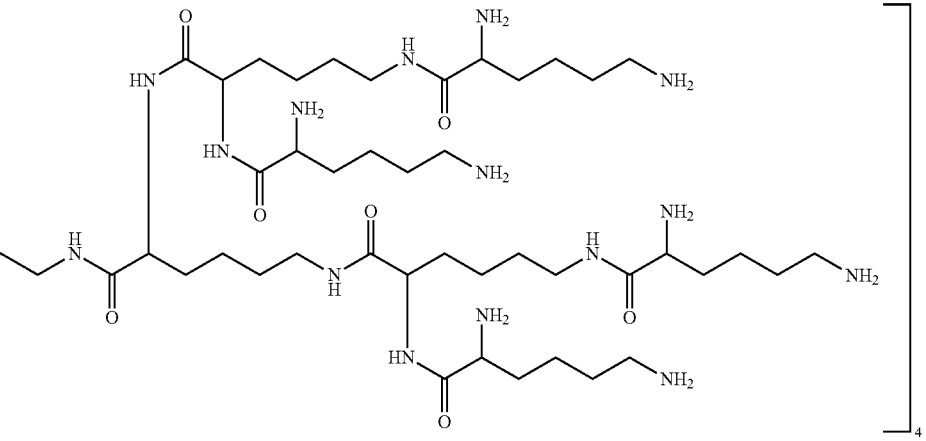

wherein
n ranges from 10 to 40, preferably from 10 to 30, more preferably from 10 to 20.

Equally preferably, n ranges from 20 to 30 kDa and most preferably n is 28.

SP is a spacer moiety selected from the group comprising $C_{1-6}$ alkyl, $C_{2-6}$ alkenyl and $C_{2-6}$ alkynyl, preferably SP is —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, —CH=CH— or —CH=CH—, most preferably SP is —$CH_2$—, —$CH_2$—$CH_2$— or —CH=CH—.

The at least one crosslinker reagent comprises at least two carbonyloxy groups (—(C=O)—O— or —O—(C=O)—), which are biodegradable linkages. These biodegradable linkages are necessary to render the hydrogel biodegradable. Additionally, the at least one crosslinker reagent comprises at least two activated functional end groups which during the polymerization of step (b) react with the amines of the at least one backbone reagent.

The crosslinker reagent has a molecular weight ranging from 6 to 40 kDa, more preferably ranging from 6 to 30 kDa, even more preferably ranging from 6 to 20 kDa, even more preferably ranging from 6 to 15 kDa and most preferably ranging from 6 to 10 kDa.

In an equally preferred embodiment the crosslinker reagent has a molecular weight ranging from 0.5 kDa to 15 kDa, preferably from 1 kDa to 10 kDa and most preferably from 2 to 5 kDa.

The crosslinker reagent comprises at least two activated functional end groups selected from the group comprising activated ester groups, activated carbamate groups, activated carbonate groups and activated thiocarbonate groups, which during polymerization react with the amine groups of the backbone reagents, forming amide bonds.

In one preferred embodiment, the crosslinker reagent is a compound of formula (V-I):

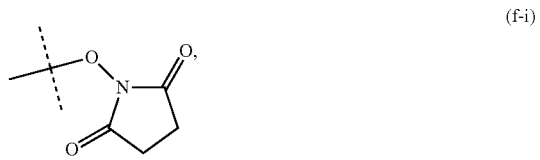

(V-I)

wherein
each $D^1$, $D^2$, $D^3$ and $D^4$ are identical or different and each is independently of the others selected from the group comprising —O—, —$NR^5$—, —S— and —$CR^6R^{6a}$—;
each $R^1$, $R^{1a}$, $R^2$, $R^{2a}$, $R^3$, $R^{3a}$, $R^4$, $R^{4a}$, $R^6$ and $R^{6a}$ are identical or different and each is independently of the others selected from the group comprising —H, —$OR^7$, —$NR^7R^{7a}$, —$SR^7$ and $C_{1-6}$ alkyl; optionally, each of the pair(s) $R^1/R^2$, $R^3/R^4$, $R^{1a}/R^{2a}$, and $R^{3a}/R^{4a}$ may independently form a chemical bond and/or each of the pairs $R^1/R^{1a}$, $R^2/R^{2a}$, $R^3/R^{3a}$, $R^4/R^{4a}$, $R^6/R^{6a}$, $R^1/R^2$, $R^3/R^4$, $R^{1a}/R^{2a}$, and $R^{3a}/R^{4a}$ are independently of each other joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;
each $R^5$ is independently selected from —H and $C_{1-6}$ alkyl; optionally, each of the pair(s) $R^1/R^5$, $R^2/R^5$, $R^3/R^5$, $R^4/R^5$ and $R^5/R^6$ may independently form a chemical bond and/or are joined together with the atom to which they are attached to form a 4- to 7-membered heterocyclyl or 8- to 11-membered heterobicyclyl;
each $R^7$, $R^{7a}$ is independently selected from H and $C_{1-6}$ alkyl;
A is selected from the group consisting of indenyl, indanyl and tetralinyl;
$P^2$ is

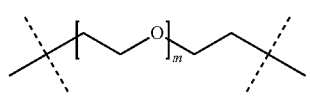

m ranges from 120 to 920 or from 10 to 340, preferably from 120 to 460 or from 20 to 220 and more preferably from 120 to 230 or from 45 to 110;
r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vi):

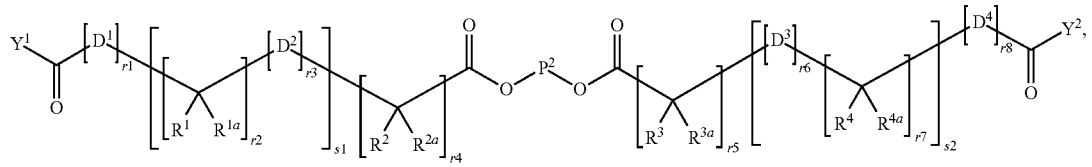

(f-i)

-continued

(f-ii)

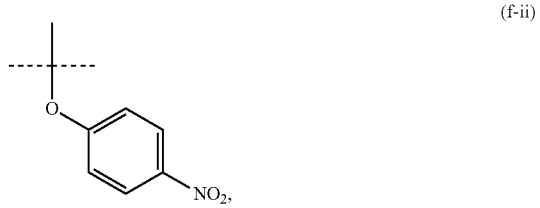

(f-iii)

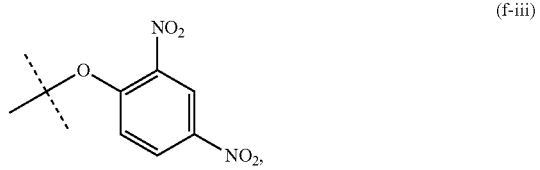

-continued (f-iv)
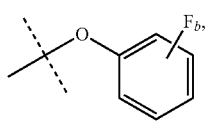

(f-v)
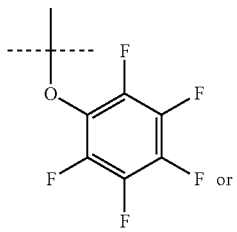

(f-vi)
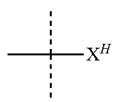

wherein
the dashed lines indicate attachment to the rest of the molecule,
b is 1, 2, 3 or 4
$X^H$ is Cl, Br, I, or F.

Preferably, the crosslinker reagent is a compound of formula (V-II):

r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vi):

(f-i)
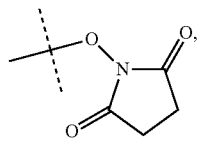

(f-ii)
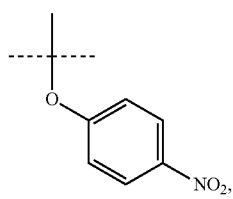

(V-II)
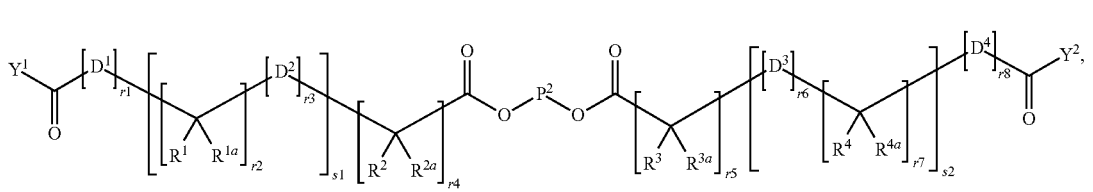

wherein
$D^1$, $D^2$, $D^3$ and $D^4$ are identical or different and each is independently of the others selected from the group comprising O, $NR^5$, S and $CR^5R^{5a}$;
$R^1$, $R^{1a}$, $R^2$, $R^{2a}$, $R^3$, $R^{3a}$, $R^4$, $R^{4a}$, $R^5$ and $R^{5a}$ are identical or different and each is independently of the others selected from the group comprising H and $C_{1-6}$ alkyl; optionally, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ form a chemical bond or are joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;
A is selected from the group consisting of phenyl, naphthyl, indenyl, indanyl and tetralinyl;
$P^2$ is

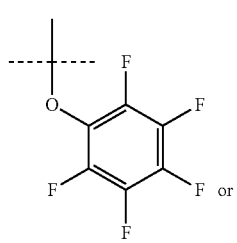

m ranges from 120 to 920 or from 10 to 340, preferably from 120 to 460 or from 20 to 220 and more preferably from 120 to 230 or from 45 to 110, -continued (f-iii)
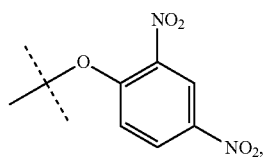

(f-iv)
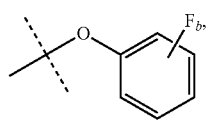

(f-v)

-continued

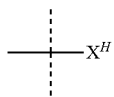
(f-vi)

wherein
the dashed lines indicate attachment to the rest of the molecule,
b is 1, 2, 3 or 4
$X^H$ is Cl, Br, I, or F.
It is understood that the moieties

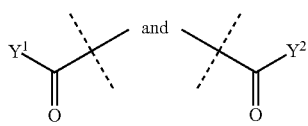

represent the at least two activated functional end groups.

Preferably, $Y^1$ and $Y^2$ of formula (V-I) and (V-II) have a structure of formula (f-i), (f-ii) or (f-v). More preferably, $Y^1$ and $Y^2$ have a structure of formula (f-i) or (f-ii) and most preferably, $Y^1$ and $Y^2$ have a structure of formula (f-i).

Preferably, both moieties $Y^1$ and $Y^2$ of formula (V-I) and (V-II) have the same structure. More preferably, both moieties $Y^1$ and $Y^2$ have the structure of formula (f-i).

Preferably, r1 of formula (V-I) and (V-II) is 0.

Preferably, r1 and s1 of formula (V-I) and (V-II) are both 0.

Preferably, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ of formula (V-I) and (V-II) form a chemical bond or are joined together with the atom to which they are attached to form a $C_{3-8}$ cycloalkyl or form a ring A.

Preferably, one or more of the pair(s) $R^1/R^2$, $R^{1a}/R^{2a}$, $R^3/R^4$, $R^{3a}/R^{4a}$ of formula (V-I) and (V-II) are joined together with the atom to which they are attached to form a 4- to 7-membered heterocyclyl or 8- to 11-membered heterobicyclyl.

Preferably, the crosslinker reagent of formula (V-I) and (V-II) is symmetric, i.e. the moiety

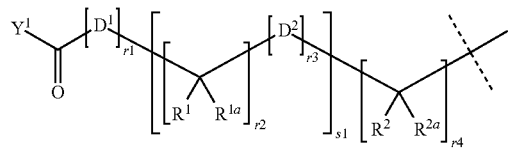

has the same structure as the moiety

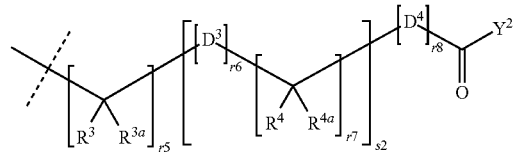

In one preferred embodiment s1, s2, r1 and r8 of formula (V-I) and (V-II) are 0.

In another preferred embodiment s1, s2, r1 and r8 of formula (V-I) and (V-II) are 0 and r4 of formula (V-I) and (V-II) and r5 are 1.

Preferred crosslinker reagents are of formula (V-1) to (V-54):

(V-1)
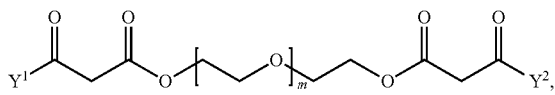

(V-2)
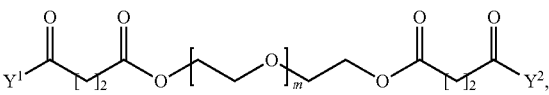

(V-3)
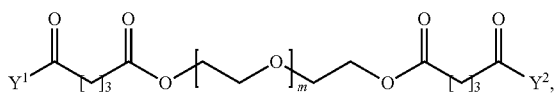

(V-4)
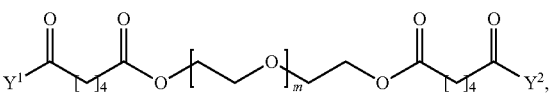

(V-5)
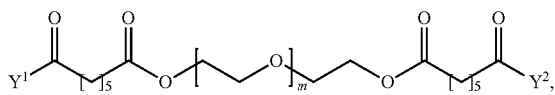

(V-6)
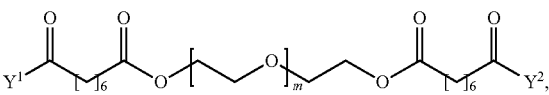

(V-7)
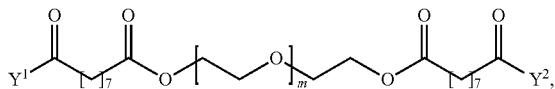

(V-8)
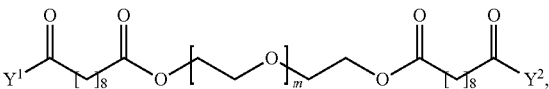

(V-9)
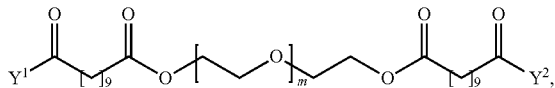

(V-10)
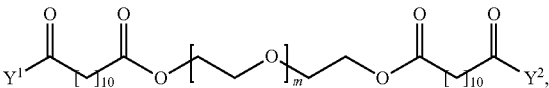

-continued
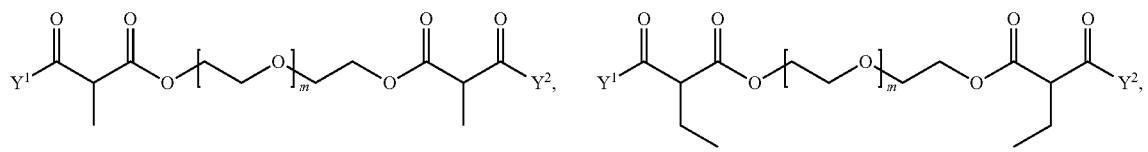
(V-11) (V-12)
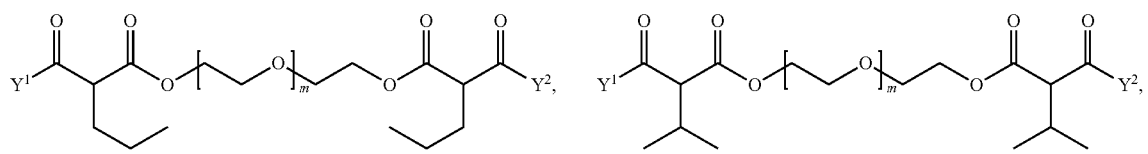
(V-13) (V-14)
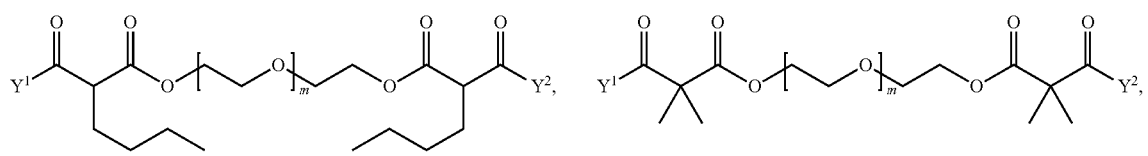
(V-15) (V-16)
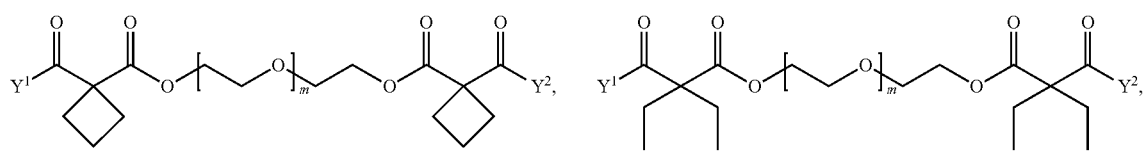
(V-17) (V-18)
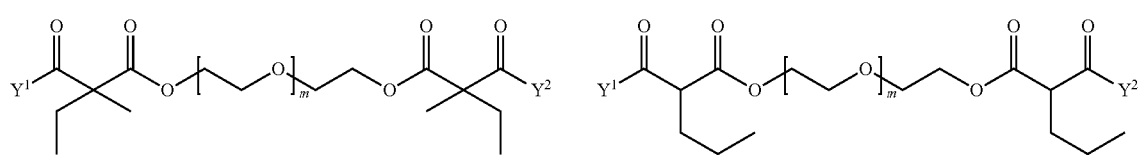
(V-19) (V-20)
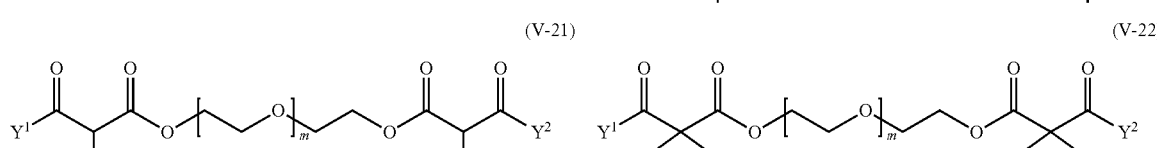
(V-21) (V-22)
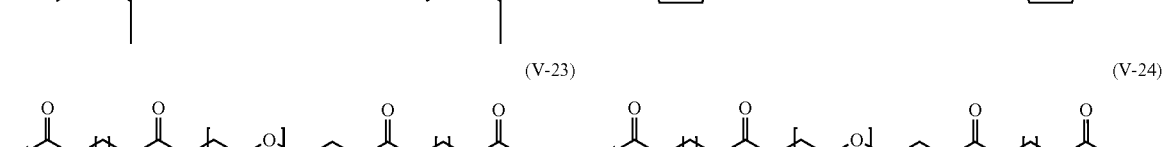
(V-23) (V-24)
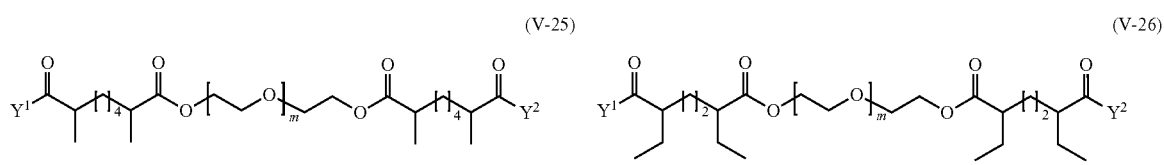
(V-25) (V-26)
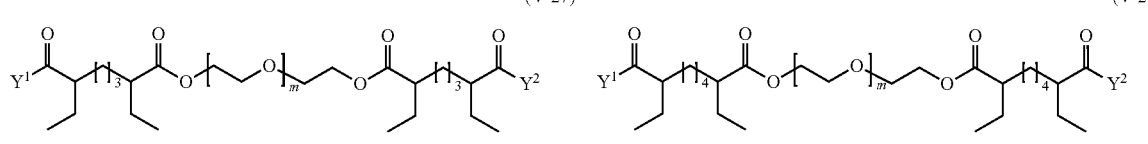
(V-27) (V-28)

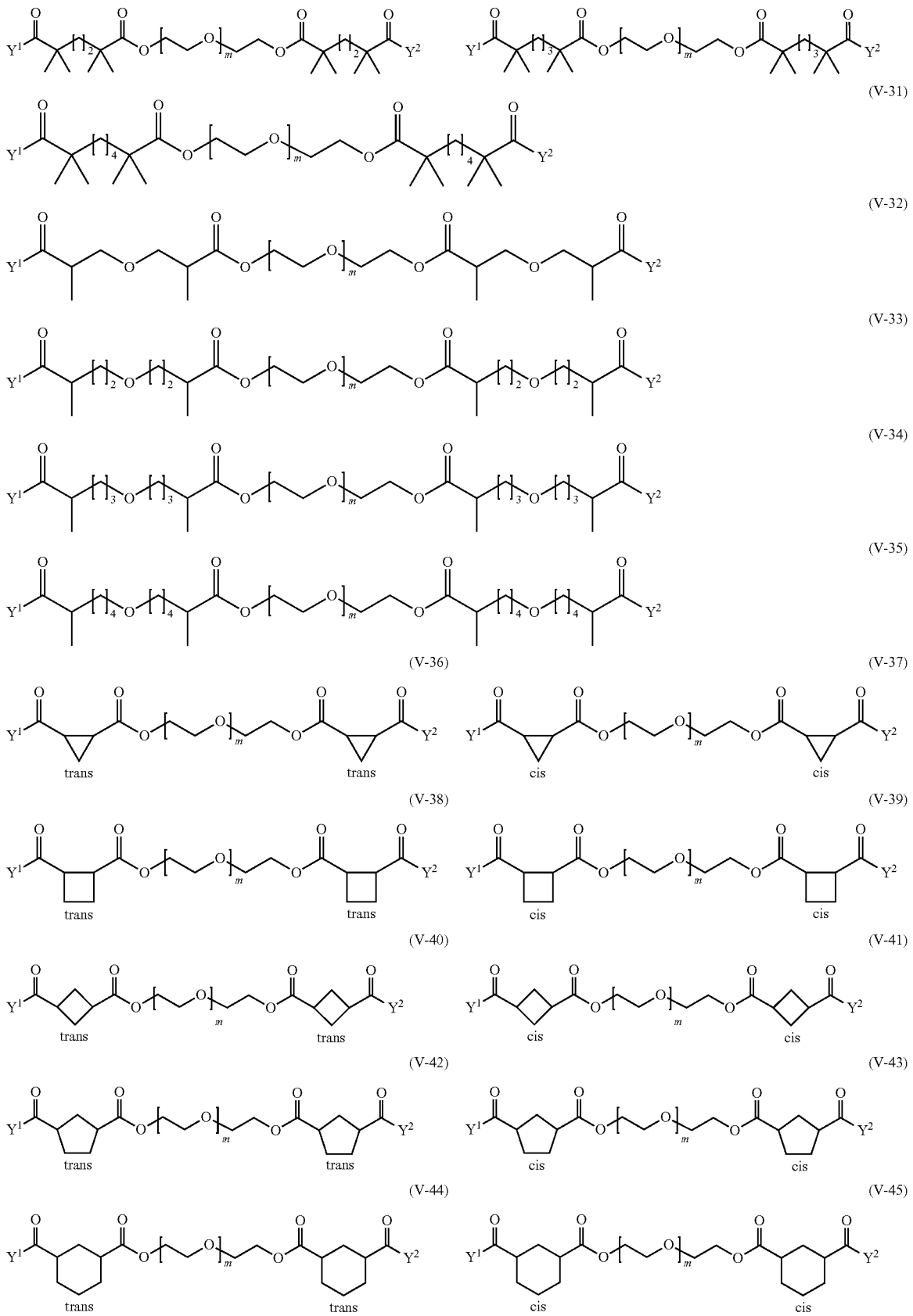

-continued
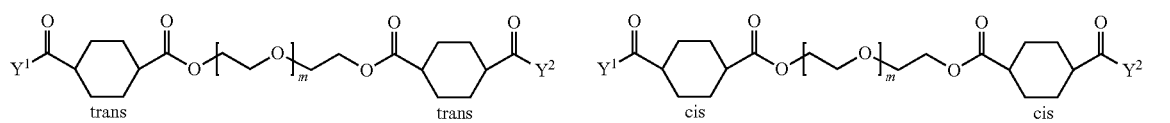
(V-46)
(V-47)
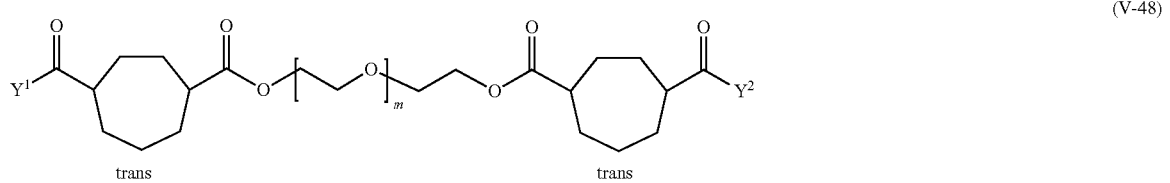
(V-48)
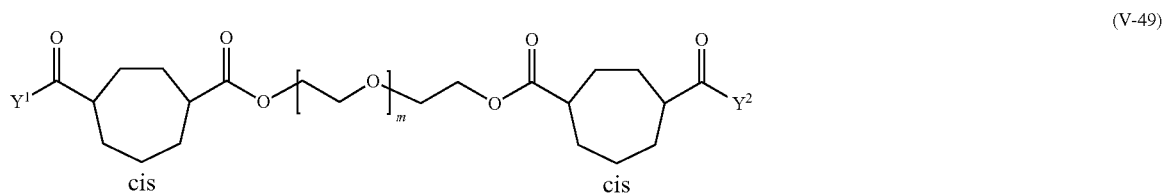
(V-49)
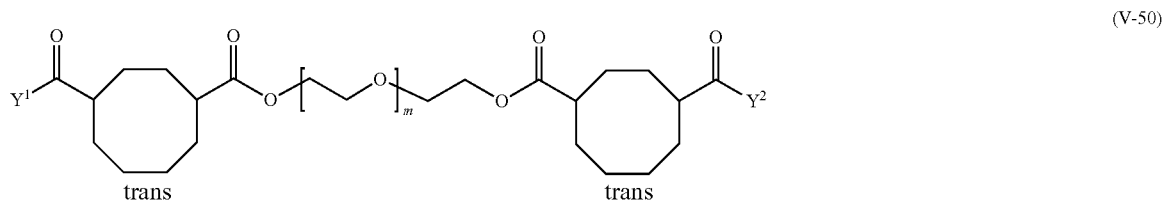
(V-50)
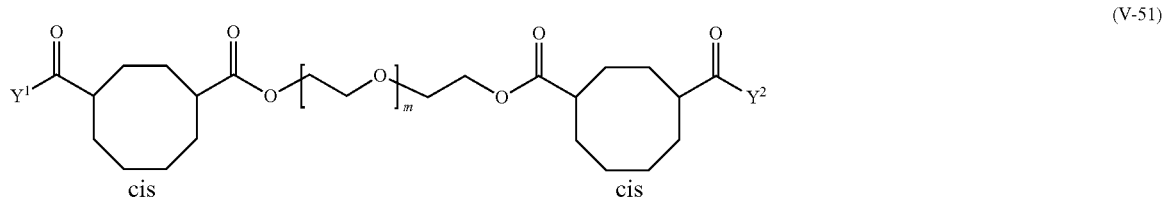
(V-51)
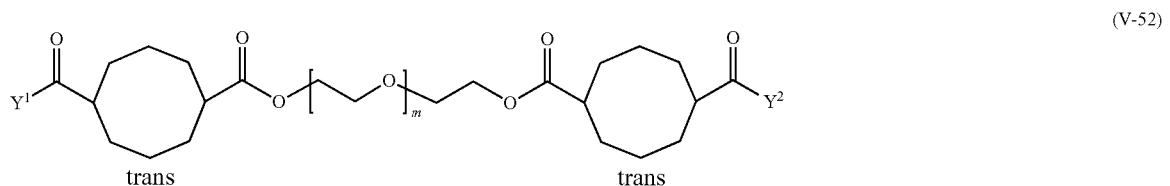
(V-52)
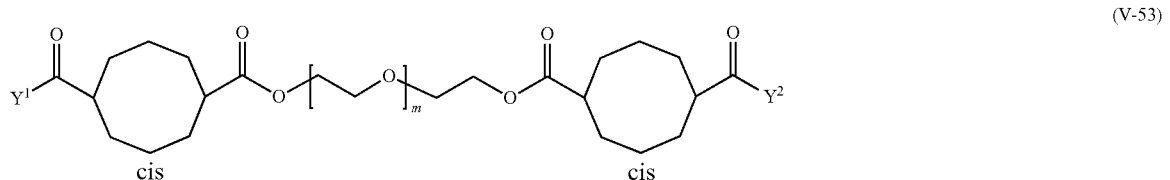
(V-53)
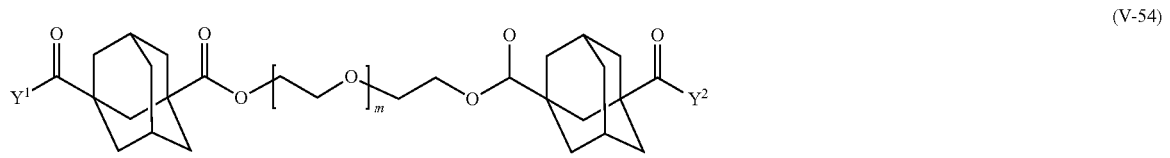
(V-54)

wherein
each crosslinker reagent may be in the form of its racemic mixture, where applicable; and
m, $Y^1$ and $Y^2$ are defined as above.
Even more preferred crosslinker reagents are of formula (Va-1) to (Va-54):
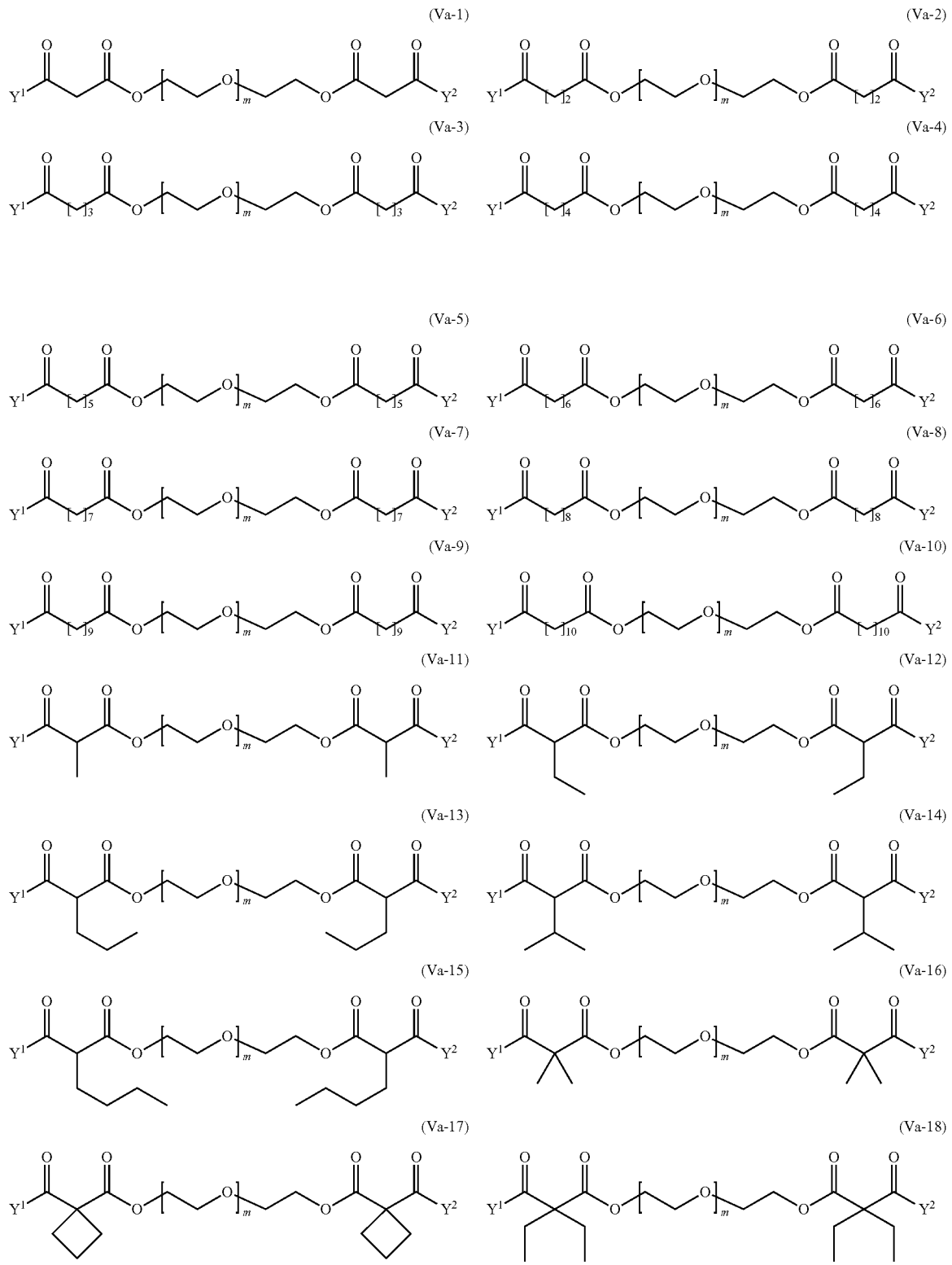

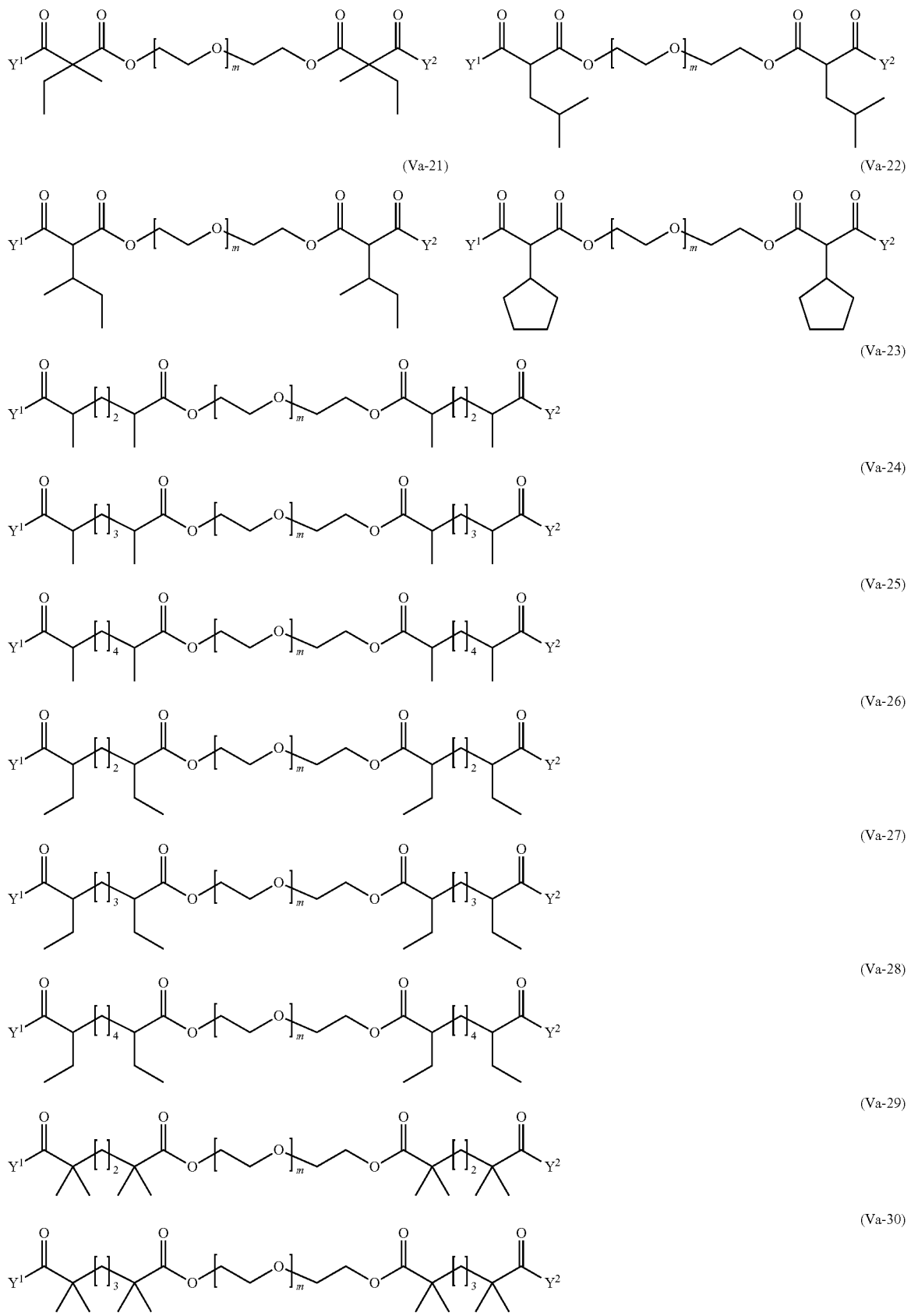

-continued
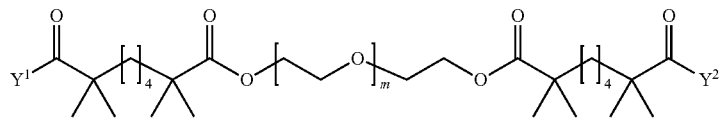
(Va-31)
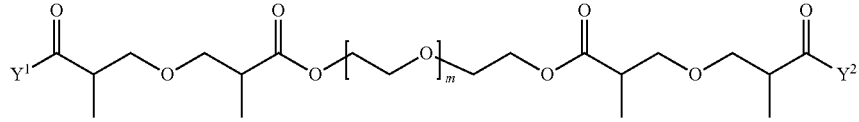
(Va-32)
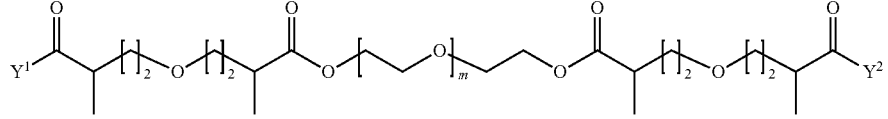
(Va-33)
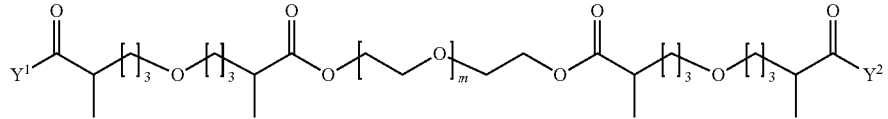
(Va-34)
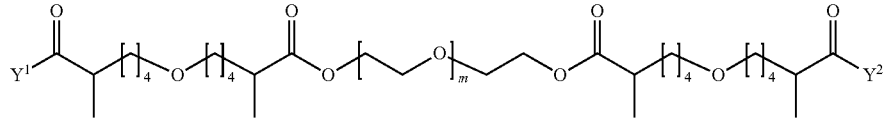
(Va-35)
(Va-36) 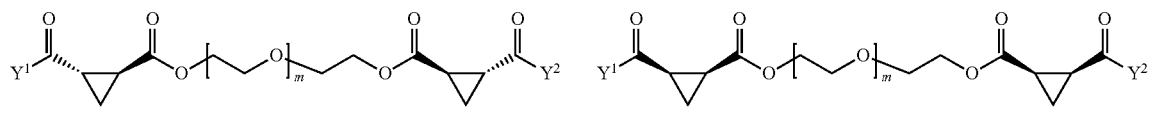 (Va-37)
(Va-38) 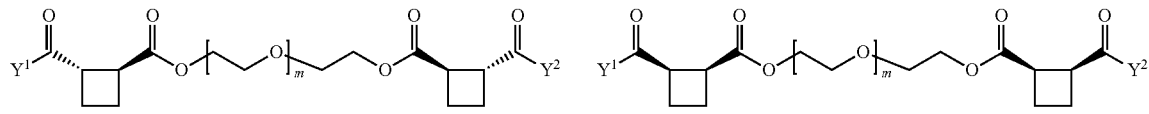 (Va-39)
(Va-40) 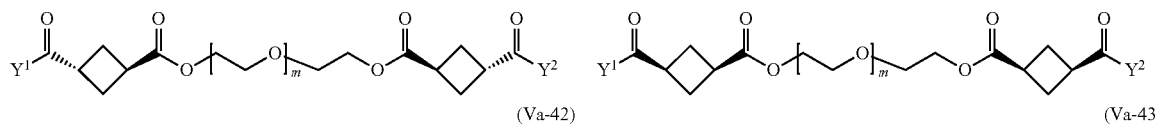 (Va-41)
(Va-42) 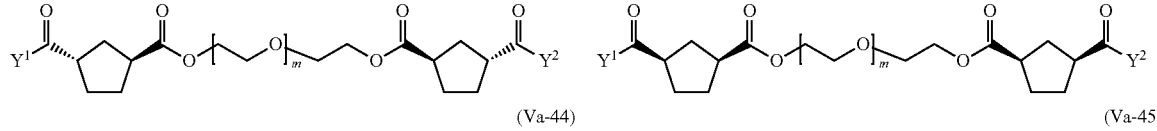 (Va-43)
(Va-44) 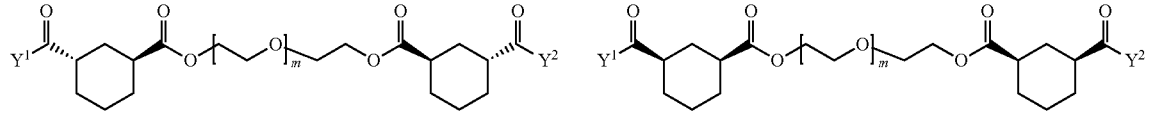 (Va-45)
(Va-46) 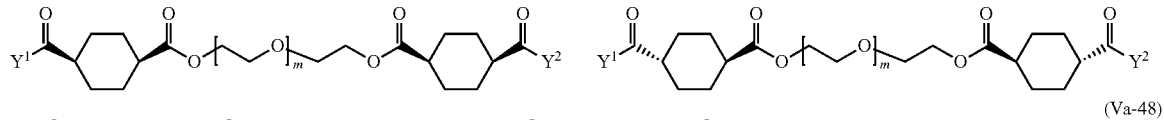 (Va-47)
(Va-48)
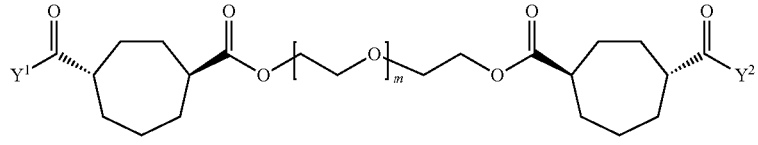

-continued

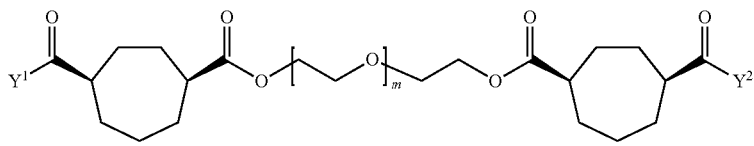
(Va-49)

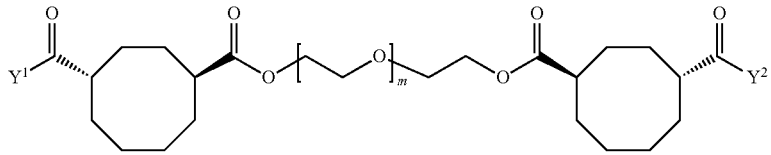
(Va-50)

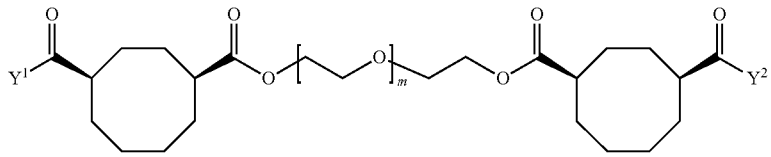
(Va-51)

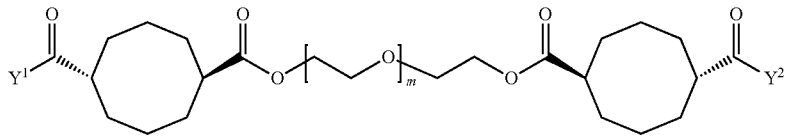
(Va-52)

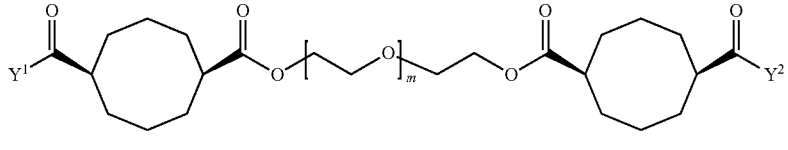
(Va-53)

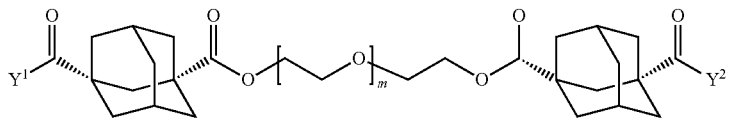
(Va-54)

wherein each crosslinker reagent may be in the form of its racemic mixture, where applicable; and m, $Y^1$ and $Y^2$ are defined as above.

It was surprisingly found that the use of crosslinker reagents with branches, i.e. residues other than H, at the alpha carbon of the carbonyloxy group lead to the formation of hydrogels which are more resistant against enzymatic degradation, such as degradation through esterases.

Similarly, it was surprisingly found that the fewer atoms there are between the (C=O) of a carbonyloxy group and the (C=O) of the adjacent activated ester, activated carbamate, activated carbonate or activated thiocarbamate, the more resistant against degradation the resulting hydrogels are, such as more resistant against degradation through esterases.

Accordingly, crosslinker reagents V-11 to V-53, V-1 and V-2 are preferred crosslinker reagents.

In another embodiment, crosslinker reagents V-1, V-2, V-5, V-6, V-7, V-8, V-9, V-10, V-11, V-12, V-13, V-14, V-15, V-16, V-17, V-18, V-19, V-20, V-21, V-22, V-23, V-24, V-25, V-26, V-27, V-28, V-29, V-30, V-31, V-32, V-33, V-34, V-35, V-36, V-37, V-38, V-39, V-40, V-41, V-42, V-43, V-44, V-45, V-46, V-47, V-48, V-49, V-50, V-51, V-52, V-53 an V-54 are preferred crosslinker reagents. More preferably, the at least one crosslinker reagent is of formula V-5, V-6, V-7, V-8, V-9, V-10, V-14, V-22, V-23, V-43, V-44, V-45 or V-46, and most preferably, the at least one crosslinker reagent is of formula V-5, V-6, V-9 or V-14.

In another embodiment, crosslinker reagents Va-1, Va-2, Va-5, Va-6, Va-7, Va-8, Va-9, Va-10, Va-11, Va-12, Va-13, Va-14, Va-15, Va-16, Va-17, Va-18, Va-19, Va-20, Va-21, Va-22, Va-23, Va-24, Va-25, Va-26, Va-27, Va-28, Va-29, Va-30, Va-31, Va-32, Va-33, Va-34, Va-35, Va-36, Va-37, Va-38, Va-39, Va-40, Va-41, Va-42, Va-43, Va-44, Va-45, Va-46, Va-47, Va-48, Va-49, Va-50, Va-51, Va-52, Va-53 an Va-54 are even more preferred crosslinker reagents. More preferably, the at least one crosslinker reagent is of formula Va-5, Va-6, Va-7, Va-8, Va-9, Va-10, Va-14, Va-22, Va-23, Va-43, Va-44, Va-45 or Va-46, and most preferably, the at least one crosslinker reagent is of formula Va-5, Va-6, Va-9 or Va-14.

The preferred embodiments of the compound of formula (V-I) and (V-II) as mentioned above apply accordingly to the preferred compounds of formulas (V-1) to (V-53).

The hydrogel contains from 0.01 to 1 mmol/g primary amine groups (—$NH_2$), more preferably, from 0.02 to 0.5 mmol/g primary amine groups and most preferably from 0.05 to 0.3 mmol/g primary amine groups. The term "X mmol/g primary amine groups" means that 1 g of dry hydrogel comprises X mmol primary amine groups. Measurement of the amine content of the hydrogel may be carried out according to Gude et al. (Letters in Peptide Science, 2002, 9(4): 203-206, which is incorporated by reference in its entirety).

Preferably, the term "dry" as used herein means having a residual water content of a maximum of 10%, preferably less than 5% and more preferably less than 2% (determined according to Karl Fischer). The preferred method of drying is lyophilization.

In one embodiment the hydrogel carrier of the polymeric prodrug is further modified before a reversible prodrug linker-biologically active moiety is conjugated to the hydrogel.

Preferably, the hydrogel is modified by a process comprising the steps of
(A) providing a hydrogel having groups $A^{x0}$, wherein groups $A^{x0}$ represent the same or different, preferably same, functional groups;
(B) optionally covalently conjugating a spacer reagent of formula (VI)

$$A^{x1}\text{-}SP^2\text{-}A^{x2} \qquad (VI),$$

wherein
SP$^2$ is $C_{1-50}$ alkyl, $C_{2-50}$ alkenyl or $C_{2-50}$ alkynyl, which $C_{1-50}$ alkyl, $C_{2-50}$ alkenyl and $C_{2-50}$ alkynyl is optionally interrupted by one or more group(s) selected from the group consisting of —NH—, —N($C_{1-4}$ alkyl)-, —O—, —S, —C(O)—, —C(O)NH, —C(O)N($C_{1-4}$ alkyl)-, —O—C(O)—, —S(O)—, —S(O)$_2$—, 4- to 7-membered heterocyclyl, phenyl and naphthyl;
$A^{x1}$ is a functional group for reaction with $A^{x0}$ of the hydrogel; and
$A^{x2}$ is a functional group;
to $A^{x0}$ of the hydrogel from step (A); and
(C) reacting the hydrogel of step (A) or step (B) with a reagent of formula (VII)

$$A^{x3}\text{-}Z \qquad (VII),$$

wherein
$A^{x3}$ is a functional group; and
Z is an inert moiety having a molecular weight ranging from 10 Da to 1000 kDa;
such that at most 99 mol-% of $A^{x0}$ or $A^{x2}$ react with $A^{x3}$.

Preferably, $A^{x0}$ of step (A) is selected from the group consisting of maleimide, amine (—NH$_2$ or —NH—), hydroxyl (—OH), thiol (—SH), carboxyl (—COOH) and activated carboxyl (—COY$^1$, wherein Y$^1$ is selected from formulas (f-i) to (f-vi):

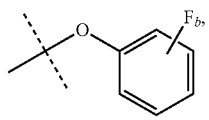  (f-iv)

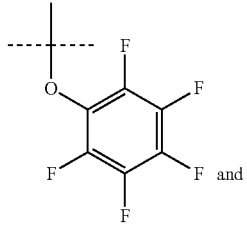 and  (f-v)

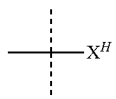  (f-vi)

wherein
the dashed lines indicate attachment to the rest of the molecule,
b is 1, 2, 3 or 4;
$X^H$ is Cl, Br, I, or F).

More preferably, $A^{x0}$ of step (A) is an amine or maleimide.

It is understood that the functional groups $A^{x0}$ of step (A) correspond to the amines of the at least one backbone reagent, if the hydrogel carrier of the polymer prodrug is obtained by the process described above.

In a preferred embodiment $A^{x0}$ of step (A) is an amine and $A^{x1}$ of step (B) is ClSO$_2$—, R$^1$(C=O)—, I—, Br—, Cl—, SCN—, CN—, O=C=N—, Y$^1$—(C=O)—, Y$^1$—(C=O)—NH—, or Y$^1$—(C=O)—O—, wherein
R$^1$ is H, $C_{1-6}$ alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, or tetralinyl; and
Y$^1$ is selected from formulas (f-i) to (f-vi):

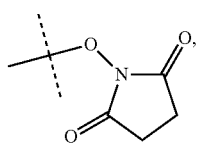  (f-i)

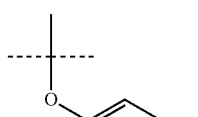  (f-ii)

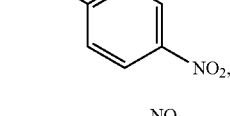  (f-iii)

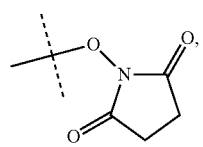  (f-i)

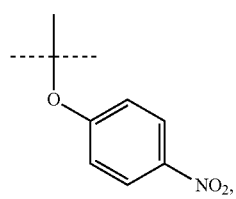  (f-ii)

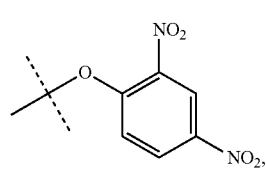  (f-iii)

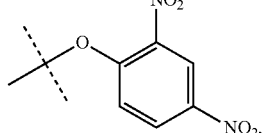

-continued (f-iv)

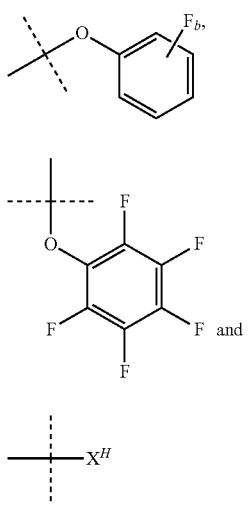

(f-v)

(f-vi)

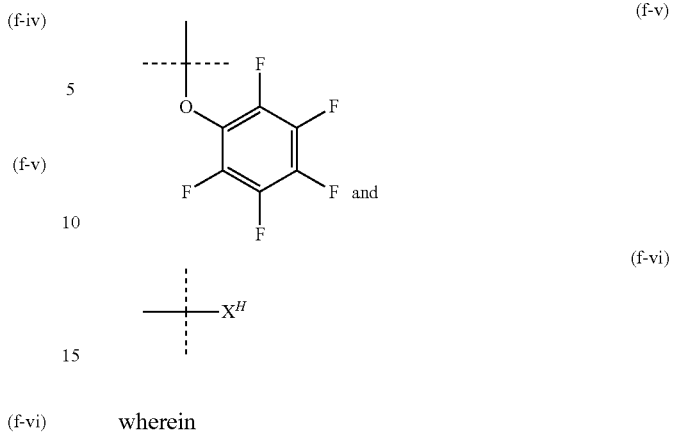

wherein the dashed lines indicate attachment to the rest of the molecule, b is 1, 2, 3 or 4, $X^H$ is Cl, Br, I, or F.

In another preferred embodiment $A^{x0}$ of step (A) is a carboxylic acid (—(C═O)OH) and $A^{x1}$ of step (B) is a primary amine or secondary amine.

In another preferred embodiment $A^{x0}$ of step (A) is a maleimide and $A^{x1}$ of step (B) is a thiol.

More preferably, $A^{x0}$ of step (A) is an amine and $A^{x1}$ of step (B) is $Y^1$—(C═O)—, $Y^1$—(C═O)—NH—, or $Y^1$—(C═O)—O— and most preferably $A^{x0}$ of step (A) is an amine and $A^{x1}$ of step (B) is $Y^1$—(C═O)—.

$A^{x1}$ of step (B) may optionally be present in protected form.

Suitable activating reagents to obtain the activated carboxylic acid are for example N,N'-dicyclohexyl-carbodiimide (DCC), 1-ethyl-3-carbodiimide (EDC), benzotriazol-1-yl-oxytripyrrolidinophosphonium hexafluorophosphate (PyBOP), bromotripyrrolidinophosphonium hexafluorophosphate (PyBrOP), 1-cyano-2-ethoxy-2-oxoethylidenaminooxy)dimethylamino-morpholino-carbenium hexafluorophosphate (COMU), 1-hydroxybenzotriazole (HOBT), 1-hydroxy-7-azabenzotriazole (HOAT), O-(6-chlorobenzotriazol-1-yl)-N,N,N',N'-tetramethyluronium hexafluorophosphate (HCTU), 1-H-benzotriazolium (HBTU), (O-(7-azabenzotriazol-1-yl)-N,N,N',N'-tetramethyluronium hexafluorophosphate (HATU), and O-(benzotriazol-1-yl)-N,N,N',N'-tetramethyluronium tetrafluoroborate (TBTU). These reagents are commercially available and well-known to the skilled person.

Preferably, $A^{x2}$ of step (B) is selected from the group consisting of -maleimide, —SH, —NH$_2$, —SeH, —N$_3$, —C≡CH, —CR═CR$^{1a}$R$^{1b}$, —OH, —(CH═X)—R$^1$, —(C═O)—S—R$^1$, —(C═O)—H, —NH—NH$_2$, —O—NH$_2$, —Ar—X$^0$, —Ar—Sn(R$^1$)(R$^{1a}$)(R$^{1b}$), —Ar—B(OH)(OH), Br, I, Y$^1$—(C═O)—, Y$^1$—(C═O)—NH—, Y$^1$—(C═O)—O—, wherein the dashed lines indicate attachment to the rest of the molecule, b is 1, 2, 3 or 4, $X^H$ is Cl, Br, I, or F.

In another preferred embodiment $A^{x0}$ of step (A) is a hydroxyl group (—OH) and $A^{x1}$ of step (B) is O═C═N—, I—, Br—, SCN—, or $Y^1$—(C═O)—NH—, wherein $Y^1$ is selected from formulas (f-i) to (f-vi):

(f-i)

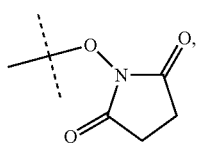

(f-ii)

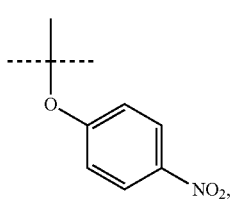

(f-iii)

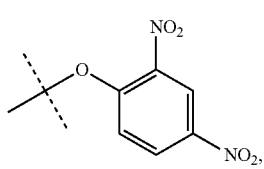

(f-iv)

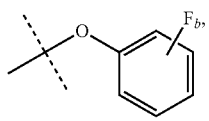

-continued with optional protecting groups;
wherein
dashed lines indicate attachment to SP²;
X is O, S, or NH,
$X^0$ is —OH, —$NR^1R^{1a}$, —SH, or —SeH,
$X^H$ is Cl, Br, I or F;
Ar is phenyl, naphthyl, indenyl, indanyl, or tetralinyl;
$R^1$, $R^{1a}$, $R^{1b}$ are independently of each other H, $C_{1-6}$ alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, or tetralinyl; and
$Y^1$ is selected from formulas (f-i) to (f-vi):

(f-i)

(f-ii)

(f-iii)

(f-iv)

-continued (f-v)

(f-vi)

wherein
the dashed lines indicate attachment to the rest of the molecule,
b is 1, 2, 3 or 4,
$X^H$ is Cl, Br, I, or F.

More preferably, $A^{x2}$ of step (B) is —$NH_2$, maleimide or thiol and most preferably $A^{x2}$ of step (B) is maleimide. Equally preferably, $A^{x2}$ of step (B) is thiol.

$A^{x2}$ of step (B) may optionally be present in protected form.

If the hydrogel of step (A) is covalently conjugated to a spacer moiety, the resulting hydrogel-spacer moiety conjugate is of formula (VIII):

$$\text{---}A^{y1}\text{---}SP^2\text{---}A^{x2},$$ (VIII)

wherein
the dashed line indicates attachment to the hydrogel of step (A);
$A^{y1}$ is the linkage formed between $A^{x0}$ and $A^{x1}$; and
$SP^2$ and $A^{x2}$ are used as in formula (VI).

Preferably, $A^{y1}$ of formula (VIII) is a stable linkage.

Preferably, $A^{y1}$ of formula (VIII) is selected from the group consisting of wherein
dashed lines marked with an asterisk indicate attachment to the hydrogel; and
unmarked dashed lines indicate attachment to SP².

Suitable reaction conditions are described in the Examples sections and are known to the person skilled in the art.

Process step (B) may be carried out in the presence of a base. Suitable bases include customary inorganic or organic bases. These preferably include alkaline earth metal or alkali metal hydrides, hydroxides, amides, alkoxides, acetates, carbonates or bicarbonates such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN), N,N-diisopropylethylamine (DIPEA), diazabicycloundecene (DBU) or collidine.

Process step (B) may be carried out in the presence of a solvent. Suitable solvents for carrying out the process step (B) of the invention include organic solvents. These preferably include water and aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, dimethylether, diethylene glycol; acetonitrile, N-methyl-2-pyrrolidone (NMP), dimethylformamide (DMF), dimethyl sulfoxide (DMSO), N,N-dimethylacetamide, nitromethane, nitrobenzene, hexamethylphosphoramide (HMPT), 1,3-dimethyl-2-imidazolidinone (DMI), 1,3-dimethyl-3,4,5,6-tetrahydro-2(1H)-pyrimidinone (DMPU), ethyl acetate, acetone, butanone; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; or mixtures thereof. Preferably, the solvent is selected from the group consisting of water, acetonitrile and N-methyl-2-pyrrolidone.

Preferably, $A^{x3}$ of step (C) is selected from the group consisting of —SH, —$NH_2$, —SeH, -maleimide, —C≡CH, —$N_3$, —CR=$CR^{1a}R^{1b}$, —(C=X)—$R^1$, —OH, —(C=O)—S—$R^1$, —NH—$NH_2$, —O—$NH_2$, —Ar—Sn$(R^1)(R^{1a})(R^{1b})$, —Ar—B(OH)(OH), —Ar—$X^0$,

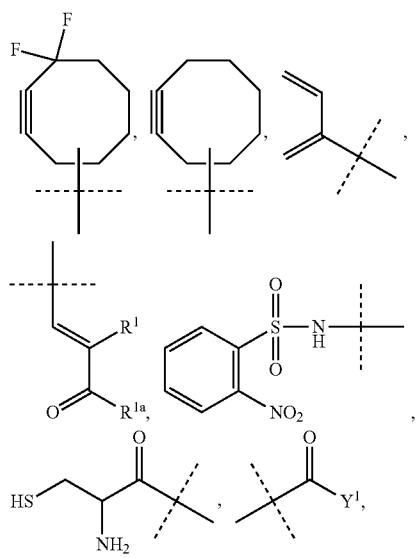

-continued

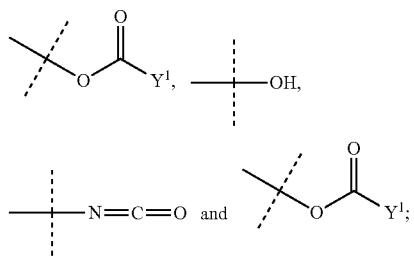

wherein dashed lines indicate attachment to Z;

X is O, S, or NH, $X^0$ is —OH, —$NR^1R^{1a}$, —SH, or —SeH;

$R^1$, $R^{1a}$, $R^{1b}$ are independently of each other H, $C_{1-6}$ alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, or tetralinyl; and Ar is phenyl, naphthyl, indenyl, indanyl, or tetralinyl.

$Y^1$ is an activated carboxylic acid, activated carbonate or activated carbamate, preferably $Y^1$ is selected from formulas (f-i) to (f-vi):

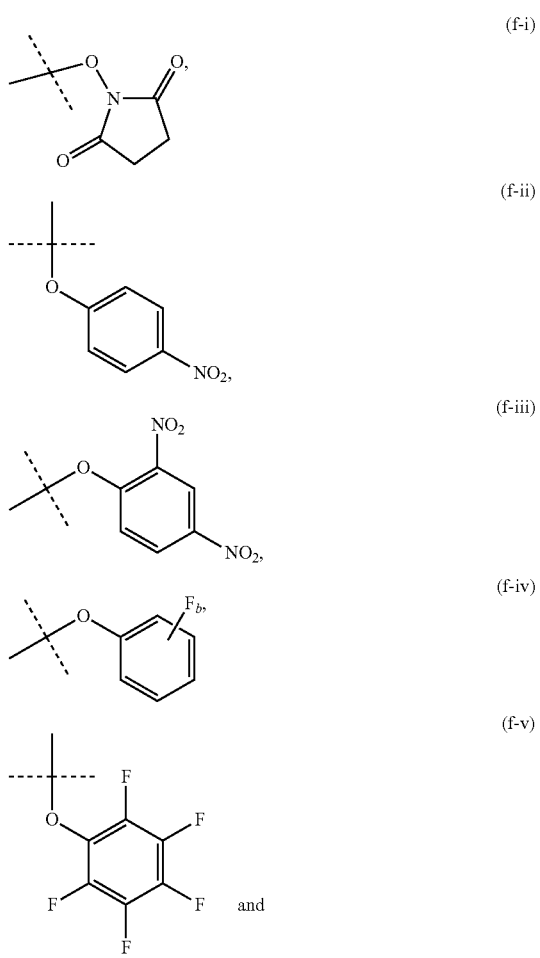

-continued

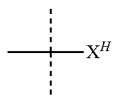
(f-vi)

wherein
the dashed lines indicate attachment to the rest of the molecule,
b is 1, 2, 3 or 4,
$X^H$ is Cl, Br, I, or F In a preferred embodiment, $Y^1$ is selected from formulas (f-i) to (f-vi):

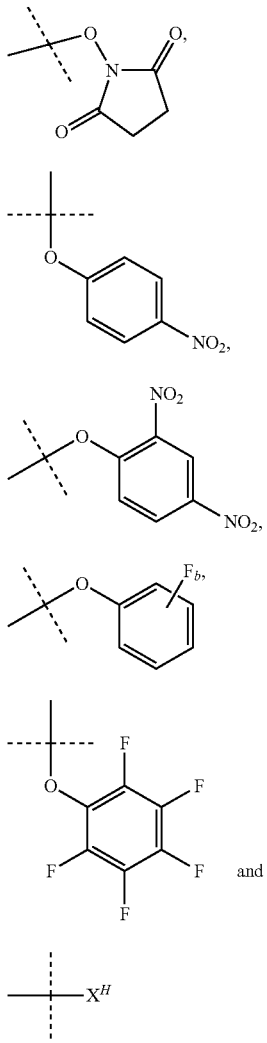

wherein
the dashed lines, b and $X^H$ are used as above.

More preferably, $A^{x3}$ of step (C) is —SH or -maleimide and most preferably $A^{x3}$ of step (C) is —SH.

In another preferred embodiment $A^{x3}$ of step (C) is of formula (aI)

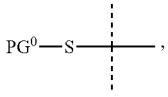
(aI)

wherein
the dashed line indicates attachment to Z of formula (VII);
$PG^0$ is a sulfur-activating moiety; and
S is sulfur;

Preferably, $PG^0$ of formula (aI) is selected from the group consisting of

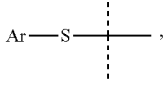
(i)

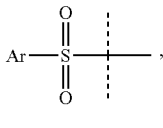
(ii)

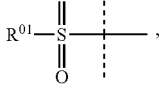
(iii)

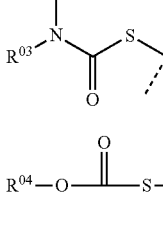
(iv)

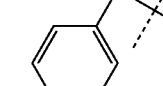
(v)

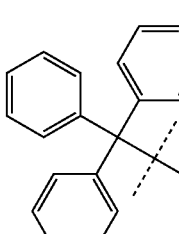
(vi)
, and

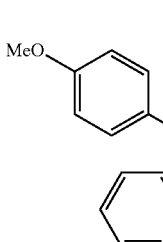
(vii)
;

wherein
the dashed lines indicate attachment to the sulfur of formula (aI);
Ar is an aromatic moiety which is optionally further substituted;
$R^{01}$, $R^{02}$, $R^{03}$, $R^{04}$ are independently of each other —H; $C_{1-50}$ alkyl; $C_{2-50}$ alkenyl; or $C_{2-50}$ alkynyl, wherein $C_{1-50}$ alkyl; $C_{2-50}$ alkenyl; and $C_{2-50}$ alkynyl are optionally substituted with one or more $R^3$, which are the same or different and wherein $C_{1-50}$ alkyl; $C_{2-50}$ alkenyl; and $C_{2-50}$ alkynyl are optionally interrupted by one or more groups selected from the group consisting of -Q-, —C(O)O—; —O—; —C(O)—; —C(O)N($R^4$)—; —S(O)$_2$N($R^4$)—; —S(O)N($R^4$)—; —S(O)$_2$—; —S(O)—; —N($R^4$)S(O)$_2$N($R^{4a}$)—; —S—; —N($R^4$)—; —OC(O)$R^4$; —N($R^4$)C(O)—; —N($R^4$)S(O)$_2$—; —N($R^4$)S(O)—; —N($R^4$)C(O)O—; —N($R^4$)C(O)N($R^{4a}$)—; and —OC(O)N($R^4R^{4a}$);

Q is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl, wherein T is optionally substituted with one or more $R^3$, which are the same or different;

$R^3$ is halogen; —CN; oxo (=O); —COO$R^5$; —O$R^5$; —C(O)$R^5$; —C(O)N($R^5R^{5a}$); —S(O)$_2$N($R^5R^{5a}$); —S(O)N($R^5R^{5a}$); —S(O)$_2R^5$; —S(O)$R^5$; —N($R^5$)S(O)$_2$N($R^5R^{5b}$); —S$R^5$; —N($R^5R^{5a}$); —NO$_2$; —OC(O)$R^5$; —N($R^5$)C(O)$R^{5a}$; —N($R^5$)S(O)$_2R^{5a}$; —N($R^5$)S(O)$R^{5a}$; —N($R^5$)C(O)O$R^{5a}$; —N($R^5$)C(O)N($R^{5a}R^{5b}$); —OC(O)N($R^5R^{5a}$); or $C_{1-6}$ alkyl, wherein $C_{1-6}$ alkyl is optionally substituted with one or more halogen, which are the same or different; and $R^4$, $R^{4a}$, $R^5$, $R^{5a}$, $R^{5b}$ are independently selected from the group consisting of —H; or $C_{1-6}$ alkyl, wherein $C_{1-6}$ alkyl is optionally substituted with one or more halogen, which are the same or different.

Preferably, $R^{01}$, $R^{03}$ and $R^{04}$ are independently of each other $C_{1-6}$ alkyl.

Preferably, $R^{02}$ is selected from H and $C_{1-6}$ alkyl.

Preferably, Ar is selected from the group consisting of

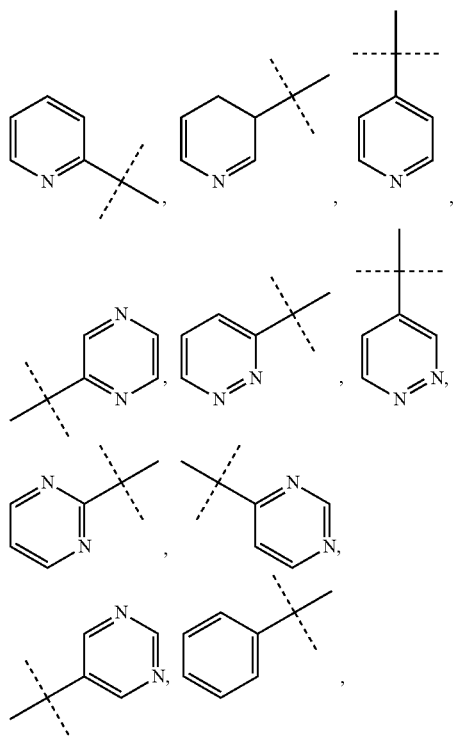

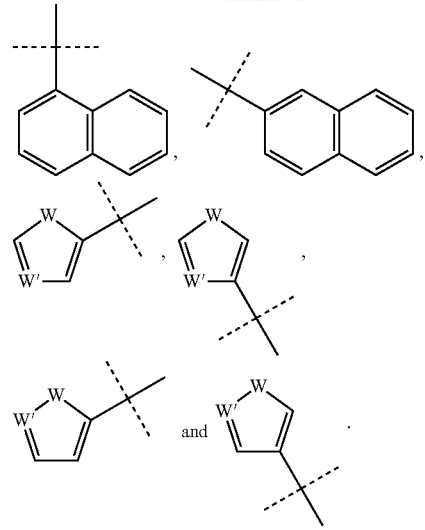

wherein dashed lines indicate attachment to the rest of $PG^0$ of formula (aI);

W is independently of each other O, S, or N;

W' is N; and wherein Ar is optionally substituted with one or more substituent(s) independently selected from the group consisting of NO$_2$, Cl and F.

More preferably, $PG^0$ of formula (aI) is selected from the group consisting of

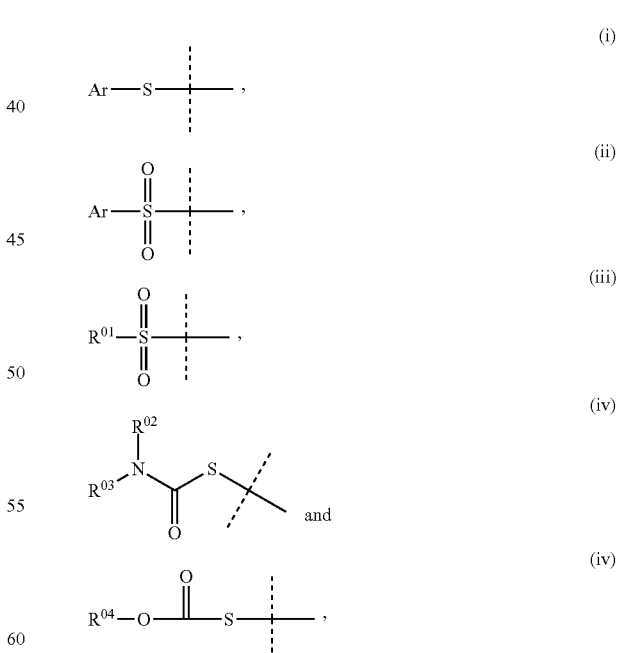

wherein the dashed lines indicate attachment to the sulfur of formula (aI); and

Ar, $R^{01}$, $R^{02}$, $R^{03}$ and $R^{04}$ are used as above.

More preferably, PG⁰ of formula (aI) is

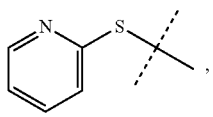, wherein the dashed line indicates attachment to the sulfur of formula (aI).

$A^{x3}$ of step (C) may optionally be present in protected form.

Preferred combinations of $A^{x2}$ of step (B) and $A^{x3}$ of step (C) are the following:

| $A^{x2}$ | $A^{x3}$ |
|---|---|
| -maleimide | HS—, H₂N—, or HSe— |
| —SH, —NH₂, or —SeH | maleimide- |
| —NH₂ | $Y^1$—(C=O)—, |
|  | $Y^1$—(C=O)—NH—, or |
|  | $Y^1$—(C=O)—O— |
| —N₃ | HC≡C—, |
| —C≡CH, | 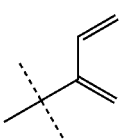 |
| 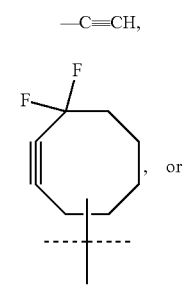 | N₃— |
| 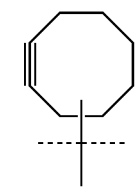 | $R^{1b}R^{1a}C=CR^1$— or |
| —$CR^{1a}=CR^{1a}R^{1b}$ | |

-continued

| $A^{x2}$ | $A^{x3}$ |
|---|---|
|  | 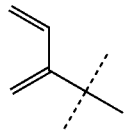 |
| 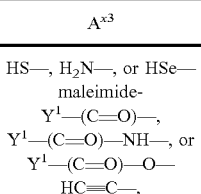 | $R^{1b}R^{1a}C=CR^1$— |
| —(C=X)—$R^1$ | |
| 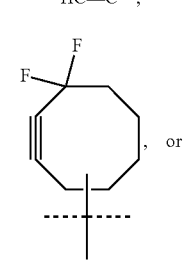 | |
|  | 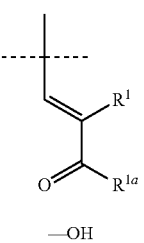 |
|  | $R^1$—(C=X)— |
| —OH | H₂N— or |
|  | 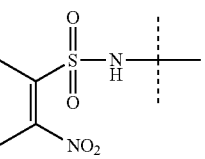 |
| —NH₂ or | HO— |
| 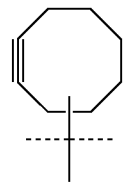 | |
| —(C=O)—S—$R^1$ | |
|  | 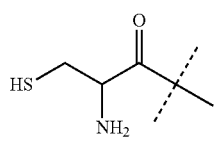 |

| $A^{x2}$ | $A^{x3}$ |
|---|---|
| 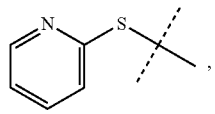 | $R^1$—S—(C=O)— |
| —(C=O)—H<br>—NH—NH$_2$ or —O—NH$_2$<br>—Ar—X$^0$<br>(R$^{1b}$)(R$^{1a}$)(R$^1$)Sn—Ar— or<br>—Ar—B(OH)(OH) | H$_2$N—NH— or H$_2$N—O—<br>H—(C=O)—<br>—Ar—Sn(R$^1$)(R$^{1a}$)(R$^{1b}$) or<br>—Ar—B(OH)(OH)<br>X$^0$—Ar— | wherein

X is O, S, or NH;

X$^0$ is —OH, —NR$^1$R$^{1a}$, —SH, or —SeH;

R$^1$, R$^{1a}$, R$^{1b}$ are independently of each other selected from the group consisting of H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, and tetralinyl; and Ar is phenyl, naphthyl, indenyl, indanyl, or tetralinyl.

In another preferred embodiment $A^{x2}$ is —SH and $A^{x3}$ is of formula (aI), wherein PG$^0$ is of formula (i), (ii), (iii), (iv), (v), (vi) or (viii). More preferably, PG$^0$ of formula (aI) is of formula (i), (ii), (iii), (iv) or (v) and even more preferably, PG$^0$ of formula (aI) is of formula (i). Most preferably, PG$^0$ of formula (aI) is of formula

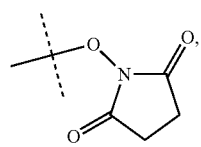

wherein the dashed line indicates attachment to the sulfur of formula (aI).

In one preferred embodiment, $A^{x2}$ of step (B) is an amine and $A^{x3}$ of step (C) is Y$^1$—(C=O)—, Y$^1$—(C=O)—NH—, or Y$^1$—(C=O)—O— and most preferably $A^{x2}$ of step (B) is an amine and $A^{x3}$ of step (C) is Y$^1$—(C=O)—.

In another preferred embodiment $A^{x2}$ of step (B) is maleimide and $A^{x3}$ of step (C) is —SH.

In one embodiment the optional step (B) is omitted, $A^{x0}$ of step (A) is an amine and $A^{x3}$ of step (C) is ClSO$_2$—, R$^1$(C=O)—, I—, Br—, Cl—, SCN—, CN—, O=C=N—, Y$^1$—(C=O)—, Y$^1$—(C=O)—NH—, or Y$^1$—(C=O)—O—, wherein R$^1$ is H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, or tetralinyl; and Y$^1$ is selected from formulas (f-i) to (f-vi):

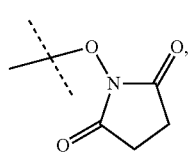 (f-i)

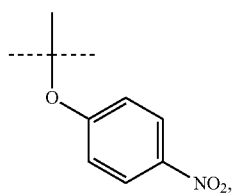 (f-ii)

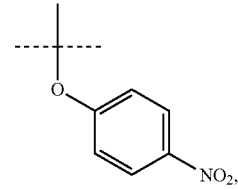 (f-ii)

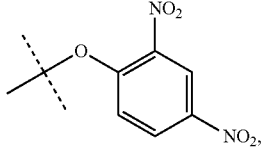 (f-iii)

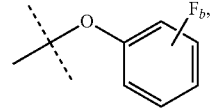 (f-iv)

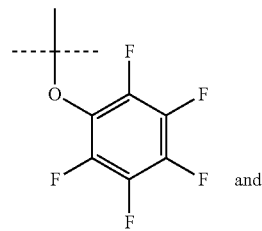 (f-v) and

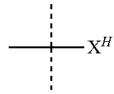 (f-vi)

wherein the dashed lines indicate attachment to the rest of the molecule, b is 1, 2, 3 or 4, X$^H$ is Cl, Br, I, or F.

In another embodiment the optional step (B) is omitted, $A^{x0}$ of step (A) is a hydroxyl group (—OH) and $A^{x3}$ of step (C) is O=C=N—, I—, Br—, SCN—, or Y$^1$—(C=O)—NH—, wherein Y$^1$ is selected from formulas (f-i) to (f-vi):

-continued (f-iii)
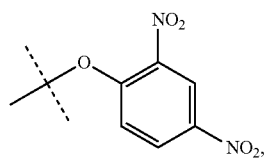

(f-iv)
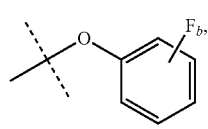

(f-v)
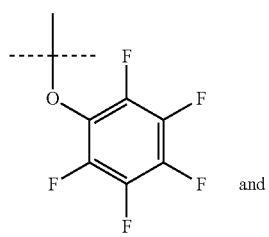 and (f-vi)
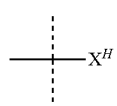

wherein
the dashed lines indicate attachment to the rest of the molecule,
b is 1, 2, 3 or 4,
$X^H$ is Cl, Br, I, or F.

In another embodiment the optional step (B) is omitted, $A^{x0}$ of step (A) is a carboxylic acid (—(C=O)OH) and $A^{x3}$ of step (C) is a primary amine or secondary amine.

In another embodiment the optional step (B) is omitted, $A^{x0}$ of step (A) is an amine and $A^{x3}$ of step (C) is $Y^1$—(C=O)—, $Y^1$—(C=O)—NH—, or Y—(C=O)—O—.

In another embodiment the optional step (B) is omitted, $A^{x0}$ of step (A) is a maleimide and $A^{x3}$ of step (C) is thiol.

In a preferred embodiment the optional step (B) is omitted, $A^{x0}$ of step (A) is an amine and $A^{x3}$ of step (C) is $Y^1$—(C=O)—.

In another preferred embodiment the optional step (B) is omitted, $A^{x0}$ is —SH and $A^{x3}$ is of formula (aI), wherein $PG^0$ is of formula (i), (ii), (iii), (iv), (v), (vi) or (viii). More preferably, $PG^0$ of formula (aI) is of formula (i), (ii), (iii), (iv) or (v) and even more preferably, $PG^0$ of formula (aI) is of formula (i). Most preferably, $PG^0$ of formula (aI) is of formula

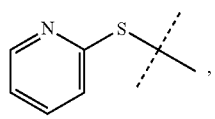

wherein
the dashed line indicates attachment to the sulfur of formula (aI).

The hydrogel obtained from step (C) has the structure of formula (IXa) or (IXb):

(IXa)
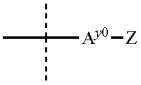

(IXb)
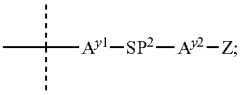

wherein
the dashed line indicates attachment to the hydrogel of step (A);
$A^{y0}$ is the linkage formed between $A^{x0}$ and $A^{x3}$;
$A^{y1}$ is used as in formula (VIII);
$A^{y2}$ is the linkage formed between $A^{x2}$ and $A^{x3}$;
$SP^2$ is used as in formula (VI); and
Z is used as in formula (VII).

Preferably, $A^{y0}$ of step (A) and $A^{y2}$ of formula (IXb) are selected from the group consisting of amide, carbamate,

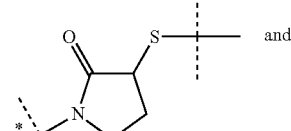 and

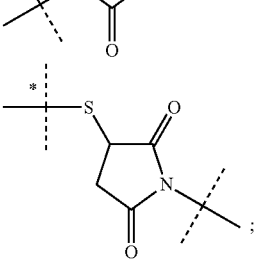;

wherein
the dashed lines marked with an asterisk indicate attachment to the hydrogel or $SP^2$, respectively; and
the unmarked dashed lines indicate attachment to Z of formula (VII).

In one embodiment, Z of step (C) is selected from the group consisting of $C_{1-50}$ alkyl, $C_{2-50}$ alkenyl, $C_{2-50}$ alkynyl, $C_{3-10}$ cycloalkyl, 4- to 7-membered heterocyclyl, 8- to 11-membered heterobicyclyl, phenyl; naphthyl; indenyl; indanyl; and tetralinyl; which $C_{1-50}$ alkyl, $C_{2-50}$ alkenyl, $C_{2-50}$ alkynyl, $C_{3-10}$ cycloalkyl, 4- to 7-membered heterocyclyl, 8- to 11-membered heterobicyclyl, phenyl; naphthyl; indenyl; indanyl; and tetralinyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N($R^9$)—; —S(O)$_2$N($R^9$)—; —S(O)N($R^9$)—; —S(O)$_2$—; —S(O)—; —N($R^9$)S(O)$_2$N($R^{9a}$)—; —S—; —N($R^9$)—; —OC(O)$R^9$; —N($R^9$)C(O)—; —N($R^9$)S(O)$_2$—; —N($R^9$)S(O)—; —N($R^9$)C(O)O—; —N($R^9$)C(O)N($R^{9a}$)—; and —OC(O)N($R^9R^{9a}$);

wherein $R^9$, $R^{9a}$ are independently selected from the group consisting of H; T; $C_{1-50}$ alkyl; $C_{2-50}$ alkenyl; and $C_{2-50}$ alkynyl, which T; $C_{1-50}$ alkyl; $C_{2-50}$ alkenyl; and $C_{2-50}$ alkynyl are optionally substituted with one or more $R^{10}$, which are the same or different and which $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

T is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl, wherein T is optionally substituted with one or more $R^{10}$, which are the same or different;

$R^{10}$ is halogen; CN; oxo (=O); COO$R^{12}$; O$R^{12}$; C(O)$R^{12}$; C(O)N($R^{12}R^{12a}$); S(O)$_2$N($R^{12}R^{12a}$); S(O)N($R^{12}R^{12a}$); S(O)$_2R^{12}$; S(O)$R^{12}$; N($R^{12}$)S(O)$_2$N($R^{12a}R^{12b}$); S$R^{12}$; N($R^{12}R^{12a}$); NO$_2$; OC(O)$R^{12}$; N($R^{12}$)C(O)$R^{12a}$; N($R^{12}$)S(O)$_2R^{12a}$; N($R^{12}$)S(O)$R^{12a}$; N($R^{12}$)C(O)O$R^{12a}$; N($R^{12}$)C(O)N($R^{12a}R^{12b}$); OC(O)N($R^{12}R^{12a}$); or $C_{1-6}$ alkyl, which $C_{1-6}$ alkyl is optionally substituted with one or more halogen, which are the same or different;

$R^{11}$, $R^{11a}$, $R^{12}$, $R^{12a}$, $R^{12b}$ are independently of each other selected from the group consisting of H; and $C_{1-6}$ alkyl, which $C_{1-6}$ alkyl is optionally substituted with one or more halogen, which are the same or different.

In another embodiment Z of step (C) is an inert polymer having a molecular weight ranging from 0.5 kDa to 1000 kDa, preferably having a molecular weight ranging from 0.5 to 500 kDa, more preferably having a molecular weight ranging from 0.75 to 250 kDa, even more preferably ranging from 1 to 100 kDa, even more preferably ranging from 5 to 60 kDa, even more preferably from 10 to 50 and most preferably Z has a molecular weight of 40 kDa.

Preferably, Z of step (C) is an inert polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(imino carbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment Z of step (C) is an inert linear or branched PEG-based polymer comprising at least 70% PEG or a hyaluronic acid-based polymer comprising at least 70% hyaluronic acid. More preferably, Z of step (C) is an inert linear or branched PEG-based polymer comprising at least 70% PEG, even more preferably comprising at least 80% PEG and most preferably comprising at least 90% PEG.

In another preferred embodiment Z of step (C) is a zwitterionic polymer. Preferably, such zwitterionic polymer comprises poly(amino acids) and/or poly(acrylates).

As used herein, the terms "zwitterion" and "zwitterionic" refer to a neutral molecule or moiety with positive and negative charges at different locations within that molecule or moiety at the same time.

According to Zhang et al. (Nature Biotechnology, 2013, volume 31, number 6, pages 553-557) hydrogels made of zwitterionic polymers resist the foreign body response.

Step (C) comprises reacting the hydrogel of step (A) or step (B) with a reagent of formula (VII) in such manner that no more than 99 mol-% of $A^{x0}$ or $A^{x2}$ react with $A^{x3}$. This can be achieved, for example, by reacting at most 0.99 chemical equivalents of the reagent of formula (VII) relative to $A^{x0}$ or $A^{x2}$ with the hydrogel of step (A) or (B).

In order to prevent the reaction of more than 0.99 chemical equivalents, the reagent of formula (VII) can be used in an amount of at most 0.99 chemical equivalents relative to $A^{x0}$ or $A^{x2}$ or, alternatively, the reaction rate is monitored and the reaction is interrupted when at most 0.99 chemical equivalents relative to $A^{x0}$ or $A^{x2}$ have reacted, especially when more than 0.99 chemical equivalents are used. It is understood that also due to physical constraints, such as steric hindrance, hydrophobic properties or other characteristics of the inert moiety Z, no more than 0.99 chemical equivalents may be capable of reacting with $A^{x0}$ or $A^{x2}$, even if more chemical equivalents are added to the reaction.

Preferably, step (C) comprises reacting the hydrogel of step (A) or step (B) with a reagent of formula (VII) in such manner that no more than 80 mol-% of $A^{x0}$ or $A^{x2}$ react with $A^{x3}$, even more preferably, such that no more than 60 mol-% of $A^{x0}$ or $A^{x2}$ react with $A^{x3}$, even more preferably, such that no more than 40 mol-% of $A^{x0}$ or $A^{x2}$ react with $A^{x3}$, even more preferably, such that no more than 20 mol-% of $A^{x0}$ or $A^{x2}$ react with $A^{x3}$ and most preferably, such that no more than 15 mol-% of $A^{x0}$ or $A^{x2}$ react with $A^{x3}$ This can be achieved, for example, by reacting at most 0.8, 0.6, 0.4, 0.2 or 0.15 chemical equivalents of the reagent of formula (VII) relative to $A^{x0}$ or $A^{x2}$ with the hydrogel of step (A) or (B), respectively.

Methods to prevent the reaction of more chemical equivalents are described above.

Based on the measurements of the amount of substance of $A^{x0}$ of step (A) and after step (C) the amount of substance of reacted $A^{x0}$ can be calculated with equation (1):

$$\text{Amount of substance of reacted } A^{x0} \text{ in mmol/g} = (A^{x0}_1 - A^{x0}_2)/(A^{x0}_2 \times MW_Z + 1), \quad (1)$$

wherein $A^{x0}_1$ is the amount of substance of functional groups $A^{x0}$ of the hydrogel of step (A) in mmol/g;

$A^{x0}_2$ is the amount of substance of functional groups $A^{x0}$ of the hydrogel after step (C) in mmol/g; and $MW_Z$ is the molecular weight of Z in g/mmol.

If the optional spacer reagent was covalently conjugated to the hydrogel of step (A), the calculation of the number of reacted $A^{x2}$ is done accordingly.

The percentage of reacted functional groups $A^{x0}$ relative to the functional groups $A^{x0}$ of the hydrogel of step (A) is calculated according to equation (2):

$$\text{mol-\% of reacted } A^{x0} = 100 \times [(A^{x0}_1 - A^{x0}_2)/(A^{x0}_2 \times MW_Z + 1)]/A^{x0}_1, \qquad (2)$$

wherein the variables are used as above.

In one embodiment Z of step (C) is conjugated to the surface of the hydrogel. This can be achieved by selecting the size and structure of the reagent $A^{x3}$-Z such that it is too large to enter the pores or network of the hydrogel. Accordingly, the minimal size of $A^{x3}$-Z depends on the properties of the hydrogel. The person skilled in the art however knows methods how to test whether a reagent $A^{x3}$-Z is capable of entering into the hydrogel using standard experimentation, for example by using size exclusion chromatography with the hydrogel as stationary phase.

A biologically active moiety is connected to the hydrogel of the polymeric prodrug through a reversible prodrug linker. The reversible prodrug linkers of a polymeric prodrug may be the same or different. Preferably, the reversible prodrug linkers of the polymeric prodrug are the same.

A suitable reversible prodrug linker moiety may be chosen depending on the one or more functional groups present in the corresponding drug of a biologically active moiety. Suitable reversible prodrug linker moieties are known to the person skilled in the art and preferred examples are given in the following sections.

In a preferred embodiment, the reversible prodrug linker moiety connecting the polymeric carrier to a biologically active moiety is a traceless prodrug linker. Preferably, all reversible prodrug linker moieties of the polymeric prodrug are traceless prodrug linkers.

A preferred reversible prodrug linker moiety for amine-comprising drugs is described in WO-A 2005/099768. Therefore, the following sub-structures selected from the general formulas (II) and (III) are preferred embodiments for reversible prodrug linker-biologically active moiety conjugates:

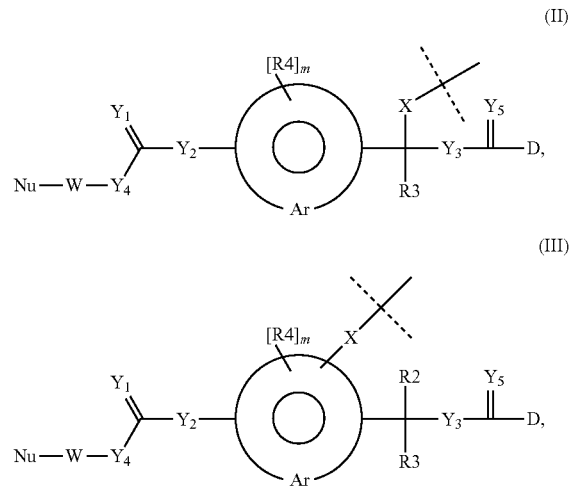

wherein the dashed line indicates attachment to the polymeric carrier or to a spacer moiety which is connected to the polymeric carrier, and wherein X, $Y_1$, $Y_2$, $Y_3$, $Y_4$, $Y_5$, R2, R3, R4, Nu, W, m, and D of formulas (II) and (III) have the following meaning:

D is an amine-comprising biologically active moiety which is attached to the rest of the sub-structure shown in formula (II) or (III) by forming a —O—(C=O)—N—; —O—(C=S)—N—; —S—(C=O)—N—; or —S—(C=S)—N— linkage;

X is a spacer moiety R5-Y6;

$Y_1$ and $Y_2$ are each independently O, S or NR6;

$Y_3$ is O or S;

$Y_4$ is O, NR6, or —C(R7)(R8)-;

$Y_5$ is O or S;

Y6 is O, S, NR6, succinimide, maleimide, unsaturated carbon-carbon bonds or any heteroatom containing a free electron pair or is absent;

R2 and R3 are independently selected from the group consisting of hydrogen, substituted or unsubstituted linear, branched or cyclical alkyl or heteroalkyl groups, aryls, substituted aryls, substituted or unsubstituted heteroaryls, cyano groups, nitro groups, halogens, carboxy groups, carboxyalkyl groups, alkylcarbonyl groups and carboxamidoalkyl groups;

R4 is selected from the group consisting of hydrogen, substituted or unsubstituted linear, branched or cyclical alkyls or heteroalkyls, aryls, substituted aryls, substituted or unsubstituted heteroaryl, substituted or unsubstituted linear, branched or cyclical alkoxys, substituted or unsubstituted linear, branched or cyclical heteroalkyloxys, aryloxys or heteroaryloxys, cyano groups and halogens;

R5 is selected from substituted or non-substituted linear, branched or cyclical alkyl or heteroalkyl, aryls, substituted aryls, substituted or non-substituted heteroaryls;

R6 is selected from hydrogen, substituted or unsubstituted linear, branched or cyclical alkyls or heteroalkyls, aryls, substituted aryls and substituted or unsubstituted heteroaryls;

R7 and R8 are each independently selected from the group consisting of hydrogen, substituted or unsubstituted linear, branched or cyclical alkyls or heteroalkyls, aryls, substituted aryls, substituted or unsubstituted heteroaryls, carboxyalkyl groups, alkylcarbonyl groups, carboxamidoalkyl groups, cyano groups, and halogens;

W is selected from substituted or unsubstituted linear, branched or cyclical alkyls, aryls, substituted aryls, substituted or unsubstituted linear, branched or cyclical heteroalkyls, substituted or unsubstituted heteroaryls;

Nu is a nucleophile;

m is 0, 1, 2, 3, 4, 5, or 6, and

Ar is a multi-substituted aromatic hydrocarbon or multi-substituted aromatic heterocycle.

Optionally, the reversible prodrug linker-biologically active moiety conjugates of formula (II) or (III) is further substituted.

Preferably, Nu of formulas (II) and (III) is selected from the group comprising primary, secondary and tertiary amine; thiol; carboxylic acid; hydroxylamine; hydrazine; and nitrogen containing heteroaryl.

Preferably, Ar of formulas (II) and (III) is selected from one of the following structures:

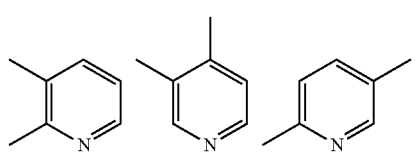

-continued

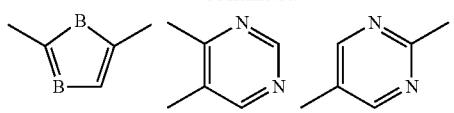

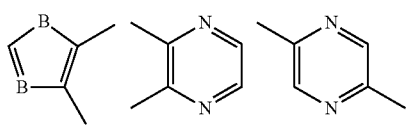

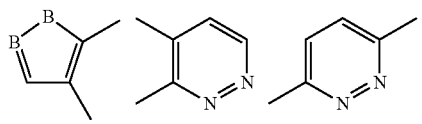

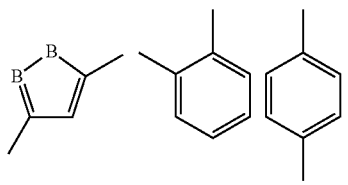

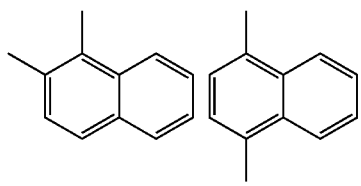

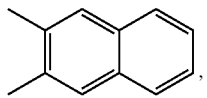

wherein each B is independently selected from O, S, N.

Preferably, R2, R3, R4, R5, R6, R7, R8 and W of formulas (II) and (III) are independently selected from hydrogen, methyl, ethyl, ethoxy, methoxy, and other $C_{1-6}$ linear, cyclical or branched alkyls and heteroalkyls.

Another suitable reversible prodrug linker moiety for amine-comprising drugs is described in WO-A 2006/136586. Accordingly, the following sub-structures selected from the general formulas (IV), (V) and (VI) are preferred embodiments for reversible prodrug linker-biologically active moiety conjugates:

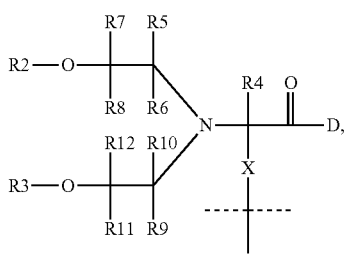

(IV)

-continued

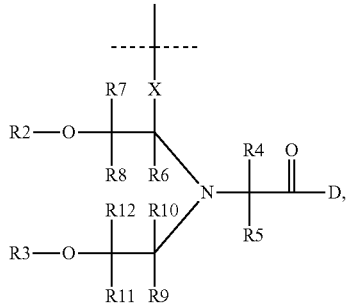

(V)

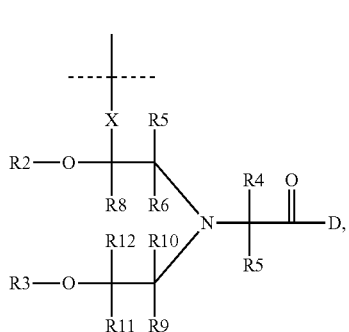

(VI)

wherein the dashed line indicates attachment to the hydrogel or to a spacer moiety which is connected to the hydrogel, and wherein X, R2, R3, R4, R5, R6, R7, R8, R9, R10, R11, R12 and D of formulas (IV), (V) and (VI) have the following meaning:

D is an amine-comprising biologically active moiety;

X is a spacer R13-Y1;

Y1 is O, S, NR6, succinimide, maleimide, an unsaturated carbon-carbon bond, or any heteroatom-containing a free electron pair or Y1 is absent;

R2 and R3 are selected independently from hydrogen, acyl groups, and protecting groups for hydroxyl groups;

R4 to R12 are selected independently from hydrogen, substituted or non-substituted linear, branched or cyclical alkyl or heteroalkyl, aryls, substituted aryls, substituted or non-substituted heteroaryls, cyano, nitro, halogen, carboxy, and carboxamide; and R13 is selected from substituted or non-substituted linear, branched or cyclical alkyl or heteroalkyl, aryls, substituted aryls, substituted or non-substituted heteroaryls.

Optionally, the reversible prodrug linker-biologically active moiety conjugates of formula (IV), (V) or (VI) is further substituted.

Another suitable reversible prodrug linker moiety for primary amine- or secondary amine-comprising drugs is described in WO-A 2009/095479. Accordingly, a preferred polymeric prodrug is given by a prodrug conjugate D-L, wherein D is the primary amine- or secondary amine-comprising biologically active moiety; and L is a non-biologically active linker moiety -$L^1$ represented by formula (VII),

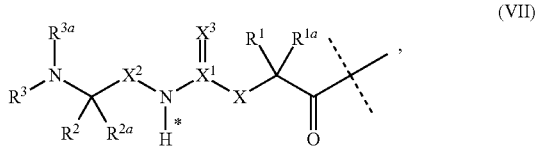

(VII)

wherein the dashed line indicates the attachment to a primary or secondary amino group of an amine-containing biologically active moiety D by forming an amide bond; and wherein X, $X^1$, $X^2$, $R^1$, $R^{1a}$, $R^2$, $R^{2a}$, $R^3$, and $R^{3a}$ of formula (VII) have the following meaning:

X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ is C; or S(O);

$X^2$ is $C(R^7, R^{7a})$; or $C(R^7, R^{7a})$—$C(R^8, R^{8a})$;

$X^3$ is O., S., or N—CN;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl; or optionally, one or more of the pairs $R^{1a}/R^{4a}$, $R^{1a}/R^{5a}$, $R^{4a}/R^{5a}$, $R^{4a}/R^{5a}$, $R^{7a}/R^{8a}$ form a chemical bond;

optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4 to 7 membered heterocyclyl;

optionally, one or more of the pairs $R^1/R^4$, $R^1/R^5$, $R^1/R^6$, $R^4/R^5$, $R^7/R^8$, $R^2/R^3$ are joined together with the atoms to which they are attached to form a ring A;

optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; $C_{3-10}$ cycloalkyl; 4 to 7 membered heterocyclyl; and 9 to 11 membered heterobicyclyl; and wherein L is substituted with one group $L^2$-Z and optionally further substituted, provided that the hydrogen marked with the asterisk in formula (VII) is not replaced by a substituent and preferably provided that $R^3$ and $R^{3a}$ are independently of each other H or are connected to N through an $SP^3$-hybridized carbon atom; and wherein $L^2$ is a single chemical bond or a spacer; and Z is the polymeric carrier of the polymeric prodrug.

Preferably, $X^3$ of formula (VII) is O.

Thus, the polymeric carrier is attached to any one of $R^1$, $R^{1a}$, $R^2$, $R^{2a}$, $R^3$, $R^{3a}$, X, or $X^2$ of formula (VII), either directly (if $L^2$ is a single chemical bond) or through a spacer moiety (if $L^2$ is a spacer).

Optionally, L in formula (VII) is further substituted, provided that the hydrogen marked with the asterisk in formula (VII) is not replaced by a substituent. Preferably, the one or more further optional substituents are independently selected from the group consisting of halogen, CN, $COOR^9$, $OR^9$, $C(O)R^9$, $C(O)N(R^9R^{9a})$, $S(O)_2N(R^9R^{9a})$, $S(O)N(R^9R^{9a})$, $S(O)_2R9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)S(O)_2R^{9a}$, $N(R^9)S(O)R^{9a}$, $N(R^9)C(O)OR^{9a}$, $N(R^9)C(O)N(R^{9a}R^{9b})$, $OC(O)N(R^9R^{9a})$, T, $C_{1-50}$ alkyl, $C_{2-50}$ alkenyl, and $C_{2-50}$ alkynyl, wherein T, $C_{1-50}$ alkyl, $C_{2-50}$ alkenyl, and $C_{2-50}$ alkynyl are optionally substituted with one or more $R^{10}$, which are the same or different, and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

T is selected from the group consisting of phenyl, naphthyl, indenyl, indanyl, tetralinyl, $C_{3-10}$ cycloalkyl, 4- to 7-membered heterocyclyl, and 9- to 11-membered heterobicyclyl, wherein T is optionally substituted with one or more $R^{10}$, which are the same or different, $R^9$, $R^{9a}$, $R^{9b}$ are independently selected from the group consisting of H; T; and $C_{1-50}$ alkyl; $C_{2-50}$ alkenyl; and $C_{2-50}$ alkynyl, $R^{10}$ is halogen, CN, oxo (=O), $COOR^{12}$, $OR^{12}$, $C(O)R^{12}$, $C(O)N(R^{12}R^{12a})$, $S(O)_2N(R^{12}R^{12a})$, $S(O)N(R^{12}R^{12a})$, $S(O)_2 R^{12}$, $S(O)R^{12}$, $N(R^{12})S(O)_2N(R^{12a}R^{12b})$, $SR^{12}$, $N(R^{12}R^{12a})$, $NO_2$, $OC(O)R^{12}$, $N(R^{12})C(O)R^{12a}$, $N(R^{12})S(O)_2R^{12a}$, $N(R^{12})S(O)R^{12a}$, $N(R^{12})C(O)OR^{12a}$, $N(R^{12})C(O)N(R^{12a}R^{12b})$, $OC(O)N(R^{12}R^{12a})$, or $C_{1-6}$ alkyl, wherein $C_{1-6}$ alkyl is optionally substituted with one or more halogen, which are the same or different, $R^{11}$, $R^{11a}$, $R^{12}$, $R^{12a}$, $R^{12b}$ are independently selected from the group consisting of H; or $C_{1-6}$ alkyl, wherein $C_{1-6}$ alkyl is optionally substituted with one or more halogen, which are the same or different.

The term "interrupted" means that between two carbons a group is inserted or at the end of the carbon chain between the carbon and hydrogen.

Preferred moieties $L^1$ according to formula (VII) are selected from the group consisting of:

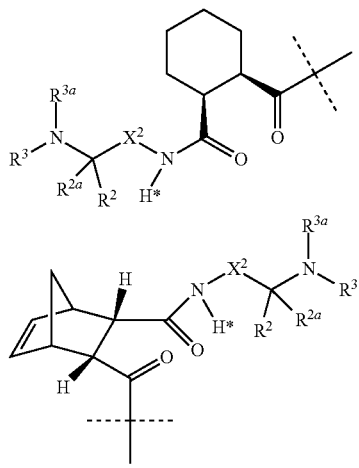

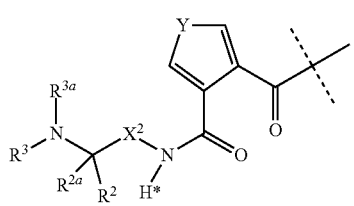

-continued
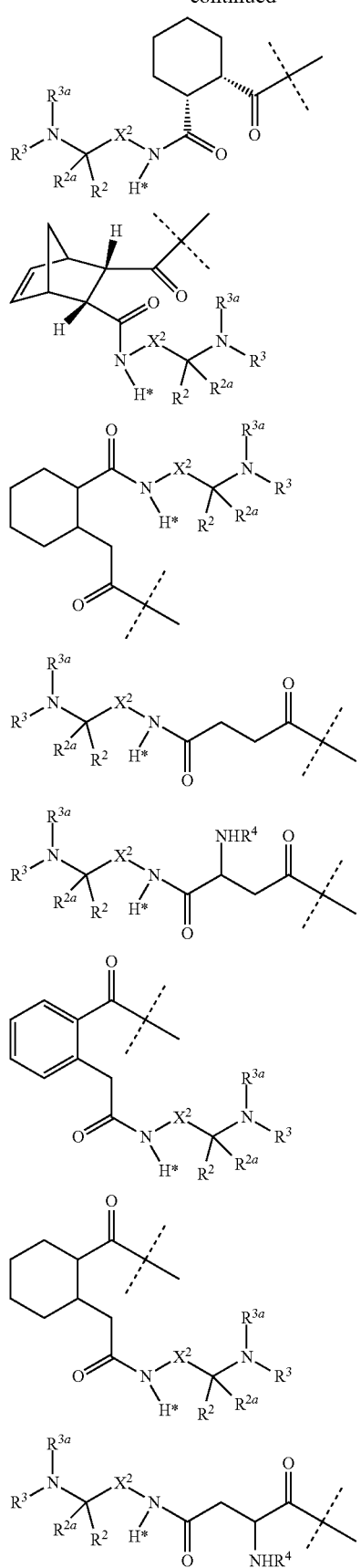
-continued
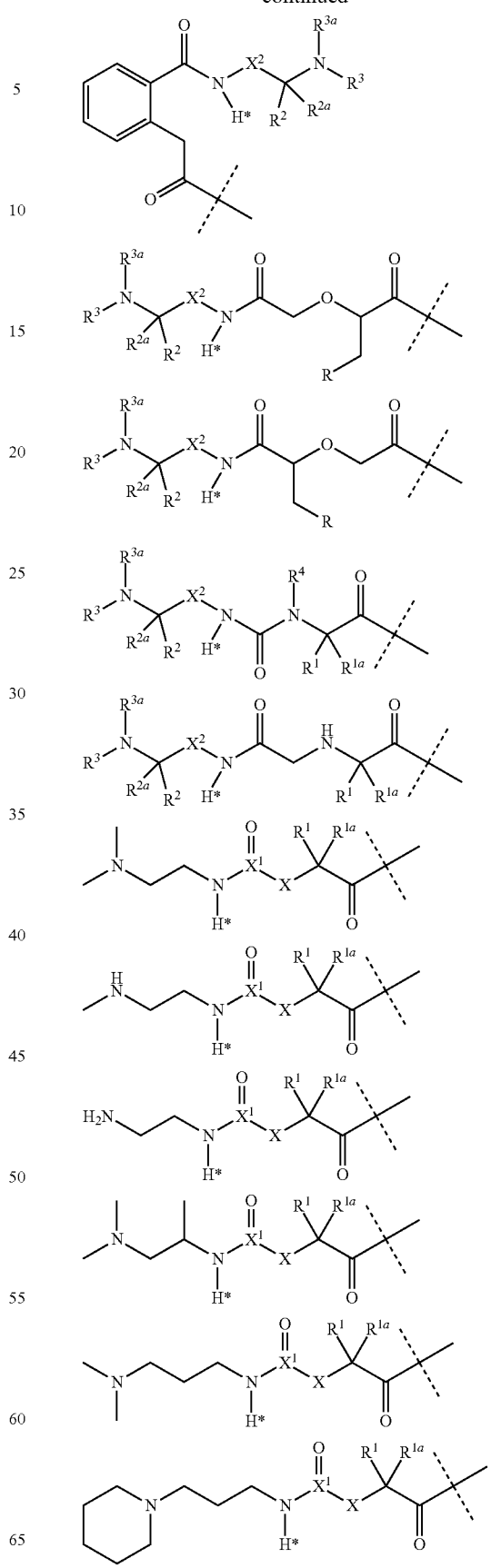

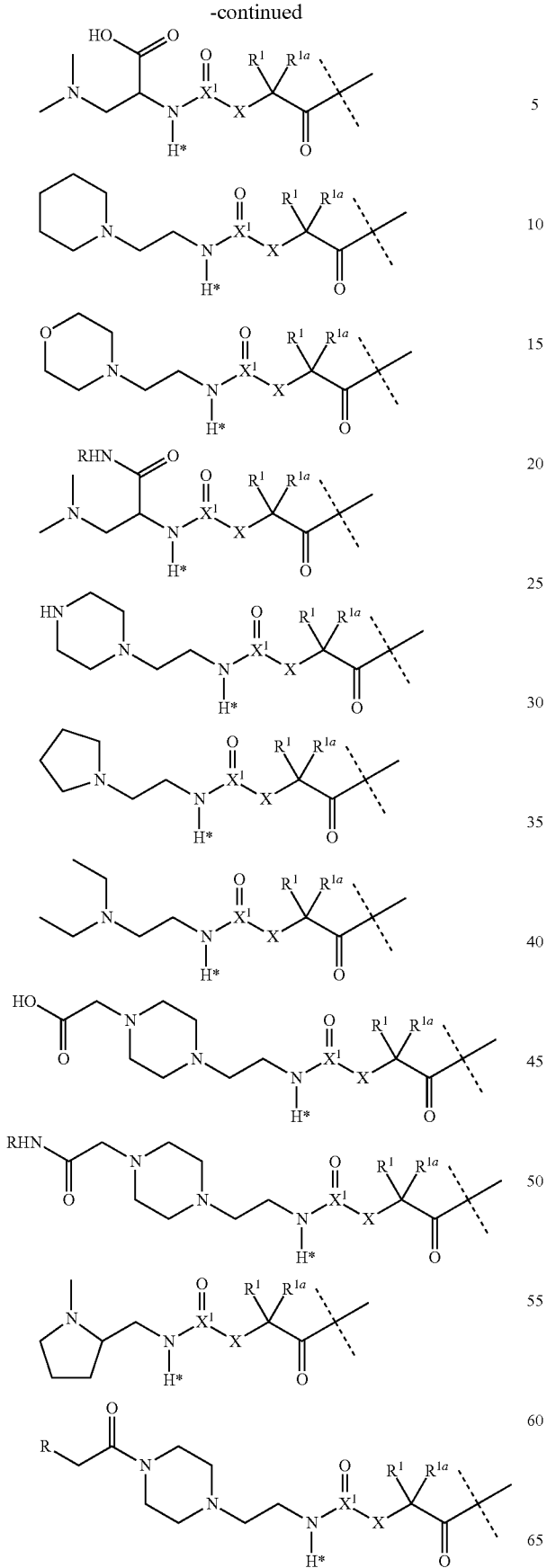
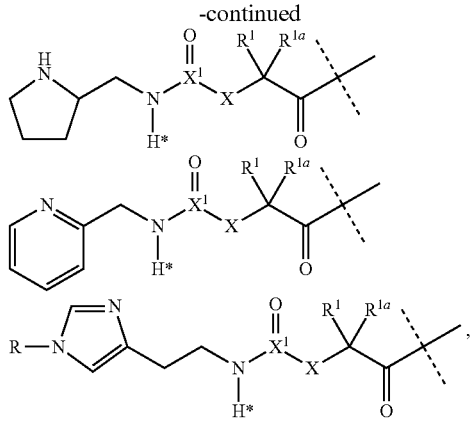
wherein
dashed lines indicate attachment to D of formula (VII);
R is H or $C_{1-4}$ alkyl;
Y is NH, O or S; and
$R^1, R^{1a}, R^2, R^{2a}, R^3, R^{3a}, R^4, X, X^1, X^2$ have the meaning as indicated in formula (VII).
Even more preferred moieties $L^1$ of formula (VII) are selected from the group consisting of:
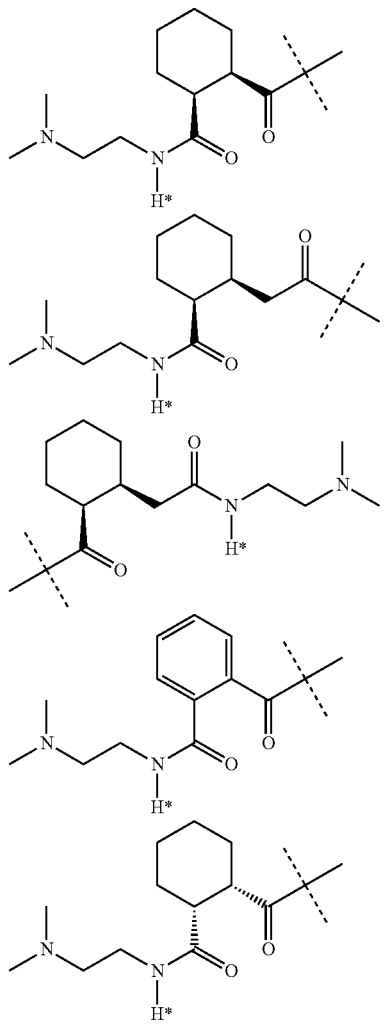

87
-continued
88
-continued
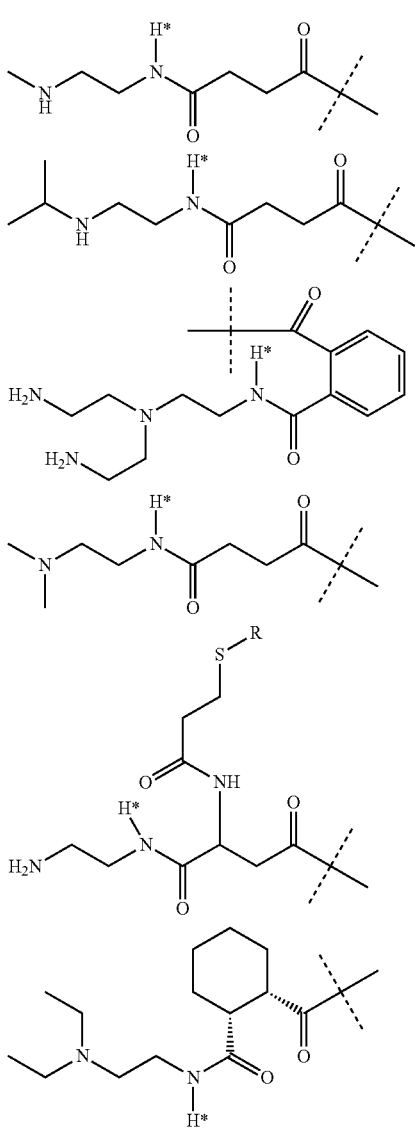
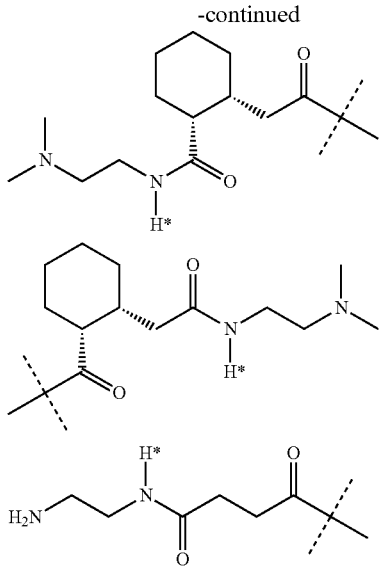
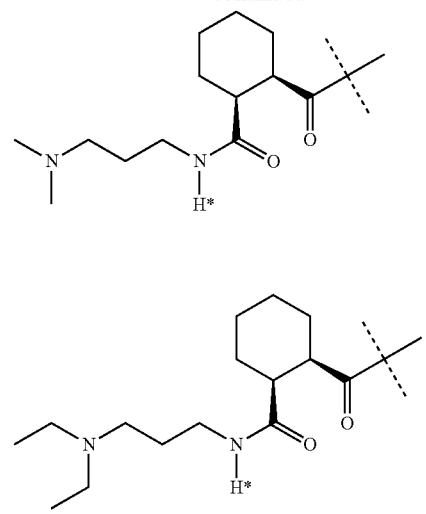

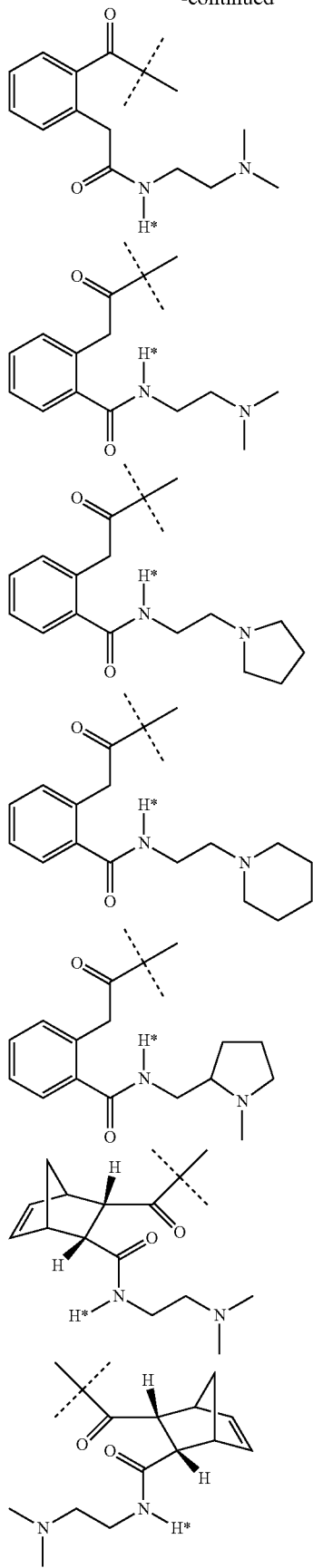
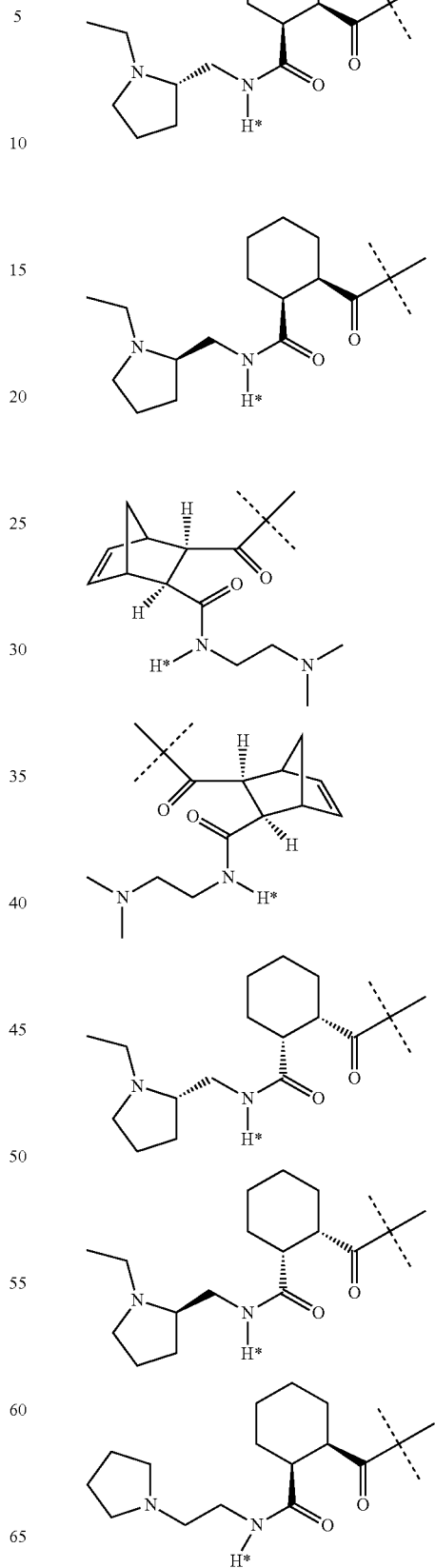

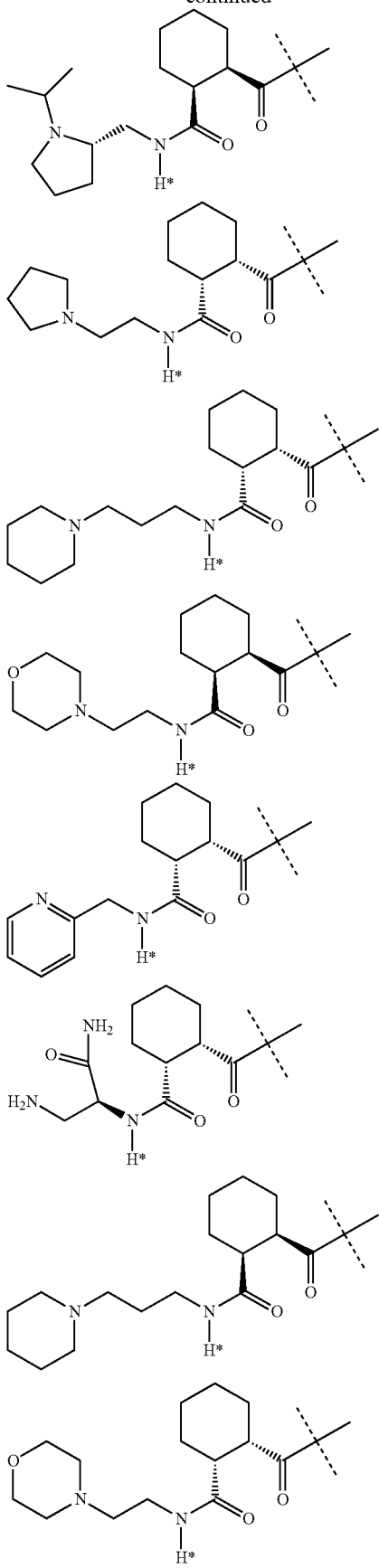
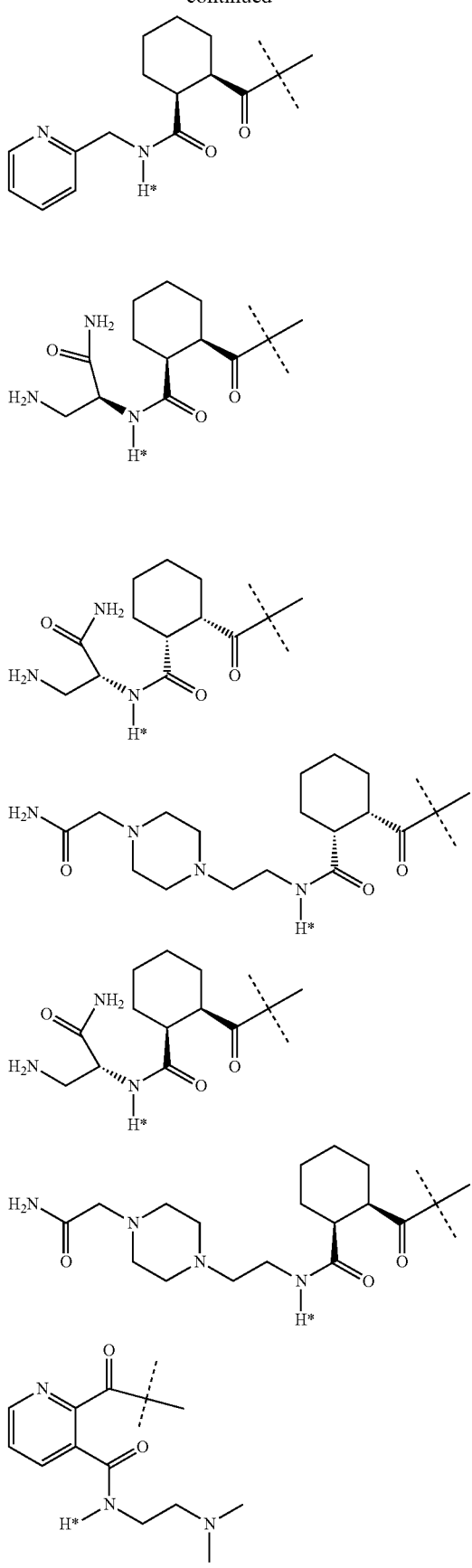

93
-continued
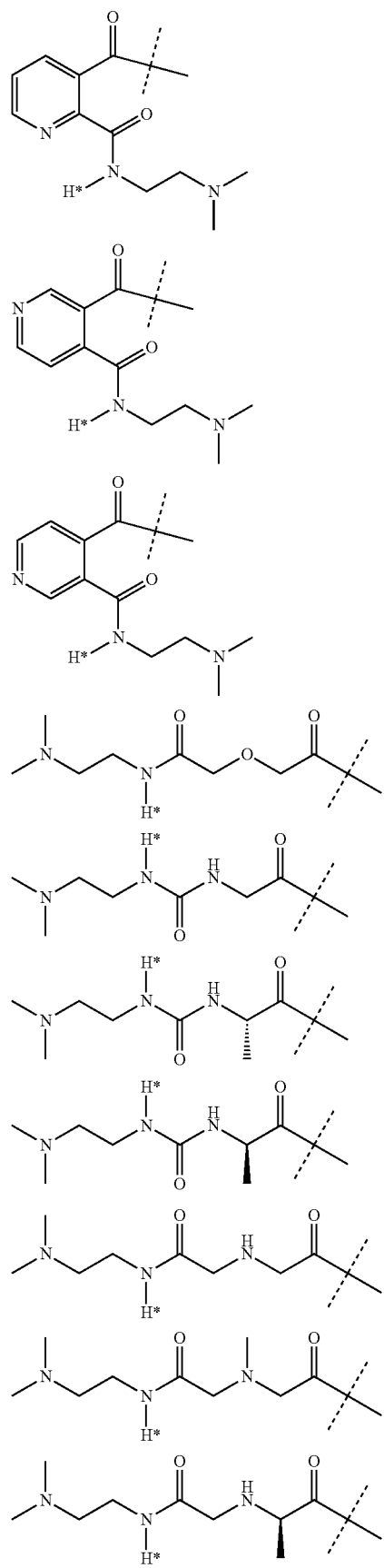
94
-continued
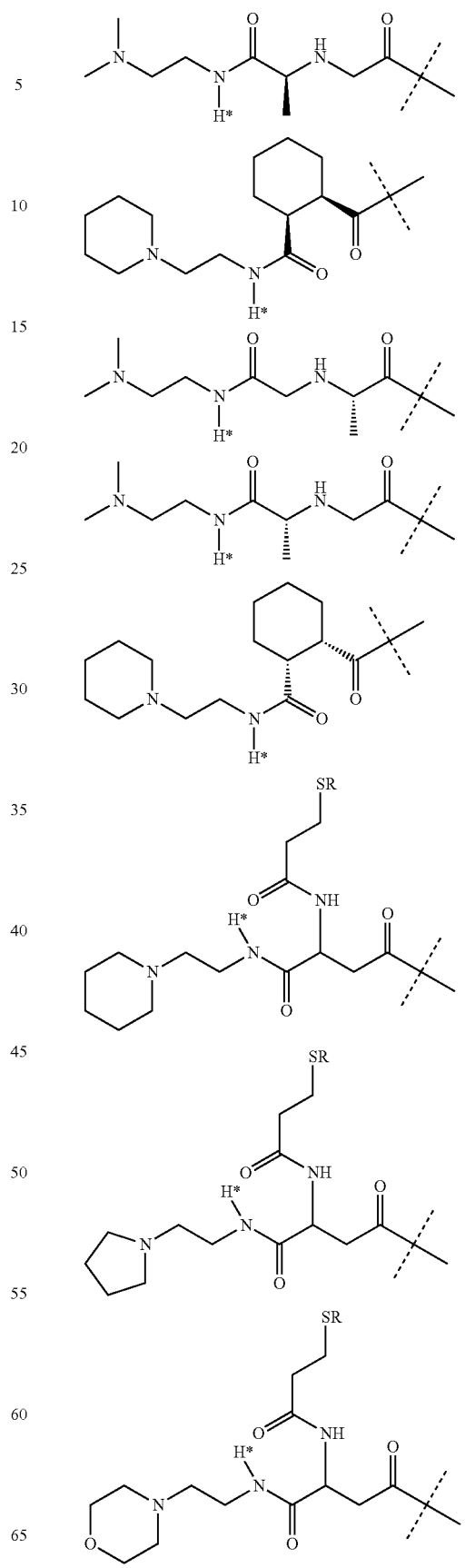

-continued

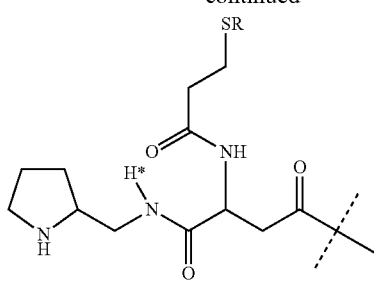
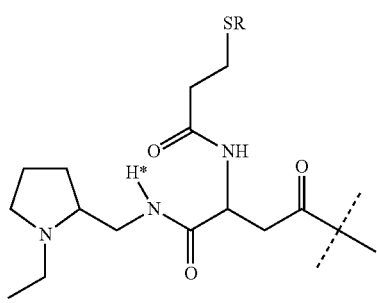
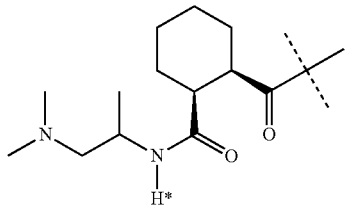
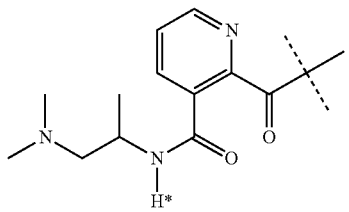
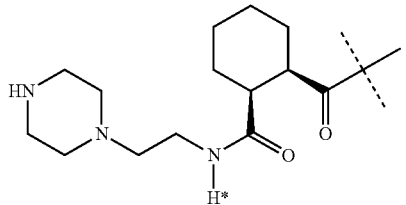
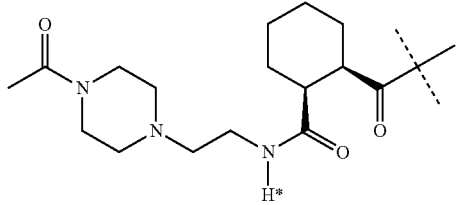
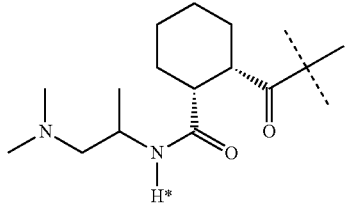

-continued

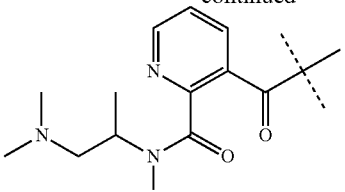
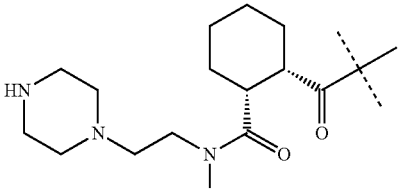
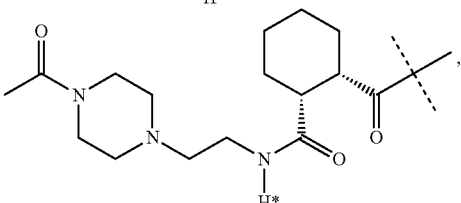

wherein
dashed lines indicate attachment to D of formula (VII), and
R is H or $C_{1-4}$ alkyl.

Another preferred polymeric prodrug is given by a conjugate D-L, wherein
D is the biologically active moiety; and
L is a non-biologically active linker moiety -$L^1$ represented by formula (VIII),

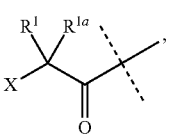

(VIII)

wherein the dashed line indicates attachment to a primary amine- or secondary amine-comprising biologically active moiety D by forming an amide bond; and wherein X, $R^1$, and $R^{1a}$ of formula (VIII) have the following meaning:

X is H or $C_{1-50}$ alkyl, optionally interrupted by one or more groups selected from —NH—, —C($C_{1-4}$ alkyl)-, —O—, —C(O)— or —C(O)NH—;

$R^1$ and $R^{1a}$ are independently selected from the group consisting of H and $C_1$-$C_4$ alkyl;

wherein $L^1$ is substituted with one group $L^2$-Z and optionally further substituted; and wherein $L^2$ is a single chemical bond or a spacer; and Z is the polymeric carrier of the polymeric prodrug.

Thus, the polymeric carrier is attached to any one of $R^1$, $R^{1a}$ or X of formula (VIII), either directly (if $L^2$ is a single chemical bond) or through a spacer moiety (if $L^2$ is a spacer).

Optionally, the sub-structure of formula (VIII) is further substituted.

More preferably, $L^1$ of formula (VIII) comprises one of the fragments of formulas (VIIIb) or (VIIIc), wherein the dashed line marked with an asterisk indicates attachment to D by forming an amide bond with the aromatic amino group of D and the unmarked dashed line indicates attachment to the rest of L1 of formula (VIII) and wherein the structures of formulas (VIIIb) and (VIIIc) are optionally further substituted:

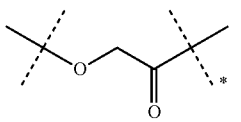
(VIIIb)

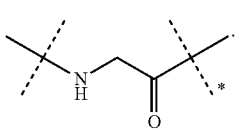
(VIIIc)

More preferably, $L^1$ of formula (VIII) comprises one of the fragments of formulas (VIIIba), (VIIIca), or (VIIIcb), wherein the dashed line marked with an asterisk indicates attachment to D of formula (VIII) by forming an amide bond with the aromatic amino group of D and the unmarked dashed line indicates attachment to the rest of L of formula (VIII):

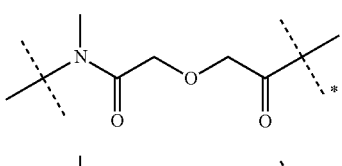
(VIIIba)

(VIIIca)

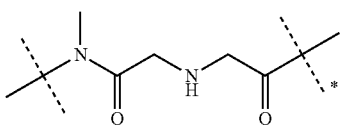
(VIIIcb)

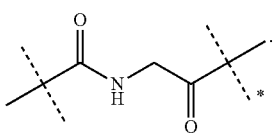

Another suitable reversible prodrug linker moiety for aromatic amine-comprising drugs is described in WO-A 2011/012721. Accordingly, a preferred polymeric prodrug is given by a conjugate D-L, wherein
D is the biologically active moiety; and
L is a non-biologically active linker moiety -$L^1$ represented by formula (IX),

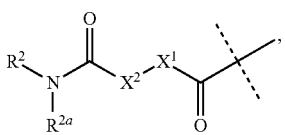
(IX)

wherein the dashed line indicates the attachment to an aromatic amine group of an aromatic amine-containing biologically active moiety D by forming an amide bond; and wherein $X^1$, $X^2$, $R^2$ and $R^{2a}$ of formula (IX) have the following meaning:
$X^1$ is $C(R^1R^{1a})$ or a cyclic fragment selected from $C_{3-7}$ cycloalkyl, 4- to 7-membered heterocyclyl, phenyl, naphthyl, indenyl, indanyl, tetralinyl, and 9- to 11-membered heterobicyclyl, $X^2$ is a chemical bond or selected from $C(R^3R^{3a})$, $N(R^3)$, O, $C(R^3R^{3a})$—$C(R^4R^{4a})$, $C(R^3R^{3a})$—$N(R^4)$, $N(R^3)$—$C(R^4R^{4a})$, $C(R^3R^{3a})$—O, and O—C$(R^3R^{3a})$, wherein in case $X^1$ is a cyclic fragment, $X^2$ is a chemical bond, $C(R^3R^{3a})$, $N(R^3)$ or O, optionally, in case $X^1$ is a cyclic fragment and $X^2$ is $C(R^3R^{3a})$, the order of the $X^1$ fragment and the $X^2$ fragment shown in formula (IX) may be changed, $R^1$, $R^3$ and $R^4$ are independently selected from the group consisting of H, $C_{1-4}$ alkyl and —$N(R^5R^{5a})$, $R^{1a}$, $R^2$, $R^{2a}$, $R^{3a}$, $R^{4a}$ and $R^{5a}$ are independently selected from the group consisting of H, and $C_{1-4}$ alkyl, optionally, one of the pairs $R^{2a}/R^2$, $R^{2a}/R^{3a}$, $R^{2a}/R^{4a}$ are joined to form a 4- to 7-membered at least partially saturated heterocycle, $R^5$ is $C(O)R^6$, $R^6$ is $C_{1-4}$ alkyl, optionally, one of the pairs $R^{1a}/R^{4a}$, $R^{3a}/R^{4a}$ or $R^{1a}/R^{3a}$ form a chemical bond; and wherein $L^1$ is substituted with one group $L^2$-Z and optionally further substituted; and wherein
$L^2$ is a single chemical bond or a spacer; and
Z is the polymeric carrier of the polymeric prodrug.

Thus, the polymeric carrier is attached to any one of $X^1$, $X^2$, $R^1$, $R^{1a}$, $R^2$, $R^{2a}$, $R^3$, $R^{3a}$, $R^4$, $R^5$, $R^{5a}$ or $R^6$ of formula (IX), either directly (if $L^2$ is a single chemical bond) or through a spacer moiety (if $L^2$ is a spacer).

More preferably, the moiety L according to formula (IX) is selected from the following formulas:

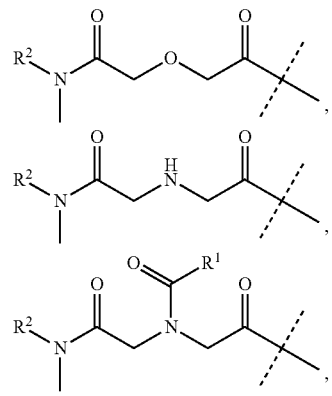

wherein the dashed line indicates attachment to the biologically active moiety D, and
$R^1$ and $R^2$ are used as defined in formula (IX).

Preferably, $R^{1a}$, $R^2$, $R^{2a}$, $R^{3a}$, $R^{4a}$ and $R^{5a}$ of formula (IX) are independently selected from the group consisting of H, and $C_{1-4}$ alkyl.

Another suitable reversible prodrug linker moiety for aromatic amine-comprising drugs is described in WO 2011/012722. Accordingly, a preferred linker structure for the polymeric prodrug is given by a conjugate D-L, wherein
D is the biologically active moiety; and
L is a non-biologically active linker moiety -$L^1$ represented by formula (X),

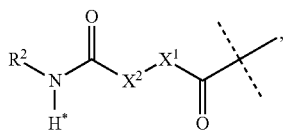
(X)

wherein the dashed line indicates attachment to an aromatic amine group of an aromatic amine-containing biologically active moiety D; and wherein $X^1$, $X^2$, and $R^2$ of formula (X) have the following meaning:

$X^1$ is $C(R^1R^{1a})$ or a cyclic fragment selected from $C_{3-7}$ cycloalkyl, 4 to 7 membered heterocyclyl, phenyl, naphthyl, indenyl, indanyl, tetralinyl, and 9 to 11 membered heterobicyclyl;

wherein in case $X^1$ is a cyclic fragment, said cyclic fragment is incorporated via two adjacent ring atoms and the ring atom of $X^1$, which is adjacent to the carbon atom of the amide bond, is also a carbon atom;

$X^2$ is a chemical bond or selected from $C(R^3R^{3a})$, $N(R^3)$, O, $C(R^3R^{3a})$—$C(R^4R^{4a})$, $C(R^3R^{3a})$—$N(R^4)$, $N(R^3)$—$C(R^4R^{4a})$, $C(R^3R^{3a})$—O, and O—C$(R^3R^{3a})$;

wherein in case $X^1$ is a cyclic fragment, $X^2$ is a chemical bond, $C(R^3R^{3a})$, $N(R^3)$ or O;

optionally, in case $X^1$ is a cyclic fragment and $X^2$ is $C(R^3R^{3a})$, the order of the $X^1$ fragment and the $X^2$ fragment shown in formula (X) may be changed and the cyclic fragment is incorporated into the substructure of formula (X) via two adjacent ring atoms;

$R^1$, $R^3$ and $R^4$ are independently selected from the group consisting of H, $C_{1-4}$ alkyl and —$N(R^5R^{5a})$;

$R^{1a}$, $R^2$, $R^{3a}$, $R^{4a}$ and $R^{5a}$ are independently selected from the group consisting of H, and $C_{1-4}$ alkyl;

$R^5$ is $C(O)R^6$;

$R^6$ is $C_{1-4}$ alkyl;

optionally, one of the pairs $R^{1a}/R^{4a}$, $R^{3a}/R^{4a}$ or $R^{1a}/R^{3a}$ form a chemical bond, provided that the hydrogen marked with the asterisk in formula (X) is not replaced;

wherein L is substituted with one group $L^2$-Z and optionally further substituted, provided that the hydrogen marked with the asterisk in formula (X) is not replaced; and wherein $L^2$ is a single chemical bond or a spacer; and Z is the polymeric carrier of the polymeric prodrug.

Thus, the polymeric carrier is attached to any one of $X^1$, $X^2$, $R^1$, $R^{1a}$, $R^2$, $R^3$, $R^{3a}$, $R^4$, $R^5$, $R^{5a}$ or $R^6$ of formula (X), either directly (if $L^2$ is a single chemical bond) or through a spacer moiety (if $L^2$ is a spacer).

More preferably, the moiety $L^1$ of formula (X) is selected from the group consisting of formulas (i) through (xxix):

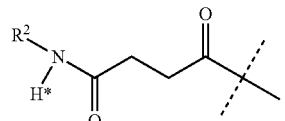
(i)

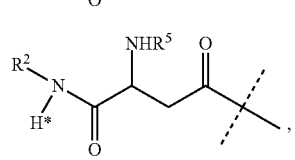
(ii)

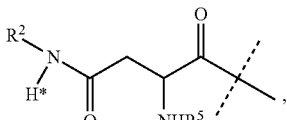
(iii)

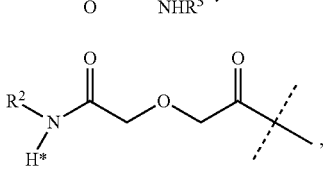
(iv)

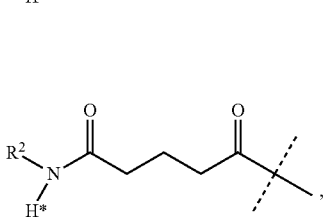
(v)

(vi)

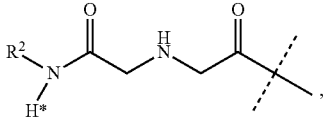
(vii)

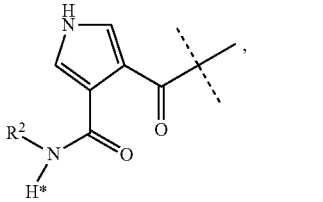
(viii)

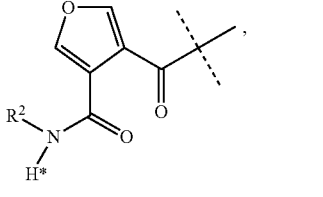
(ix)

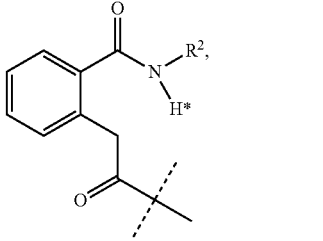
(x)

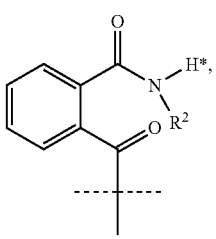

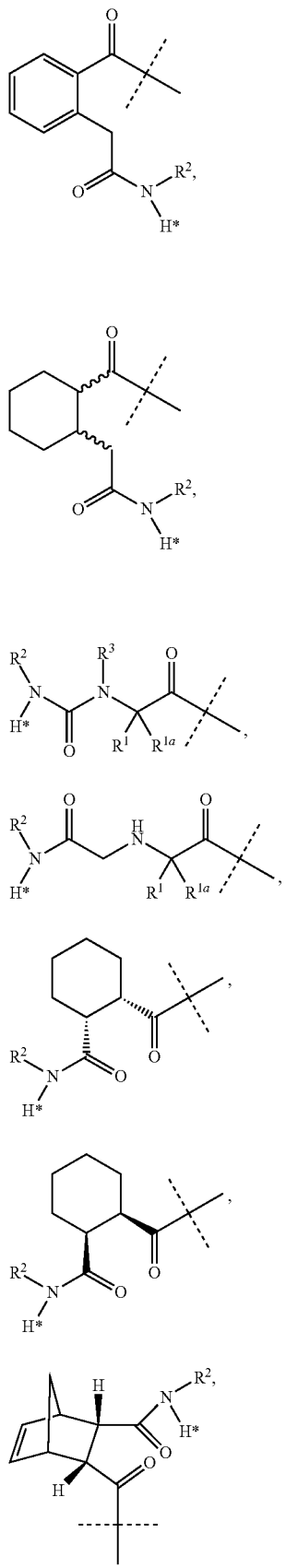
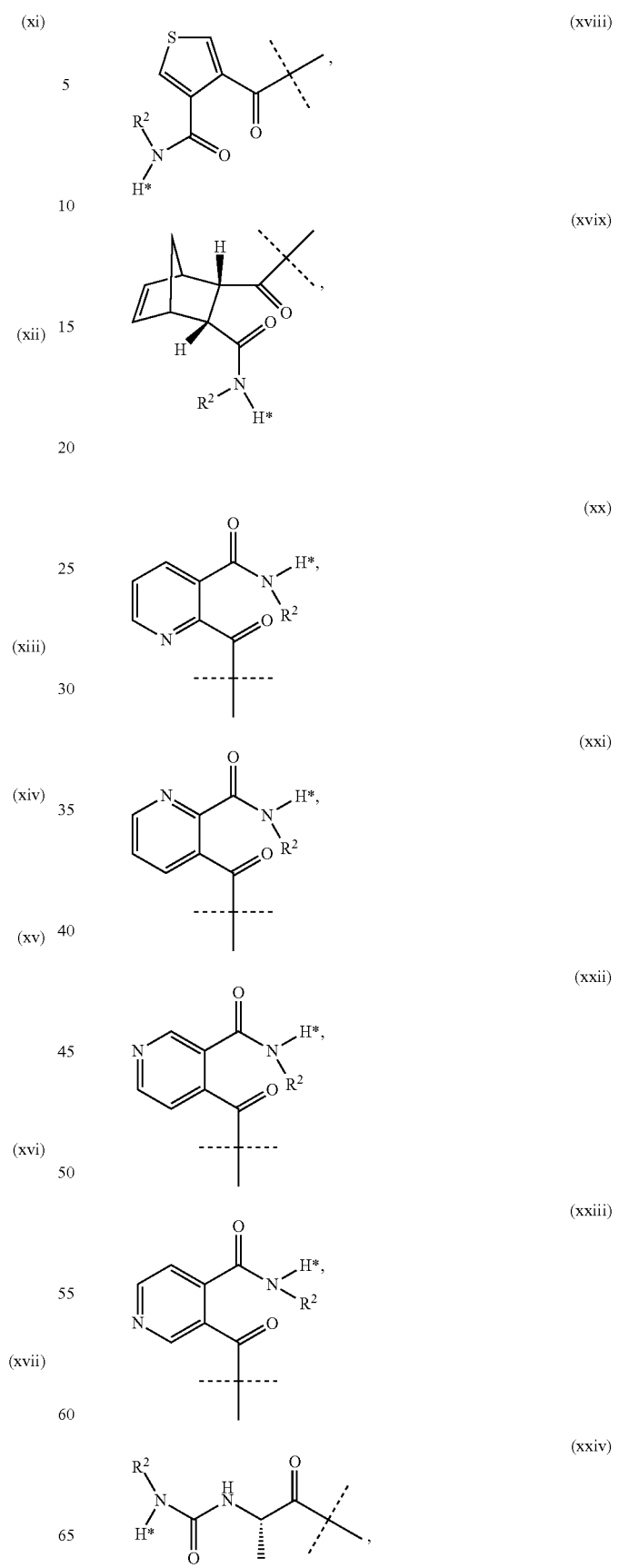

-continued

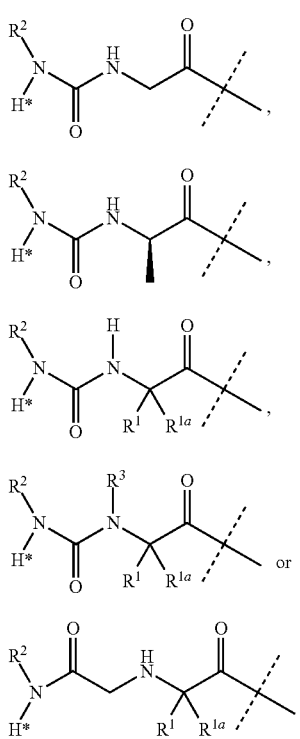

wherein the dashed line indicates attachment to D, and R$^1$, R$^{1a}$, R$^2$, R$^3$, and R$^5$ are used as defined in formula (X).

The amino substituent of the aromatic fragment of D forms together with the carbonyl-fragment (—C(O)—) on the right hand side of L$^1$ (as depicted in formula (X)) an amide bond between L$^1$ and D. By consequence, D and L$^1$ of formula (X) are connected (chemically bound) by an amide fragment of the general structure Y$^1$—C(O)—N(R)—Y$^2$. Y$^1$ indicates the remaining parts of the sub-structure of formula (X) and Y$^2$ indicates the aromatic fragment of D. R is a substituent, such as C$_{1-4}$ alkyl or preferably hydrogen.

As indicated above, X$^1$ of formula (X) may also be a cyclic fragment such as C$_{3-7}$ cycloalkyl, phenyl or indanyl. In case X$^1$ is such a cyclic fragment, the respective cyclic fragment is incorporated into L$^1$ of formula (X) via two adjacent ring atoms (of said cyclic fragment). For example, if X$^1$ is phenyl, the phenyl fragment of L$^1$ is bound to X$^2$ of L$^1$ via a first (phenyl) ring atom being in α-position (adjacent) to a second (phenyl) ring atom, which itself is bound to the carbon atom of the carbonyl-fragment on the right hand side of L$^1$ according to formula (X), i.e. the carbonyl fragment which together with the aromatic amino group of D forms an amide bond.

Preferably, L$^1$ of formula (X) is defined as follows:
X$^1$ is C(R$^1$R$^{1a}$), cyclohexyl, phenyl, pyridinyl, norbonenyl, furanyl, pyrrolyl or thienyl,
wherein in case X$^1$ is a cyclic fragment, said cyclic fragment is incorporated into L$^1$ of formula (X) via two adjacent ring atoms;
X$^2$ is a chemical bond or selected from C(R$^3$R$^{3a}$), N(R$^3$), O, C(R$^3$R$^{3a}$)—O or C(R$^3$R$^{3a}$)—C(R$^4$R$^{4a}$);
R$^1$, R$^3$ and R$^4$ are independently selected from H, C$_{1-4}$ alkyl and —N(R$^5$R$^{5a}$);
R$^{1a}$, R$^{3a}$, R$^{4a}$ and R$^{5a}$ are independently selected from H and C$_{1-4}$ alkyl;
R$^2$ is C$_{1-4}$ alkyl;
R$^5$ is C(O)R$^6$;
R6 is C$_{1-4}$ alkyl;

More preferably, L$^1$ of formula (X) is selected from the following formulas (i) to (xxix):

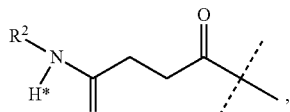

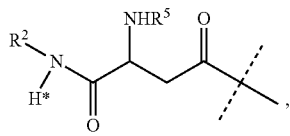

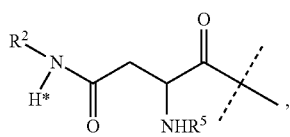

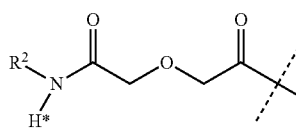

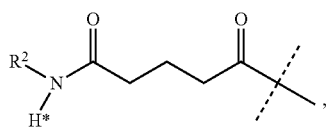

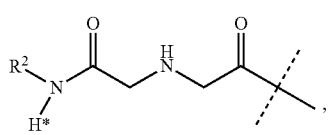

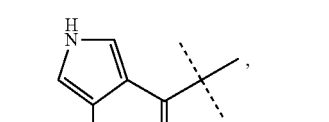

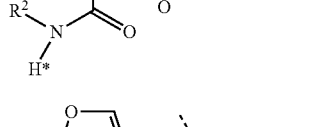

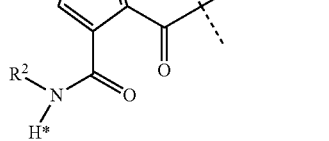

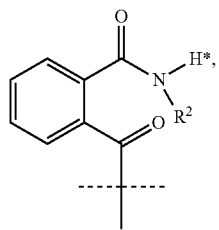
(x)
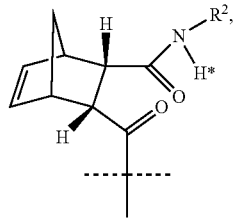
(xvii)
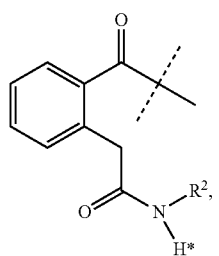
(xi)
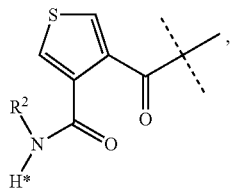
(xviii)
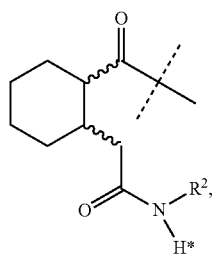
(xii)
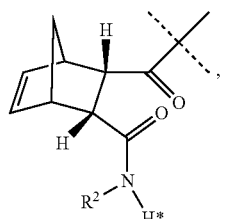
(xvix)
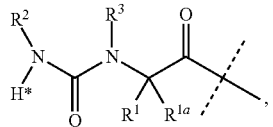
(xiii)
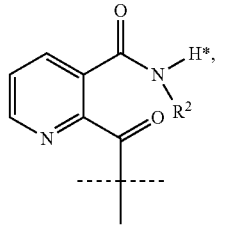
(xx)
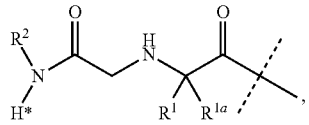
(xiv)
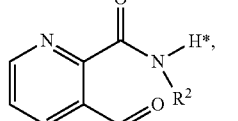
(xxi)
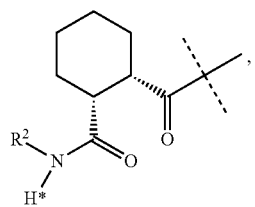
(xv)
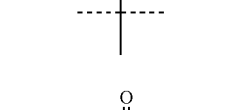
(xxii)
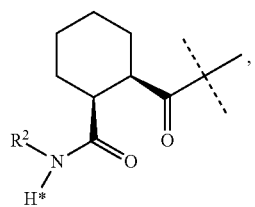
(xvi)
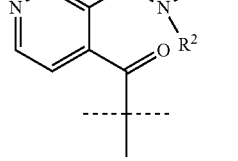
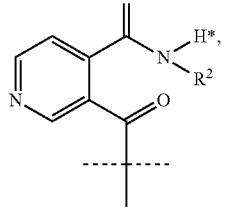
(xxiii)

-continued (xxiv)

(xxv)

(xxvi)

(xxvii)

(xxviii)

or (xxix)

wherein the dashed line indicates attachment to D,
$R^5$ is $C(O)R^6$, and
$R^1$, $R^{1a}$, $R^2$, $R^3$ and $R^6$ are independently from each other $C_{1-4}$ alkyl.

Another suitable reversible prodrug linker moiety for hydroxyl-comprising drugs is described in WO 2011/012721. Accordingly, a preferred polymeric prodrug is given by formula (XI):

$$D-O-Z^0 \quad (XI),$$

wherein,
D is a hydroxyl-comprising biologically active moiety comprising O, i.e. oxygen, of formula (XI) which is coupled to the moiety $Z^0$ through said oxygen of the hydroxyl group; and wherein $Z^0$ of formula (XI) has the following meaning:

$Z^0$ is $C(O)$—$X^0$—$Z^1$; $C(O)O$—$X^0$—$Z^1$; $S(O)_2$—$X$—$Z^1$; $C(S)$—$X$—$Z^1$; $S(O)_2O$—$X^0$—$Z^1$; $S(O)_2N(R^1)$—$X^0$—$Z^1$; $CH(OR)$—$X^0$—$Z^1$; $C(OR)(OR^2)$—$X^0$—$Z^1$; $C(O)N(R^1)$—$X^0$—$Z^1$; $P(=O)(OH)O$—$X^0$—$Z^1$; $P(=O)(OR^1)O$—$X^0$—$Z^1$; $P(=O)(SH)O$—$X^0$—$Z^1$; $P(=O)(SR^1)O$—$X^0$—$Z^1$; $P(=O)(OR^1)$—$X^0$—$Z^1$; $P(=S)(OH)O$—$X^0$—$Z^1$; $P(=S)(OR)O$—$X^0$—$Z^1$; $P(=S)(OH)N(R^1)$—$X^0$—$Z^1$; $P(=S)(OR^1)N(R^2)$—$X^0$—$Z^1$; $P(=O)(OH)N(R^1)$—$X^0$—$Z^1$; or $P(=O)(OR^1)N(R^2)$—$X^0$—$Z^1$;

$R^1$, $R^2$ are independently selected from the group consisting of $C_{1-6}$ alkyl; or $R^1$, $R^2$ jointly form a $C_{1-6}$ alkylene bridging group;
$X^0$ is $(X^{0A})_{m1}$—$(X^{0B})_{m2}$;
m1 and m2 are independently 0 or 1;

$X^{0A}$ is $T^0$;
$X^{0B}$ is a branched or unbranched $C_{1-10}$ alkylene group which is unsubstituted or substituted with one or more $R^3$, which are the same or different;
$R^3$ is halogen; CN; $C(O)R^4$; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $SR^4$; $N(R^4R^{4a})$; $NO_2$; $OC(O)R^4$; $N(R^4)C(O)R^{4a}$; $N(R^4)SO_2R^{4a}$; $N(R^4)S(O)R^{4a}$; $N(R^4)C(O)N(R^{4a}R^{4b})$; $N(R^4)C(O)OR^{4a}$; $OC(O)N(R^4R^{4a})$; or $T^0$;
$R^4$, $R^{4a}$, $R^{4b}$ are independently selected from the group consisting of H; $T^0$; $C_{1-4}$ alkyl; $C_{2-4}$ alkenyl; and $C_{2-4}$ alkynyl, wherein $C_{1-4}$ alkyl; $C_{2-4}$ alkenyl; and $C_{2-4}$ alkynyl are optionally substituted with one or more $R^5$, which are the same of different;
$R^5$ is halogen; CN; $C(O)R^6$; $C(O)OR^6$; $OR^6$; $C(O)R^6$; $C(O)N(R^6R^{6a})$; $S(O)_2N(R^6R^{6a})$; $S(O)N(R^6R^{6a})$; $S(O)_2R^6$; $S(O)R^6$; $N(R^6)S(O)_2N(R^{6a}R^{6b})$; $SR^6$; $N(R^6R^{6a})$; $NO_2$; $OC(O)R^6$; $N(R^6)C(O)R^{6a}$; $N(R^6)SO_2R^{6a}$; $N(R^6)S(O)R^{6a}$; $N(R^6)C(O)N(R^{6a}R^{6b})$; $N(R^6)C(O)OR^{6a}$; $OC(O)N(R^6R^{6a})$;
$R^6$, $R^{6a}$, $R^{6b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;
$T^0$ is phenyl; naphthyl; azulenyl; indenyl; indanyl; $C_{3-7}$ cycloalkyl; 3 to 7 membered heterocyclyl; or 8 to 11 membered heterobicyclyl, wherein $T^0$, is optionally substituted with one or more $R^7$, which are the same or different;
$R^7$ is halogen; CN; $COOR^8$; $OR^8$; $C(O)R^8$; $C(O)N(R^8R^{8a})$; $S(O)_2N(R^8R^{8a})$; $S(O)N(R^8R^{8a})$; $S(O)_2R^8$; $S(O)_2R^8$; $N(R^8)S(O)_2N(R^{8a}R^{8b})$; $SR^8$; $N(R^8R^{8a})$; $NO_2$; $OC(O)R^8$; $N(R^8)C(O)R^{8a}$; $N(R^8)S(O)_2R^{8a}$; $N(R^8)S(O)R^{8a}$; $N(R^8)C(O)OR^{8a}$; $N(R^8)C(O)N(R^{8a}R^{8b})$; $OC(O)N(R^8R^{8a})$; oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^9$, which are the same or different;
$R^8$, $R^{8a}$, $R^{8b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{10}$, which are the same or different;
$R^9$, $R^{10}$ are independently selected from the group consisting of halogen; CN; $C(O)R^{11}$; $C(O)OR^{11}$; $OR^{11}$; $C(O)R^{11}$; $C(O)N(R^{11}R^{11a})$; $S(O)_2N(R^{11}R^{11a})$; $S(O)N(R^{11}R^{11a})$; $S(O)_2R^{11}$; $S(O)R^{11}$; $N(R^{11})S(O)_2N(R^{11a}R^{11b})$; $SR^{11}$; $N(R^{11}R^{11a})$; $NO_2$; $OC(O)R^{11}$; $N(R^{11})C(O)R^{11a}$; $N(R^{11})SO_2R^{11a}$; $N(R^{11})S(O)R^{11a}$; $N(R^{11})C(O)N(R^{11a}R^{11b})$; $N(R^{11})C(O)OR^{11a}$; and $OC(O)N(R^{11}R^{11a})$;
$R^{11}$, $R^{11a}$, $R^{11b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;
$Z^1$ is the polymeric carrier of the polymeric prodrug, which is covalently attached to $X^0$.

Preferably, $Z^0$ is $C(O)$—$X^0$—$Z^1$; $C(O)O$—$X^0$—$Z^1$; or $S(O)_2$—$X^0$—$Z^1$. More preferably, $Z^0$ is $C(O)$—$X^0$—$Z^1$; or $C(O)O$—$X^0$—$Z^1$. Even more preferably, $Z^0$ is $C(O)$—$X^0$—$Z^1$.

Preferably, $X^0$ is unsubstituted.
Preferably, m1 is 0 and m2 is 1.

Preferably, X⁰—Z⁰ is C(R¹R²)CH₂—Z⁰, wherein $R^1$, $R^2$ are independently selected from the group consisting of H and $C_{1-4}$ alkyl, provided that at least one of $R^1$, $R^2$ is other than H; or $(CH_2)_n$—Z⁰, wherein n is 3, 4, 5, 6, 7 or 8.

Preferably, $Z^1$ is covalently attached to X⁰ via amide group.

Another suitable reversible prodrug linker moiety for aromatic hydroxyl-comprising drugs is described in WO-A 2011/089214. Accordingly, a preferred polymeric prodrug is given by a conjugate D-L, wherein D is a biologically active moiety containing an aromatic hydroxyl group; and L is a non-biologically active linker containing i) a moiety $L^1$ represented by formula (XII), (XII)

wherein the dashed line indicates the attachment of $L^1$ to the aromatic hydroxyl group of D by forming a carbamate group and $R^1$, $R^2$, $R^{2a}$, $R^3$, $R^{3a}$ and m of formula (XII) have the following meaning:

$R^1$ is selected from the group consisting of $C_{1-4}$ alkyl, heteroalkyl, $C_{3-7}$ cycloalkyl, and each $R^2$, each $R^{2a}$, $R^3$, $R^{3a}$ are independently selected from hydrogen, substituted or non-substituted linear, branched or cyclic $C_{1-4}$ alkyl or heteroalkyl, m is 2, 3 or 4.

ii) a moiety $L^2$, which is a chemical bond or a spacer, and $L^2$ is bound to the polymeric carrier of the polymeric prodrug;

wherein $L^1$ is substituted with one $L^2$ moiety.

Optionally, L is further substituted.

Thus, the polymeric carrier is attached to any one of $R^1$, $R^2$, $R^{2a}$, $R^3$ or $R^{3a}$ of formula (XII), either directly (if $L^2$ is a single chemical bond) or through a spacer moiety (if $L^2$ is a spacer).

Another suitable reversible prodrug linker moiety for aliphatic amine-comprising drugs is described in WO-A 2011/089216. Accordingly, a preferred polymeric prodrug is given by a conjugate D-L, wherein D is an aliphatic amine-comprising biologically active moiety; and L is a non-biologically active linker containing i) a moiety $L^1$ represented by formula (XIII), (XIII)

wherein the dashed line indicates the attachment of $L^1$ to an aliphatic amino group of D by forming an amide bond and wherein $X^1$, $R^1$, $R^2$, $R^{2a}$, $R^3$, $R^{3a}$, $R^4$ and $R^{4a}$ of formula (XIII) have the following meaning:

$X^1$ is selected from O, S and CH—$R^{1a}$;

$R^1$ and $R^{1a}$ are independently selected from H, OH, and $CH_3$;

$R^2$, $R^{2a}$, $R^4$ and $R^{4a}$ are independently selected from H and $C_{1-4}$ alkyl;

$R^3$, $R^{3a}$ are independently selected from H, $C_{1-4}$ alkyl, and $R^5$ $R^5$ is selected from ii) a moiety $L^2$, which is a chemical bond or a spacer, and $L^2$ is bound to Z, which is the polymeric carrier of the polymeric prodrug;

wherein $L^1$ is substituted with one $L^2$ moiety, optionally, L is further substituted.

Thus, the polymeric carrier is attached to any one of $X^1$, $R^1$, $R^2$, $R^{2a}$, $R^3$, $R^{3a}$, $R^4$ or $R^{4a}$ of formula (XIII), either directly (if $L^2$ is a single chemical bond) or through a spacer moiety (if $L^2$ is a spacer).

Preferably, one of the pair $R^3/R^{3a}$ of formula (XIII) is H and the other one is selected from $R^5$.

Preferably, one of $R^4/R^{4a}$ of formula (XIII) is H.

Optionally, one or more of the pairs $R^3/R^{3a}$, $R^4/R^{4a}$, $R^3/R^4$ of formula (XIII) may independently form one or more cyclic fragments selected from $C_{3-7}$ cycloalkyl, 4 to 7 membered heterocyclyl, or 9 to 11 membered heterobicyclyl.

Optionally, $R^3$, $R^{3a}$, $R^4$ and $R^{4a}$ of formula (XIII) are further substituted. Suitable substituents are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4- to 7-membered heterocycle) or halogen moieties.

Another suitable reversible prodrug linker moiety for aromatic amine-comprising drugs is described in WO-A 2011/089215. Accordingly, a preferred polymeric prodrug is given by a conjugate D-L,
wherein
D is an aromatic amine-comprising biologically active moiety; and
L is a non-biologically active linker containing
i) a moiety $L^1$ represented by formula (XIV),

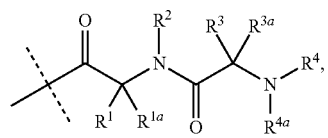

(XIV)

wherein the dashed line indicates the attachment of $L^1$ to an aromatic amino group of D by forming an amide bond and wherein $R^1$, $R^{1a}$, $R^2$, $R^3$, $R^{3a}$, $R^4$ and $R^{4a}$ of formula (XIV) have the following meaning:
$R^1$, $R^{1a}$, $R^2$, $R^3$, $R^{3a}$, $R^4$ and $R^{4a}$ are independently selected from H and $C_{1-4}$ alkyl,
optionally, any two of $R^1$, $R^{1a}$, $R^2$, $R^3$, $R^{3a}$, $R^4$ and $R^{4a}$ may independently form one or more cyclic fragments selected from $C_{3-7}$ cycloalkyl, 4 to 7 membered heterocyclyl, phenyl, naphthyl, indenyl, indanyl, tetralinyl, or 9 to 11 membered heterobicyclyl,
optionally, $R^1$, $R^{1a}$, $R^2$, $R^3$, $R^{3a}$, $R^4$ and $R^{4a}$ are further substituted; suitable substituents are alkyl, alkene, alkine, aryl, heteroalkyl, heteroalkene, heteroalkine, heteroaryl or halogen moieties.
ii) a moiety $L^2$, which is a chemical bond or a spacer, and $L^2$ is bound to Z, which is the polymeric carrier of the polymeric prodrug;
wherein $L^1$ is substituted with one moiety $L^2$,
optionally, L is further substituted.

Suitable substituents are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Thus, the polymeric carrier is attached to any one of $R^1$, $R^{1a}$, $R^2$, $R^3$, $R^{3a}$, $R^4$ or $R^{4a}$ of formula (XIV), either directly (if $L^2$ is a single chemical bond) or through a spacer moiety (if $L^2$ is a spacer).

Preferably, one of $R^4$ or $R^{4a}$ of formula (XIV) is H.

Another suitable reversible prodrug linker moiety is described in U.S. Pat. No. 7,585,837. Accordingly, a preferred polymeric prodrug is given by a prodrug conjugate D-L, wherein
D is a biologically active moiety comprising an amine, carboxyl, phosphate, hydroxyl or mercapto group; and
L is a non-biologically active linker containing
i) a moiety $L^1$ represented by formula (XV):

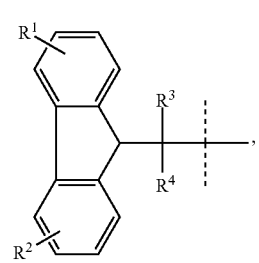

(XV)

wherein the dashed line indicates the attachment of $L^1$ to a functional group of a drug D, wherein such functional group is selected from amino, carboxyl, phosphate, hydroxyl and mercapto; and wherein $R^1$, $R^2$, $R^3$ and $R^4$ of formula (XV) are defined as follows:
$R^1$ and $R^2$ are independently selected from the group consisting of hydrogen, alkyl, alkoxy, alkoxyalkyl, aryl, alkaryl, aralkyl, halogen, nitro, —$SO_3H$, —$SO_2NHR^5$, amino, ammonium, carboxyl, $PO_3H_2$, and $OPO_3H_2$;
$R^3$, $R^4$, and $R^5$ are independently selected from the group consisting of hydrogen, alkyl, and aryl;
ii) a moiety $L^2$, which is a chemical bond or a spacer, and $L^2$ is bound to the polymeric carrier of the polymeric prodrug, and
wherein L is substituted with one $L^2$ moiety.
Optionally, L is further substituted.

Thus, the hydrogel is attached to any one of $R^1$, $R^2$, $R^3$ or $R^4$ of formula (XV), either directly (if $L^2$ is a single chemical bond) or through a spacer moiety (if $L^2$ is a spacer).

Another suitable reversible prodrug linker moiety is described in WO-A 2002/089789.

Accordingly, a preferred polymeric prodrug is shown in formula (XVI):

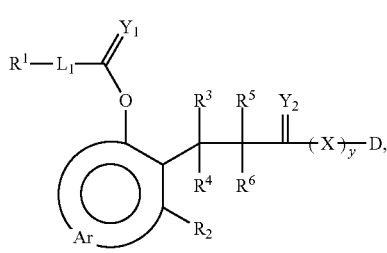

(XVI)

wherein D, X, y, Ar, $L_1$, $Y_1$, $Y_2$, $R^1$, $R^2$, $R^3$, $R^4$, $R^5$, $R^6$ of formula (XVI) are defined as follows:
D is a biologically active moiety;
$L_1$ is a bifunctional linking group;
$Y_1$ and $Y_2$ are independently O, S or $NR^7$;
$R^1$ is the polymeric carrier;
$R^{2-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula XI forms a multisubstituted aromatic hydrocarbon or a multisubstituted heterocyclic group;

Z is either a chemical bond or a moiety that is actively transported into a target cell, a hydrophobic moiety, or a combination thereof;

y is 0 or 1;

X is a chemical bond or a moiety that is actively transported into a target cell, a hydrophobic moiety, or a combination thereof.

Another suitable reversible prodrug linker moiety is described in WO-A 2001/47562. Accordingly, a preferred polymeric prodrug is given by formula (XVII):

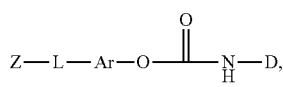

(XVII)

wherein D, L, z and Ar of formula (XVII) have the following meaning:

D is an amine-comprising biologically active moiety comprising NH;

L is a covalent linkage, preferably a hydrolytically stable linkage;

Ar is an aromatic group; and z is the polymeric carrier.

Yet another suitable reversible prodrug linker moiety is described in U.S. Pat. No. 7,393,953 B2. Accordingly, a preferred polymeric prodrug is given by formula (XVIII):

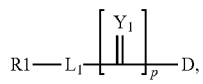

(XVIII)

wherein R1, $L_1$, $Y_1$, p and D of formula (XVIII) have the following meaning:

D is a heteroaromatic amine-comprising biologically active moiety connected through a heteroaromatic amine group of D to the rest of the sub-structure of formula (XVIII);

$Y_1$ is O, S, or $NR_2$;

p is 0 or 1;

$L_1$ is a bifunctional linker, such as, for example, —NH$(CH_2CH_2O)_m(CH_2)_mNR_3$—, —NH$(CH_2CH_2O)_mC(O)$—, —NH$(CR_4R_5)_mOC(O)$—, —C(O)$(CR_4R_5)_m$NHC(O)$(CR_8R_7)_qNR_3$—, —C(O)O$(CH_2)_mO$—, —C(O)$(CR_4R_5)_m$NR_3$—, —C(O)NH$(CH_2CH_2O)_m(CH_2)_mNR_3$—, —C(O)O—$(CH_2CH_2O)_mNR_3$—, —C(O)NH$(CR_4R_5)_mO$—, —C(O)O$(CR_4R_5)_mO$, —C(O)NH$(CH_2CH_2O)_m$—,

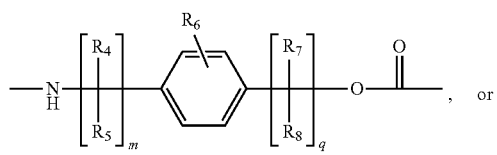

, or

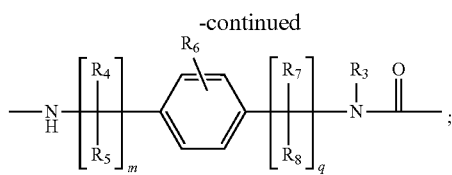

;

$R_2$, $R_3$, $R_4$, $R_5$, $R_7$ and $R_8$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_6$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and m and q are selected independently from each other and each is a positive integer.

Another preferred polymeric prodrug is given by formula (XIX):

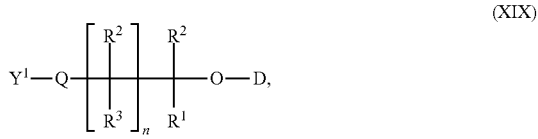

(XIX)

wherein D, $R^1$, $R^2$, $R^3$, $R^4$, $Y^1$ and n of formula (XIX) have the following meaning:

D is a carboxyl-comprising biologically active moiety comprising O of formula (XIX), $R^1$ is selected from the group of unsubstituted alkyl; substituted alkyl; unsubstituted phenyl; substituted phenyl; unsubstituted naphthyl; substituted naphthyl; unsubstituted indenyl; substituted indenyl; unsubstituted indanyl; substituted indanyl; unsubstituted tetralinyl; substituted tetralinyl; unsubstituted $C_{3-10}$ cycloalkyl; substituted $C_{3-10}$ cycloalkyl; unsubstituted 4- to 7-membered heterocyclyl; substituted 4- to 7-membered heterocyclyl; unsubstituted 9- to 11-membered heterobicyclyl; and substituted 9- to 11-membered heterobicyclyl;

$R^2$ is selected from H, unsubstituted alkyl, and substituted alkyl;

$R^3$ and $R^4$ are independently selected from the group consisting of H, unsubstituted alkyl, and substituted alkyl;

Q is a spacer moiety;

n is 0 or 1, optionally, $R^1$ and $R^3$ are joined together with the atoms to which they are attached to form a ring A, A is selected from the group consisting of $C_{3-10}$ cycloalkyl; 4- to 7-membered aliphatic heterocyclyl; and 9- to 11-membered aliphatic heterobicyclyl, wherein A is unsubstituted or substituted;

$Y^1$ is the polymeric carrier.

Preferably, $R^1$ of formula (XIX) is $C_{1-6}$ alkyl or substituted $C_{1-6}$ alkyl, more preferably $C_{1-4}$ alkyl or substituted $C_{1-4}$ alkyl.

More preferably, $R^1$ of formula (XIX) is selected from methyl, ethyl, n-propyl, isopropyl, n-butyl, isobutyl, sec-butyl, t-butyl, and benzyl.

Preferably, $R^2$ of formula (XIX) is H.

Preferably, $R^3$ of formula (XIX) is H, $C_{1-6}$ alkyl or substituted $C_{1-6}$ alkyl, more preferably $C_{1-4}$ alkyl or substituted $C_{1-4}$ alkyl. More preferably, $R^3$ is selected from methyl, ethyl, n-propyl, isopropyl, n-butyl, isobutyl, sec-butyl, t-butyl, and benzyl.

More preferably, $R^3$ of formula (XIX) is H.

Preferably, $R^4$ of formula (XIX) is s H, $C_{1-6}$ alkyl or substituted $C_{1-6}$ alkyl, more preferably $C_{1-4}$ alkyl or substituted $C_{1-4}$ alkyl. More preferably, $R^4$ is selected from methyl, ethyl, n-propyl, isopropyl, n-butyl, isobutyl, sec-butyl, t-butyl, and benzyl.

More preferably, $R^4$ of formula (XIX) is H.

In another preferred embodiment, $R^1$ and $R^3$ of formula (XIX) are joined together with the atoms to which they are attached to form a ring A, wherein A is selected from the group consisting of cyclopropane, cyclobutane, cyclopentane, cyclohexane, and cycloheptane.

Another preferred polymeric prodrug is given by formula (XX):

$$Y_1—W—O-D \qquad (XX),$$

wherein D, $Y_1$ and W of formula (XX) have the following meaning:

D is a carboxyl-comprising biologically active moiety comprising O of formula (XX), W is selected from linear $C_{1-15}$ alkyl; and $Y_1$ is the polymeric carrier of the polymeric prodrug.

The polymeric prodrug comprises one or more biologically active moieties which are coupled to the polymeric carrier through reversible prodrug linkers. In one embodiment, the biologically active moieties are released within a joint from the polymeric prodrug as drug molecules.

In a preferred embodiment, the one or more biologically active moieties for the polymeric prodrugs are preferably selected from the group consisting of (i) non-steroidal anti-inflammatory drugs (NSAIDs), (ii) disease modifying anti-rheumatic drugs (DMARDs), (iii) corticosteroids and (iv) biologics (e.g. antibodies, fragments thereof and fusion proteins, binding proteins, peptides and recombinant proteins). Anybody skilled in the art will recognize compounds belonging to each of these categories, and as such drugs belonging to these categories are incorporated herein as suitable for the current invention.

More preferably, the one or more biologically active moieties for the polymeric prodrugs are preferably selected from the group consisting of (i) non-steroidal anti-inflammatory drugs (NSAIDs), (ii) disease modifying anti-rheumatic drugs (DMARDs), (iii) corticosteroids and (iv) biologics (e.g. antibodies, fragments thereof and fusion proteins, and recombinant proteins). Anybody skilled in the art will recognize compounds belonging to each of these categories and as such drugs belonging to these categories are incorporated herein as suitable for the current invention.

In a further preferred embodiment, the one or more biologically active moieties for the polymeric prodrugs are selected from the group consisting of indomethacin; non-steroidal anti-inflammatory drugs (NSAIDs) such as aspirin, ibuprofen, and other propionic acid derivatives (such as alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen); acetic acid derivatives (such as indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac); fenamic acid derivatives (such as flufenamic acid, meclofenamic acid, mefenamic acid, niflumic acid and tolfenamic acid); biphenylcarboxylic acid derivatives (such as diflunisal and flufenisal); oxicams (such as isoxicam, piroxicam, sudoxicam and tenoxican); salicylates (such as acetyl salicylic acid, sulfasalazine) and the pyrazolones (such as apazone, bezpiperylon, feprazone, mofebutazone, oxyphenbutazone, phenylbutazone) and opioid analgesics (such as such as fentanyl, morphine, sufentanil, hydromorphone, methadone, oxycodone, bupremorphine); methotrexate, cyclooxygenase-2 (COX-2) inhibitors (such as celecoxib), anti-TNF agents (such as adalimumab, certolizumab pegol, etanercept, golimumab, infliximab); anti-IL-1, -6, -12, -15, -18 and -21 and -23 agents (such as anakinra, Tocilizumab); nerve growth factor inhibitors, nerve growth factor receptor (NGFR) antagonists, RN64, REGN475, fasinumab, tanezumab, MED1578, ABT110, anti-NGF antibodies and antibody derivatives, and anti-NGFR antibodies and antibody derivatives; TrkA antagonists (such as ARRY-470, FX007, ARRY 872) glucocorticoids or steroids (such as cortisone, prednisolone, flurometholone, dexamethasone, medrysone, loteprednol, fluazacort, hydrocortisone, prednisone, betamethasone, clobetasone, prednisone, methylprednisolone, riamcinolone hexacatonide, paramethasone acetate, diflorasone, fluocinonide, fluocinolone, triamcinolone, derivatives thereof, and mixtures thereof); local analgesics (such as lidocaine, bupivacaine, procaine); leflunomide; immunomodulatory agents (such as cyclosporine, tacrolimus, azathioprine, cyclophosphamide, minocycline, rituximab); gold compounds; D-penicillamine; sulfasalazine; chloroquine derivatives (including but not limited to hydroxychloroquine); CD20 directed antibodies, such as ocrelizumab and ofatumumab; RANKL inhibitors, such as denosumab; TRU-015; INCB018424; VX-V02; bone morphogenetic protein (BMP) (such as BMP-I, BMP-2, BMP-3, BMP-4, BMP-5, BMP-6, BMP-7, BMP-8, BMP-9, BMP-IO, BMP-II, BMP-12, BMP-13, BMP-14, BMP-15, BMP-16, BMP-17, BMP-18, BMP-19, BMP-20, BMP-21); FGF (fibroblast growth factors, such as FGFI FGF2, FGF4, FGF7, FGFIO, FGFI9, FGF21, FGF23); TGF-β (transforming growth factor-β, such as TGF β1); growth hormone; IGF (insulin-like growth factor, such as IGF-I); NELL peptides; VEGF (vascular endothelial growth factor); PDGF (platelet-derived growth factor); PTH (parathyroid hormone)/PTHrp (PTHregulated protein); oxysterols; lipophilic statins, statins (such as atorvastatin, cerivastatin, fluvastatin, lovastatin, mevastatin, pitavastatin, pravastatin, rosuvastatin, simvastatin); growth/differentiation factor 5 (GDF5); LIM mineralization proteins (LMPS); matrix metalloproteinases; aggrecanases (AD-AMTSs); cysteine-dependent cathepsins; growth factors; and cell adhesion molecules (CAMs); bisphosphonates(s) (including both N-containing and non-N-containing bisphosphonates(s), selected from the group comprising: pamidronate, neridronate, olpadronate, alendronate, ibandronate, risedronate, and zoledronate. Non-containing bisphosphonates are for example etidronate, clodronate, and tiludronate).

More preferably, the one or more biologically active moieties for the polymeric prodrugs are selected from the group consisting of indomethacin; non-steroidal anti-inflammatory drugs (NSAIDs) such as aspirin, ibuprofen, and other propionic acid derivatives (such as alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen); acetic acid derivatives (such as indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac); fenamic acid derivatives (such as flufenamic acid, meclofenamic acid, mefenamic acid, niflumic acid and tolfenamic acid); biphenylcarboxylic acid derivatives (such as diflunisal and flufenisal); oxicams (such as isoxicam, piroxicam, sudoxicam and tenoxican); salicylates (such as acetyl salicylic acid, sulfasalazine) and the pyrazolones (such as apazone, bezpiperylon, feprazone, mofebutazone, oxyphenbutazone, phenylbutazone) and opioid analgesics (such as such as fentanyl, morphine, sufentanil, hydromorphone, methadone, oxycodone, bupremorphine); methotrexate, cyclooxygenase-2 (COX-2) inhibitors (such as celecoxib), anti-TNF agents (such as adalimumab, certolizumab pegol, etanercept, golimumab, infliximab); anti-IL-1, -6, -12, -15, -18 and -21 and -23 agents (such as anakinra, Tocilizumab); glucocorticoids or steroids (such as cortisone, prednisolone, flurometholone, dexamethasone, medrysone, loteprednol, fluazacort, hydrocortisone, prednisone, betamethasone, clobetasone, prednisone, methylprednisolone, riamcinolone hexacatonide, paramethasone acetate, diflorasone, fluocinonide, fluocinolone, triamcinolone, derivatives thereof, and mixtures thereof); local analgesics (such as lidocaine, bupivacaine, procaine); leflunomide; immunomodulatory agents (such as cyclosporine, tacrolimus, azathioprine, cyclophosphamide, minocycline, rituximab); gold compounds; D-penicillamine; sulfasalazine; chloroquine derivatives; ocrelizumab; ofatumumab; denosumab; TRU-015; INCB018424; VX-V02; bone morphogenetic protein (BMP) (such as BMP-I, BMP-2, BMP-3, BMP-4, BMP-5, BMP-6, BMP-7, BMP-8, BMP-9, BMP-IO, BMP-II, BMP-12, BMP-13, BMP-14, BMP-15, BMP-16, BMP-17, BMP-18, BMP-19, BMP-20, BMP-21); FGF (fibroblast growth factors, such as FGFI FGF2, FGF4, FGF7, FGFIO, FGFI9, FGF21, FGF23); TGF-β (transforming growth factor-β, such as TGF β1); growth hormone; IGF (insulin-like growth factor, such as IGF-I); NELL peptides; VEGF (vascular endothelial growth factor); PDGF (platelet-derived growth factor); PTH (parathyroid hormone)/PTHrp (PTHregulated protein); oxysterols; lipophilic statins; growth/differentiation factor 5 (GDF5); LIM mineralization proteins (LMPS); matrix metalloproteinases; aggrecanases (ADAMTSs); cysteine-dependent cathepsins; growth factors; and cell adhesion molecules (CAMs).

The one or more biologically active moieties for the polymeric prodrugs may also be a natural product, isolated or synthesized, and derivatives thereof, including anthraquinones and their prodrugs such as rhein, diacerein, argirein, and aloe-emodin.

The one or more biologically active moieties for the polymeric prodrugs may also be a P38 Mitogen activated protein (MAP) kinase inhibitors, such as FX-005, ARRY-797, doramapimod, pamapimod, SB203580, SB202190, LY2228820, VX-702, PH-797804, TAK715, VX-745, SCIO0469, ORG48762-0, pyrazolopyridine derivatives, R1503, 5-aminopyrazol-4-yl ketones, and AMG-548; an inhibitor of Matrix metalloproteinase (MMP) activity, such as ALS 1-0635, AC-RCGVPD-NH2 peptide, N-substituted 4-arylsulonylpiperidine-4-hydroxamic acids, 4-aminoprolines, 6-benzyl-5,7-dioxo-6,7-dihydro-5H-thiazolo[3,2-c]pyrimidine-2-carboxylic acid benzyl esters, 4-[l-methyl-2,4-dioxo-6-(3-phenyl-prop-1-ynyl)-1,4-dihydro-2H-quinazolin-3-ylmethyl]-benzoic acids, and galardin; a Tyrosine kinase inhibitor, such as genistein, herbimycin A, 4,5-dianilinophthalimide (DAPH), tyrphostin AG 82, tyrphostin AG 556, anthrapyrazolones, imatinib, gefitinib, erlotinib, sunitinib, polyoxypregane glycoside (PPG), and sorafenib.

In another preferred embodiment, the one or more biologically active moieties for the polymeric prodrugs is a diagnostic agent, such as a contrast agent. Such agents are known in the art.

The polymeric prodrug or pharmaceutical composition comprising a polymeric prodrug may contain one or more biological active moieties. The release of the biological active moieties may occur with the same or different half-lives.

In a particularly preferred embodiment, the polymeric prodrug comprises dexamethasone as biologically active moiety, i.e. the polymeric prodrug is a polymeric dexamethasone prodrug.

Preferably, the dexamethasone prodrug comprises a hydrogel, more preferably, a PEG-based hydrogel. Preferred embodiments of a PEG-based hydrogel are as described above.

Preferably, the dexamethasone prodrug comprises a reversible prodrug linker moiety of formula (IX).

Even more preferably, the dexamethasone prodrug is of formula (IXc):

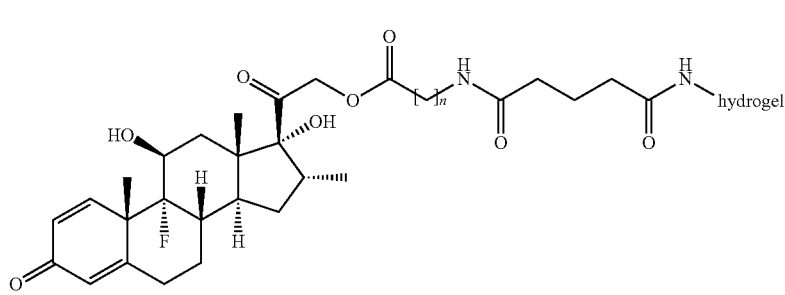

(IXc)

wherein
n is 2.

In a particularly preferred embodiment, the polymeric prodrug comprises IL-1ra as biologically active moiety, i.e. the polymeric prodrug is a polymeric IL-1ra prodrug.

Preferably, the IL-1ra prodrug comprises a hydrogel, more preferably, a PEG-based hydrogel.

Preferred embodiments of a PEG-based hydrogel are as described above.

Preferably, the IL-1ra prodrug comprises a reversible prodrug linker moiety of formula (VII).

Preferably, the reversible prodrug linker of formula (VII) is connected to the PEG-based hydrogel through a spacer moiety. Preferably, the spacer moiety has a molecular weight in the range of from 14 g/mol to 750 g/mol.

Preferably, the spacer moiety is attached to the PEG-based hydrogel via a terminal group selected from

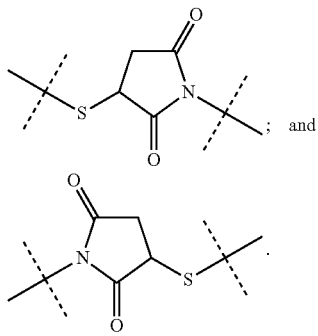
; and

In case the spacer moiety has such terminal group it is furthermore preferred that the spacer moiety has a molecular weight in the range of from 14 g/mol to 500 g/mol calculated without such terminal group.

Most preferably the IL-1ra prodrug is represented by formula (VIIa) or (VIIb):

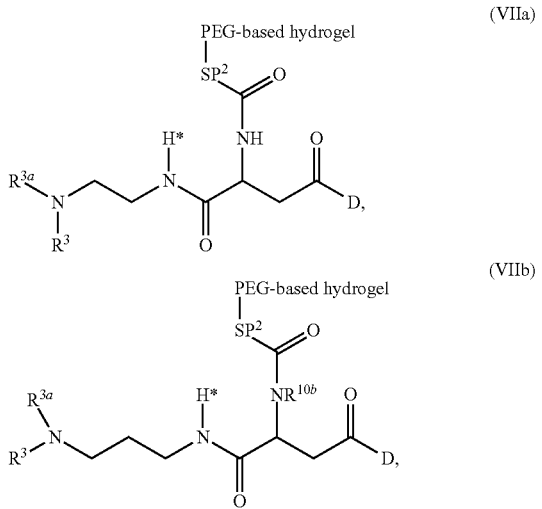

wherein

D is an IL-1ra moiety which is connected to the rest of the molecule through an amine functional group of IL-1ra by forming an amide linkage;

$R^3$, $R^{3a}$ and $R^{10b}$ are independently of each other selected from H and $C_{1-6}$ alkyl; and $SP^2$ is a spacer moiety.

Preferably, $R^{10b}$ of formula (VIIb) is methyl, ethyl, propyl, isopropyl, butyl, isobutyl or tert-butyl. More preferably, $R^{10b}$ of formula (VIIb) is methyl, ethyl, propyl or isopropyl. Even more preferably, $R^{10b}$ of formula (VIIb) is methyl or ethyl and most preferably, $R^{10b}$ of formula (VIIb) is methyl.

The polymeric prodrug or pharmaceutical composition comprising a polymeric prodrug may be used in the prevention, diagnosis and/or treatment of multiple diseases of the joint.

Diseases of the joint which can be prevented, diagnosed and/or treated with the present invention include (ICD code in parenthesis): infectious arthropathies (M00-M03), inflammatory polyarthropathies (M05-M14), arthrosis (M15-M19), other joint disorders (M20-M25), and systemic connective tissue disorders (M30-M36), dorsopathies (M40-M54), soft tissue disorders (M60-M79), osteopathies and chondropathies (M80-M94).

Therefore, in one embodiment, the present invention relates to polymeric prodrug or pharmaceutical composition for use in the prevention, diagnosis and/or treatment of a disease of the joint, wherein the disease of the joint is selected from infectious arthropathies (M00-M03), inflammatory polyarthropathies (M05-M14), arthrosis (M15-M19), other joint disorders (M20-M25), and systemic connective tissue disorders (M30-M36), dorsopathies (M40-M54), soft tissue disorders (M60-M79), osteopathies and chondropathies (M80-M94).

The diseases of the joint also include pain and inflammation following invasive procedures, such as intra-articular injections, synovial aspirations, synovectomy, surgery and arthroscopic procedures.

Preferred diseases of the joint are arthritis and related disorders which are in particular selected from the group of diseases consisting of osteoarthritis, rheumatoid arthritis, Achilles tendinitis, Achondroplasia, Acromegalic arthropathy, Adhesive capsulitis, Adult onset Still's disease, Ankylosing spondylitis, Anserine bursitis, Avascular necrosis, Behcet's syndrome, Bicipital tendonitis, Blount's disease, Brucellar spondylitis, Bursitis, Calcaneal bursitis, Calcium pyrophosphate dihydrate (CPPD), Crystal deposition disease, Caplan's syndrome, Carpal tunnel syndrome, Chondrocalcinosis, Chondromalacia patellae, Chronic synovitis, Chronic recurrent multifocal osteomyelitis, Churg-Strauss syndrome, Cogan's syndrome, Corticosteroid-induced osteoporosis, Costosternal syndrome, CREST syndrome, Cryoglobulinemia, Degenerative joint disease, Dermatomyositis, Diabetic finger sclerosis, Diffuse idiopathic skeletal hyperostosis (DISH), Discitis, Discoid lupus erythematosus, Drug-induced lupus, Duchenne's muscular dystrophy, Dupuytren's contracture, Ehlers-Danlos syndrome, Enteropathic arthritis, Epicondylitis, Erosive inflammatory osteoarthritis, Exercise-induced compartment syndrome, Fabry's disease, Familial Mediterranean fever, Farber's lipogranulomatosis, Felty's syndrome, Fibromyalgia, Fifth's disease, Flat feet, Foreign body synovitis, Freiberg's disease, Fungal arthritis, Gaucher's disease, Giant cell arteritis, Gonococcal arthritis, Goodpasture's syndrome, Gout, Granulomatous arteritis, Hemarthrosis, Hemochromatosis, Henoch-Schonlein purpura, Hepatitis B surface antigen disease, Hip dysplasia, Hurler syndrome, Hypermobility syndrome, Hypersensitivity vasculitis, Hypertrophic osteoarthropathy, Immune complex disease, Impingement syndrome, Jaccoud's arthropathy, Juvenile ankylosing spondylitis, Juvenile dermatomyositis, Juvenile rheumatoid arthritis, Kawasaki disease, Kienbock's disease, Legg-Calve-Perthes disease, Lesch-Nyhan syndrome, Linear scleroderma, Lipoid dermatoarthritis, Lofgren's syndrome, Lyme disease, Malignant synovioma, Marfan's syndrome, Medial plica syndrome, Metastatic carcinomatous arthritis, Mixed connective tissue disease (MCTD), Mixed cryoglobulinemia, Mucopolysaccharidosis, Multicentric reticulohistiocytosis, Multiple epiphyseal dysplasia, Mycoplasmal arthritis, Myofascial pain syndrome, Neonatal lupus, Neuropathic arthropathy, Nodular panniculitis, Ochronosis, Olecranon bursitis, Osgood-Schlatter's disease, Osteoarthritis, Osteochondromatosis, Osteogenesis imperfecta, Osteomalacia, Osteomyelitis, Osteonecrosis, Osteoporosis, Overlap syndrome, Pachydermoperiostosis Paget's disease of bone, Palindromic rheumatism, Patellofemoral pain syndrome, Pellegrini-Stieda syndrome, Pigmented villonodular synovitis, *Piriformis* syndrome, Plantar fasciitis, Polyarteritis *nodosa*, Polymyalgia rheumatica, Polymyositis, Popliteal cysts, Posterior tibial tendonitis, Pott's disease, Prepatellar bursitis, Prosthetic joint infection, Pseudoxanthoma elasticum, Psoriatic arthritis, Raynaud's phenomenon, Reactive arthritis/Reiter's syndrome, Reflex sympathetic dystrophy syndrome, Relapsing polychondritis, Retrocalcaneal bursitis, Rheumatic fever, Rheumatoid arthritis, Rheumatoid vasculitis, Rotator cuff tendonitis, Sacroiliitis, *Salmonella* osteomyelitis, Sarcoidosis, Saturnine gout, Scheuermann's osteochondritis, Scleroderma, Septic arthritis, Seronegative arthritis, *Shigella* arthritis, Shoulder-hand syndrome, Sickle cell arthropathy, Sjogren's syndrome, Slipped capital femoral epiphysis, Spinal stenosis, Spondylolysis, *Staphylococcus* arthritis, Stickler syndrome, Subacute cutaneous lupus, Sweet's syndrome, Sydenham's chorea, Syphilitic arthritis, Systemic lupus erythematosus (SLE), Takayasu's arteritis, Tarsal tunnel syndrome, Tennis elbow, Tietse's syndrome, Transient osteoporosis, Traumatic arthritis, Trochanteric bursitis, Tuberculosis arthritis, Arthritis of Ulcerative colitis, Undifferentiated connective tissue syndrome (UCTS), Urticarial vasculitis, Viral arthritis, Wegener's granulomatosis, Whipple's disease, Wilson's disease, and Yersinial arthritis.

More preferred diseases of the joint are osteoarthritis and rheumatoid arthritis.

In one embodiment the pharmaceutical composition in addition to the polymeric prodrug comprises other biologically active moieties, either in their free form or as prodrugs.

In one embodiment, the present invention relates to a pharmaceutical composition comprising a polymeric prodrug of the present invention, and optionally one or more pharmaceutically acceptable excipients, for use in the prevention, diagnosis and/or treatment of a disease of the joint.

In another embodiment, the present invention relates to a pharmaceutical composition comprising a polymeric prodrug of the present invention, and optionally one or more pharmaceutically acceptable excipients.

Excipients may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The pharmaceutical composition may contain one or more excipients, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability;

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum;

(iii) Preservatives and/or antimicrobials: multidose parenteral preparations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride;

(iv) Stabilizers: Stabilization is achieved by strengthening of the protein-stabilizing forces, by destabilization of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the composition's or composition's container. Suitable surfactants are e.g., alkyl sulfates, such as ammonium lauryl sulfate and sodium lauryl sulfate; alkyl ether sulfates, such as sodium laureth sulfate and sodium myreth sulfate; sulfonates such as dioctyl sodium sulfosuccinates, perfluorooctanesulfonates, perfluorobutanesulfonates, alkyl benzene sulfonates; phosphates, such as alkyl aryl ether phosphates and alkyl ether phosphates; carboxylates, such as fatty acid salts (soaps) or sodium stearate, sodium lauroyl sarcosinate, perfluorononanoate, perfluorooctanoate; octenidine dihydrochloride; quaternary ammonium cations such as cetyl trimethylammonium bromide, cetyl trimethylammonium chloride, cetylpyridinium chloride, polyethoxylated tallow amine, benzalkonium chloride, benzethonium chloride, 5-bromo-5-nitro-1,3-dioxane, dimethyldioctadecylammonium chloride, dioctadecyldimethylammonium bromide; zwitterionics, such as 3-[(3-cholamidopropyl)dimethylammonio]-1-propane-sulfonate, cocamidopropyl hydroxysultaine, amino acids, imino acids, cocamidopropyl betaine, lecithin; fatty alcohols, such as cetyl alcohol, stearyl alcohol, cetostearyl alcohol, oleyl alcohol; polyoxyethylene glycol alkyl ethers, such as octaethylene glycol monododecyl ether, pentaethylene glycol monododecyl ether; polyoxypropylene glycol alkyl ethers; glucoside alkyl ethers, such as decyl glucoside, lauryl glucoside, octyl glucoside; polyoxyethylene glycol octylphenol ethers such as Triton X-100; polyoxyethylene glycol alkylphenol ethers such as nonoxynol-9; glycerol alkyl esters such as glyceryl laurate; polyoxyethylene glycol sorbitan alkyl esters such as polysorbates; sorbitan alkyl esters; cocamide MEA and cocamide DEA; dodecyl dimethylamine oxide; block copolymers of polyethylene glycol and polypropylene glycol, such as poloxamers (Pluronic F-68), PEG dodecyl ether (Brij 35), polysorbate 20 and 80; other anti-absorption agents are dextran, polyethylene glycol, PEG-polyhistidine, BSA and HSA and gelatines. Chosen concentration and type of excipient depends on the effect to be avoided but typically a monolayer of surfactant is formed at the interface just above the CMC value;

(vi) Lyo- and/or cryoprotectants: During freeze- or spray drying, excipients may counteract the destabilizing effects caused by hydrogen bond breaking and water removal. For this purpose sugars and polyols may be used but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used;

(vii) Oxidation protection agents: antioxidants such as ascorbic acid, ectoine, methionine, glutathione, monothioglycerol, morin, polyethylenimine (PEI), propyl gallate, vitamin E, chelating agents such as citric acid, EDTA, hexaphosphate, thioglycolic acid;

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs;

(ix) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture;

The pharmaceutical composition in either dry or liquid form may be provided as a single or multiple dose pharmaceutical composition.

In one embodiment of the present invention, the liquid or dry pharmaceutical composition is provided as a single dose, meaning that the container in which it is supplied contains one pharmaceutical dose.

Alternatively, the liquid or dry pharmaceutical composition is a multiple dose pharmaceutical composition, meaning that the container in which it is supplied contains more than one therapeutic dose, i.e., a multiple dose composition contains at least 2 doses. Such multiple dose pharmaceutical composition can either be used for different patients in need thereof or can be used for one patient, wherein the remaining doses are stored after the application of the first dose until needed.

In another aspect of the present invention the pharmaceutical composition is in a container. Suitable containers for liquid or dry pharmaceutical compositions are, for example, syringes, vials, vials with stopper and seal, ampoules, and cartridges. In particular, the liquid or dry pharmaceutical composition is provided in a syringe. If the pharmaceutical composition is a dry pharmaceutical composition the container preferably is a dual-chamber syringe. In such embodiment, said dry pharmaceutical composition is provided in a first chamber of the dual-chamber syringe and reconstitution solution is provided in the second chamber of the dual-chamber syringe.

In one embodiment, the present invention relates to a container comprising the polymeric prodrug or pharmaceutical composition of the present invention, wherein the container is suited for engagement with an injection device, for use in the prevention, diagnosis and/or treatment of a disease of the joint.

In another embodiment, the present invention relates to a container comprising the polymeric prodrug or pharmaceutical composition of the present invention, wherein the container is suited for engagement with an injection device.

Prior to applying the dry pharmaceutical composition to a patient in need thereof, the dry composition is reconstituted. Reconstitution can take place in the container in which the dry composition is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials, such as, for example, benzylalcohol and cresol. Preferably, the reconstitution solution is sterile water. When a dry pharmaceutical composition is reconstituted, it is referred to as a "reconstituted pharmaceutical composition" or "reconstituted pharmaceutical composition" or "reconstituted composition".

An additional aspect of the present invention relates to the method of administration of a reconstituted or liquid pharmaceutical composition comprising a polymeric prodrug for use in the prevention, diagnosis and/or treatment a disease of the joint of the present invention. Preferably, the pharmaceutical composition is administered via intraarticular injection.

A further aspect is a method of preparing a reconstituted pharmaceutical composition comprising a polymeric prodrug for use in the prevention, diagnosis and/or treatment of a disease of the joint, the method comprising the step of
    contacting the dry pharmaceutical composition with a reconstitution solution.

Another aspect is a reconstituted pharmaceutical composition comprising a polymeric prodrug for use in the treatment, diagnosis and/or prevention a disease of the joint of the present invention, and optionally one or more pharmaceutically acceptable excipients.

In case of diagnosis, the biologically active moiety is preferably a moiety which comprises at least one label, e.g. a fluorescent, phosphorescent, luminescent or radioactive label.

Another aspect of the present invention is the method of manufacturing a dry pharmaceutical composition comprising a polymeric prodrug for use in the prevention, diagnosis and/or treatment of a disease of the joint. In one embodiment, such dry pharmaceutical composition is made by
    (i) admixing the polymeric prodrug with optionally one or more excipients,
    (ii) transferring amounts equivalent to single or multiple doses into a suitable container,
    (iii) drying the pharmaceutical composition in said container, and
    (iv) sealing the container.

Suitable containers are vials, syringes, dual-chamber syringes, ampoules, and cartridges.

Another aspect of the present invention is a kit of parts.

If the injection device is simply a hypodermic syringe then the kit may comprise the syringe, a needle and a container comprising dry pharmaceutical composition for use with the syringe and a second container comprising the reconstitution solution.

If the pharmaceutical composition is a liquid pharmaceutical composition then the kit may comprise the syringe, a needle and a container comprising the liquid pharmaceutical composition for use with the syringe.

Another aspect of the present invention is the pharmaceutical composition for use in the prevention, diagnosis and/or treatment of a disease of the joint contained in a container suited for engagement with an injection device.

In a preferred embodiment, the pharmaceutical composition of the present invention is in the form of an injection, in particular a syringe.

In more preferred embodiments, the injection device is other than a simple hypodermic syringe and so the separate container with reconstituted or liquid pharmaceutical composition is adapted to engage with the injection device such that in use the liquid pharmaceutical composition in the container is in fluid connection with the outlet of the injection device. Examples of injection devices include but are not limited to hypodermic syringes and pen injector devices. Particularly preferred injection devices are the pen injectors in which case the container is a cartridge, preferably a disposable cartridge. Optionally, the kit of parts comprises a safety device for the needle which can be used to cap or cover the needle after use to prevent injury.

A preferred kit of parts comprises a needle and a container containing the pharmaceutical composition and optionally further containing a reconstitution solution, the container being adapted for use with the needle. Preferably, the container is a dual-chamber syringe.

Another aspect of the present invention is a medical device comprising at least one polymeric prodrug or pharmaceutical composition of the present invention. Preferably, such medical device is a syringe with a needle, more preferably with a thin needle, such as a needle smaller than 0.6 mm inner diameter, preferably a needle smaller than 0.3 mm inner diameter, more preferably a needle small than 0.25 mm inner diameter, even more preferably a needle smaller than 0.2 mm inner diameter, and most preferably a needle small than 0.16 mm inner diameter.

In another embodiment, the present invention relates to a medical delivery device comprising a polymeric prodrug or pharmaceutical composition comprising a polymeric prodrug of the present invention, for use in the prevention, diagnosis and/or treatment of a disease of the joint.

The present invention also relates to a polymeric prodrug or pharmaceutical composition comprising a polymeric prodrug, for the preparation of a medicament for the prevention, diagnosis and/or treatment of a disease of the joint.

The present invention also relates to a polymeric prodrug of the present invention for use in the prevention, diagnosis and/or treatment of a disease of the joint.

The present invention also relates to a method of preventing and/or treating a disease of the joint, wherein said method comprises the step of administering a therapeutically effective amount of a polymeric prodrug or pharmaceutical composition comprising a polymeric prodrug of the present invention to a patient in need thereof. Preferably, the polymeric prodrug or pharmaceutical composition comprising a polymeric prodrug is administered by intra-articular injection.

FIG. 1: Dexamethasone concentration in plasma after intraarticular injection of dexamethasone linker hydrogel prodrug 10c.

EXAMPLES

Materials and Methods

Amino 4-arm PEG 5 kDa was obtained from JenKem Technology, Beijing, P. R. China.

N-(3-maleimidopropyl)-21-amino-4,7,10,13,16,19-hexaoxa-heneicosanoic acid NHS ester (Mal-PEG6-NHS) was obtained from Celares GmbH, Berlin, Germany.

6-(S-Tritylmercapto)hexanoic acid was purchased from Polypeptide, Strasbourg, France.

Boc-4-aminobutanoic acid, boc-β-alanine, PyBOP and EDC.HCl were purchased from Novabiochem, Darmstadt, Germany.

Dexamethasone was obtained von Alfa Aesar,

NHS activated Carboxy-PEG 10 kDa was obtained from Rapp Polymere, Tübingen, Germany Modmoc-Chloride was ordered from Chemzone, Petaling Jaya, Malaysia IL-1ra (Anakinra, Kineret®, Swedish Orphan Biovitrum AB) ready to use syringes were obtained from a local pharmacy.

All other chemicals were from Sigma-ALDRICH Chemie GmbH, Taufkirchen, Germany.

15-Tritylthio-4,7,10,13-tetraoxa-pentadecanoic acid (Trt-S-PEG4-COOH) is obtained from Iris Biotech GmbH, Marktredwitz, Germany.

RP-HPLC Purification:

RP-HPLC was done on a 100×20 mm or 100×40 mm C18 ReproSil-Pur 300 ODS-3 5 μm column (Dr. Maisch, Ammerbuch, Germany) or a 30×150 mm C18 BEH 300 10 μm column (Waters) connected to a Waters 600 HPLC System and Waters 2487 Absorbance detector unless otherwise stated. Linear gradients of solution A (0.1% TFA or 0.01% HCl in $H_2O$) and solution B (0.1% TFA or 0.01% HCl in acetonitrile) were used. HPLC fractions containing product were pooled and lyophilized.

Flash Chromatography

Flash chromatography purifications were performed on an Isolera One system from Biotage AB, Sweden, using Biotage KP-Sil silica cartridges and n-heptane and ethyl acetate as eluents. Products were detected at 254 nm.

For hydrogel beads, syringes equipped with polyethylene frits were used as reaction vessels or for washing steps.

PBSTE buffer was prepared by solubilizing one PBS-Tween tablet (Calbiochem) and 5 mM EDTA in 1 L distilled water and adjusting the pH value to 7.40 with aqueous NaOH (4 N). The resulting solution was then filtered through 0.22 μm sterile bottle top filter (Nalgene).

Citrate buffer pH 6.5 was prepared by dissolving 7.5 mmol trisodium citrate, 140 mmol NaCl, 0.5 mmol EDTA disodium salt and 1.0 mg Polysorbate 80 in 950 mL water, adjusting the pH to pH 6.50 by addition of 1 N HCl and filling up with water to 1000 mL. Buffer was filtered sterile through 0.22 μm Nalgene bottle top filter.

Analytical ultra-performance LC(UPLC)-MS was performed on a Waters Acquity system equipped with a Waters BEH300 C18 column (2.1×50 mm, 1.7 μm particle size) coupled to a LTQ Orbitrap Discovery mass spectrometer from Thermo Scientific or a ZQ 4000 ESI (positive mode) instrument from Waters.

MS of PEG products showed a series of $(CH_2CH_2O)_n$ moieties due to polydispersity of PEG starting materials. For easier interpretation only one single representative m/z signal is given in the examples.

SEC-HPLC was performed on an Agilent 1260 system using a TSK-Gel G2000SWXL column from Tosoh Bioscience. Mobile Phase Buffer: 1.059 mM $KH_2SO_4$, 2.966 mM $Na_2HPO_4$ and 300 mM NaCl dissolved in water to 980 ml, adjusted to pH 7.40 and filled up to 1000 ml followed by addition of 100 ml absolute Ethanol. Flow rate: 0.5 ml/min, runtime 35 min, detector wavelength: 220 nm, reference wavelength: 360 nm, calibrated with IL-1ra standard solutions before each measurement.

IL-1ra concentration in solution was determined photometrically at 280 nm by using an extinction coefficient of 14077 $M^{-1}$ $cm^{-1}$ for IL1RA and 14202 $M^{-1}$ $cm^{-1}$ for oxidized IL1RA (internal disulfide)

Quantitative Amino Acid Analysis (QAAA)

An aliquot of hydrogel suspension in aqueous buffer is weighed into a 10 mL pressure tube. Internal standard solution containing aminobutyric acid and d8-valine is added and the solvents are evaporated. In addition to these samples, several standards are prepared from amino acid stock solutions (mixture of valine, leucine, isoleucine and phenylalanine) and the internal standard. To each tube a hydrolysis mixture (600 µL of 6 M HCl/TFA 2:1) and a stirring bar are added.

The samples are hydrolyzed for 30 min at 190° C. in the microwave. The hydrolysis solution is transferred to a 5 mL volumetric flask. The glass vial is rinsed with cooled 100 mM citrate buffer (pH=3.0) and the solution is added to the volumetric flask. The solution in the volumetric flask is neutralized with cooled 4 M NaOH and the volumetric flask is filled up to mark with 100 mM citrate buffer (pH=3.0).

Aliquots from the volumetric flasks are diluted 1:5 with a 1:1 mixture of 100 mM citrate buffer (pH=3.0) and 50 mM HFBA in water. After vortexing and centrifugation the supernatant is analyzed by LC-MS/MS.

LC-MS/MS is performed on an Agilent Technologies 1290 Infinity LC combined with an Agilent Technologies 6460 Triple Quad using a Waters Accq-Tag Ultra C18, 2.1×100 mm, 1.7 m column (0.36 mL/min, 45° C.). Eluent A: 0.2% aqueous HFBA Eluent B: 0.2% HFBA in methanol. A linear 15 min gradient 0.1-38% eluent B is used.

The amount of protein per sample is calculated by the averaged values obtained for valine, leucine, isoleucine and phenylalanine content.

The quantification of plasma dexamethasone concentrations was carried out by LC-MS/MS analysis using an Agilent 1290 UPLC coupled to an Agilent 6460 mass spectrometer via an ESI probe. Chromatography was performed on a Waters Acquity BEH C18 analytical column (100×2.1 mm I.D., 1.7 µm particle size) with pre-filter at a flow rate of 0.50 mL/min (T=45° C.). Water (UPLC grade) containing 0.1% formic acid was used as mobile phase A and acetonitrile (UPLC grade) with 0.1% formic acid as mobile phase B. The gradient system comprised a short isocratic step at the initial parameters of 20% B for 0.1 min followed by linear gradient steps from 20% B to 50% B in 3.9 min and from 50% to 99% in 1.0 min. Ion detection was performed in the multiple reaction monitoring (MRM) mode, monitoring the transition pairs at the m/z 393.2 precursor ions to the m/z 373.2 product ions for dexamethasone and m/z 397.2 precursor ions to the m/z 377.2 product ions for the internal standard (IS) D4-dexamethasone.

The thawed plasma samples (100 µL) were each spiked with 90 pg of D4-dexamethasone (10 µl of a methanolic-aqueous D4-dexamethasone solution c=900 pg/mL) and diluted with 4% phosphoric acid. For plasma matrix removal and analyte preconcentration the samples were subsequently extracted then by solid phase extraction (SPE) using Oasis HLB µElution 96-well plates (Waters). A two-step washing procedure with 100 µL of 2% phosphoric acid and 100 µL methanol/water 2:8 (v/v) (containing 0.1% formic acid), followed by an elution step with 2×50 µL methanol/water 9:1 (v/v) (containing 0.1% formic acid) into 96-well plates were applied for selective plasma matrix removal and quantitative extraction of dexamethasone and the internal standard. The eluates were transferred into vials and evaporated to dryness under a gentle nitrogen stream at 35° C. The residues at different time points were reconstituted in 50 µL of methanol/water 1:1 (v/v) and aliquots of 10 µL were injected into the UPLC-MS system.

Blank plasma samples were used to prepare calibrations standards: 100 L aliquots of pooled pre-dose plasma were spiked with different amounts of dexamethasone (30-6000 pg/mL) and the internal standard (900 pg/mL). The samples were processed and analyzed as described above. Calibration curves were acquired by plotting the peak area ratios of the MRM-signals of dexamethasone and D4-dexamethasone (IS) as a function of the analyte concentration. For the quantification of dexamethasone in plasma samples, weighted least-squares regression (1/x2) analysis of the standard curves was used (Agilent MassHunter quantification software).

Example 1

Synthesis of Backbone Reagent 1g

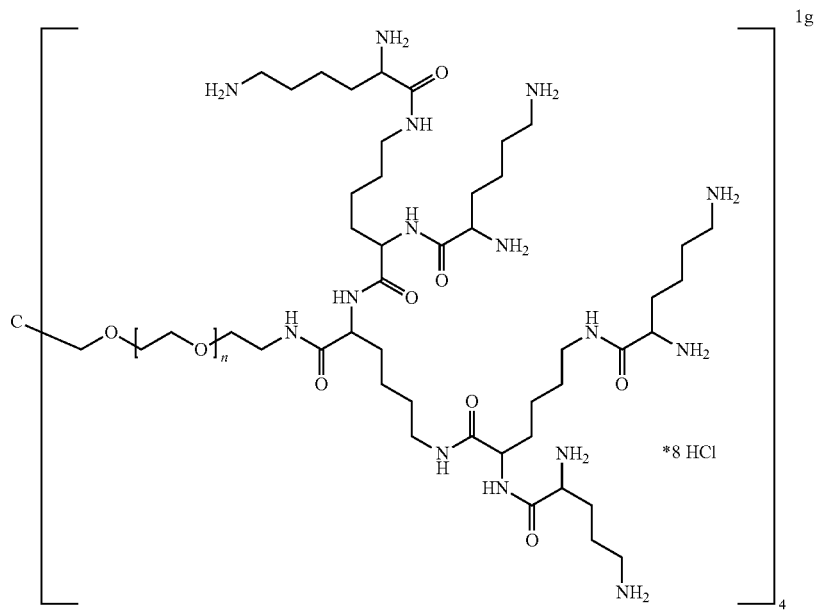

Backbone reagent 1g was synthesized from amino 4-arm PEG5000 1a according to following scheme:

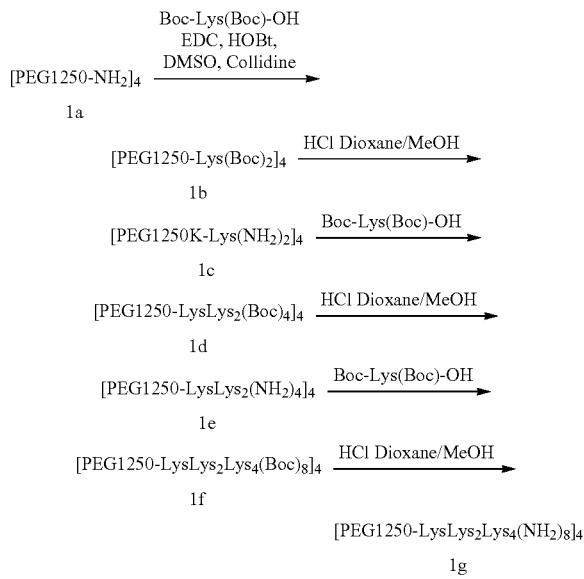

For synthesis of compound 1b, amino 4-arm PEG5000 1a (MW ca. 5200 g/mol, 5.20 g, 1.00 mmol, HCl salt) was dissolved in 20 mL of DMSO (anhydrous). Boc-Lys(Boc)-OH (2.17 g, 6.25 mmol) in 5 mL of DMSO (anhydrous), EDC HCl (1.15 g, 6.00 mmol), HOBt.H$_2$O (0.96 g, 6.25 mmol), and collidine (5.20 mL, 40 mmol) were added. The reaction mixture was stirred for 30 min at RT.

The reaction mixture was diluted with 1200 mL of DCM and washed with 600 mL of 0.1 N H$_2$SO$_4$ (2×), brine (1×), 0.1 M NaOH (2×), and 1/1 (v/v) brine/water (4×). Aqueous layers were reextracted with 500 mL of DCM. Organic phases were dried over Na$_2$SO$_4$, filtered and evaporated to give 6.3 g of crude product 1b as colorless oil. Compound 1b was purified by RP-HPLC.

Yield 3.85 g (59%) colorless glassy product 1b.

MS: m/z 1294.4=[M+5H]$^{5+}$ (calculated=1294.6).

Compound 1c was obtained by stirring of 3.40 g of compound 1b (0.521 mmol) in 5 mL of methanol and 9 mL of 4 N HCl in dioxane at RT for 15 min. Volatiles were removed in vacuo. The product was used in the next step without further purification.

MS: m/z 1151.9=[M+5H]$^{5+}$ (calculated=1152.0).

For synthesis of compound 1d, 3.26 g of compound 1c (0.54 mmol) were dissolved in 15 mL of DMSO (anhydrous). 2.99 g Boc-Lys(Boc)-OH (8.64 mmol) in 15 mL DMSO (anhydrous), 1.55 g EDC HCl (8.1 mmol), 1.24 g HOBt.H$_2$O (8.1 mmol), and 5.62 mL of collidine (43 mmol) were added. The reaction mixture was stirred for 30 min at RT.

Reaction mixture was diluted with 800 mL DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried with Na$_2$SO$_4$, filtered and evaporated to give a glassy crude product.

Product was dissolved in DCM and precipitated with cooled (−18° C.) diethylether. This procedure was repeated twice and the precipitate was dried in vacuo.

Yield: 4.01 g (89%) colorless glassy product 1d, which was used in the next step without further purification.

MS: m/z 1405.4=[M+6H]6+ (calculated=1405.4).

Compound 1e was obtained by stirring a solution of compound 1d (3.96 g, 0.47 mmol) in 7 mL of methanol and 20 mL of 4 N HCl in dioxane at RT for 15 min. Volatiles were removed in vacuo. The product was used in the next step without further purification.

MS: m/z 969.6=[M+7H]$^{7+}$ (calculated=969.7).

For the synthesis of compound 1f, compound 1e (3.55 g, 0.48 mmol) was dissolved in 20 mL of DMSO (anhydrous). Boc-Lys(Boc)-OH (5.32 g, 15.4 mmol) in 18.8 mL of DMSO (anhydrous), EDC HCl (2.76 g, 14.4 mmol), HOBt.H$_2$O (2.20 g, 14.4 mmol), and 10.0 mL of collidine (76.8 mmol) were added. The reaction mixture was stirred for 60 min at RT.

The reaction mixture was diluted with 800 mL of DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried over Na$_2$SO$_4$, filtered and evaporated to give crude product 1f as colorless oil.

Product was dissolved in DCM and precipitated with cooled (−18° C.) diethylther. This step was repeated twice and the precipitate was dried in vacuo.

Yield: 4.72 g (82%) colourless glassy product 1f which was used in the next step without further purification.

MS: m/z 1505.3=[M+8H]$^{8+}$ (calculated=1505.4).

Backbone reagent 1g was obtained by stirring a solution of compound 1f (MW ca. 12035 g/mol, 4.72 g, 0.39 mmol) in 20 mL of methanol and 40 mL of 4 N HCl in dioxane at RT for 30 min. Volatiles were removed in vacuo.

Yield: 3.91 g (100%), glassy product backbone reagent 1g.

MS: m/z 977.2=[M+9H]$^{9+}$ (calculated=977.4).

Alternative Synthetic Route for 1g

For synthesis of compound 1b, to a suspension of 4-Arm-PEG5000 tetraamine (1a) (50.0 g, 10.0 mmol) in 250 mL of iPrOH (anhydrous), boc-Lys(boc)-OSu (26.6 g, 60.0 mmol) and DIEA (20.9 mL, 120 mmol) were added at 45° C. and the mixture was stirred for 30 min.

Subsequently, n-propylamine (2.48 mL, 30.0 mmol) was added. After 5 min the solution was diluted with 1000 mL of MTBE and stored overnight at −20° C. without stirring. Approximately 500 mL of the supernatant were decanted and discarded. 300 mL of cold MTBE were added and after 1 min shaking the product was collected by filtration through a glass filter and washed with 500 mL of cold MTBE. The product was dried in vacuo for 16 h.

Yield: 65.6 g (74%) 1b as a white lumpy solid

MS: m/z 937.4=[M+7H]$^7$ (calculated=937.6).

Compound 1c was obtained by stirring of compound 1b from the previous step (48.8 g, 7.44 mmol) in 156 mL of 2-propanol at 4° C. A mixture of 196 mL of 2-propanol and 78.3 mL of acetylchloride was added under stirring within 1-2 min. The solution was stirred at 40° C. for 30 min and cooled to −30° C. overnight without stirring. 100 mL of cold MTBE were added, the suspension was shaken for 1 min and cooled for 1 h at −30° C. The product was collected by filtration through a glass filter and washed with 200 mL of cold MTBE. The product was dried in vacuo for 16 h.

Yield: 38.9 g (86%) 1c as a white powder

MS: m/z 960.1=[M+6H]6+ (calculated=960.2).

For synthesis of compound 1d, boc-Lys(boc)-OSu (16.7 g, 37.7 mmol) and DIPEA (13.1 mL, 75.4 mmol) were added to a suspension of 1c from the previous step (19.0 g, 3.14 mmol) in 80 ml 2-propanol at 45° C. and the mixture was stirred for 30 min at 45° C. Subsequently, n-propylamine (1.56 mL, 18.9 mmol) was added. After 5 min the solution was precipitated with 600 mL of cold MTBE and centrifuged (3000 min$^{-1}$, 1 min) The precipitate was dried in vacuo for 1 h and dissolved in 400 mL THF. 200 mL of diethyl ether were added and the product was cooled to −30° C. for 16 h without stirring. The suspension was filtered through a glass filter and washed with 300 mL cold MTBE. The product was dried in vacuo for 16 h.

Yield: 21.0 g (80%) 1d as a white solid

MS: m/z 1405.4=[M+6H]6+ (calculated=1405.4).

Compound 1e was obtained by dissolving compound 1d from the previous step (15.6 g, 1.86 mmol) in 3 N HCl in methanol (81 mL, 243 mmol) and stirring for 90 min at 40° C. 200 mL of MeOH and 700 mL of iPrOH were added and the mixture was stored for 2 h at −30° C. For completeness of crystallization, 100 mL of MTBE were added and the suspension was stored at −30° C. overnight. 250 mL of cold MTBE were added, the suspension was shaken for 1 min and filtered through a glass filter and washed with 100 mL of cold MTBE.

The product was dried in vacuo.

Yield: 13.2 g (96%) 1e as a white powder

MS: m/z 679.1=[M+10H]$^{10+}$ (calculated=679.1).

For the synthesis of compound 1f, boc-Lys(boc)-OSu (11.9 g, 26.8 mmol) and DIPEA (9.34 mL, 53.6 mmol) were added to a suspension of 1e from the previous step, (8.22 g, 1.12 mmol) in 165 ml 2-propanol at 45° C. and the mixture was stirred for 30 min. Subsequently, n-propylamine (1.47 mL, 17.9 mmol) was added. After 5 min the solution was cooled to −18° C. for 2 h, then 165 mL of cold MTBE were added, the suspension was shaken for 1 min and filtered through a glass filter. Subsequently, the filter cake was washed with 4×200 mL of cold MTBE/iPrOH 4:1 and 1×200 mL of cold MTBE. The product was dried in vacuo for 16 h.

Yield: 12.8 g, MW (90%) 1f as a pale yellow lumpy solid

MS: m/z 1505.3=[M+8H]$^{8+}$ (calculated=1505.4).

Backbone reagent 1g was obtained by dissolving 4Arm-PEG5 kDa (-LysLys$_2$Lys$_4$(boc)$_8$)$^4$ (1f) (15.5 g, 1.29 mmol) in 30 mL of MeOH and cooling to 0° C. 4 N HCl in dioxane (120 mL, 480 mmol, cooled to 0° C.) was added within 3 min and the ice bath was removed. After 20 min, 3 N HCl in methanol (200 mL, 600 mmol, cooled to 0° C.) was added within 15 min and the solution was stirred for 10 min at room temperature. The product solution was precipitated with 480 mL of cold MTBE and centrifuged at 3000 rpm for 1 min. The precipitate was dried in vacuo for 1 h and redissolved in 90 mL of MeOH, precipitated with 240 mL of cold MTBE and the suspension was centrifuged at 3000 rpm for 1 min. The product 1g was dried in vacuo Yield: 11.5 g (89%) as pale yellow flakes.

MS: m/z 1104.9=[M+8H]$^{8+}$ (calculated=1104.9).

Synthesis of Backbone Reagent (1h)

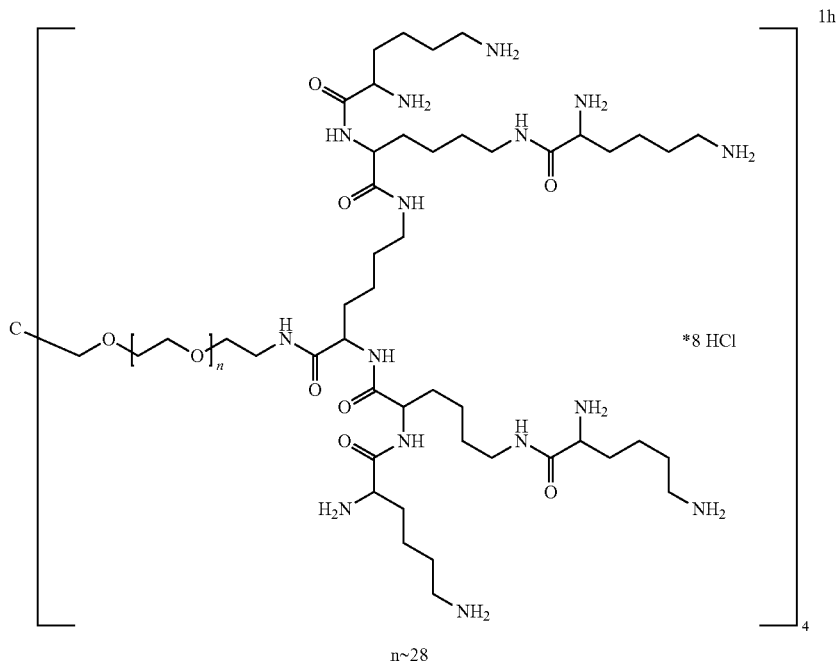

Backbone reagent 1h was synthesized as described for 1g, except for the use of Boc-D-Lys(Boc)-OSu instead of Boc-Lys(Boc)-OSu.

Yield: 12.99 g (76%) as white foam.

MS: m/z 910.50=[M+10H]$^{10+}$ (calculated=910.57).

Example 2

Synthesis of Crosslinker Reagent 2d

Crosslinker reagent 2d was prepared from adipic acid mono benzyl ester (English, Arthur R. et al., *Journal of Medicinal Chemistry*, 1990, 33(1), 344-347) and PEG2000 according to the following scheme:

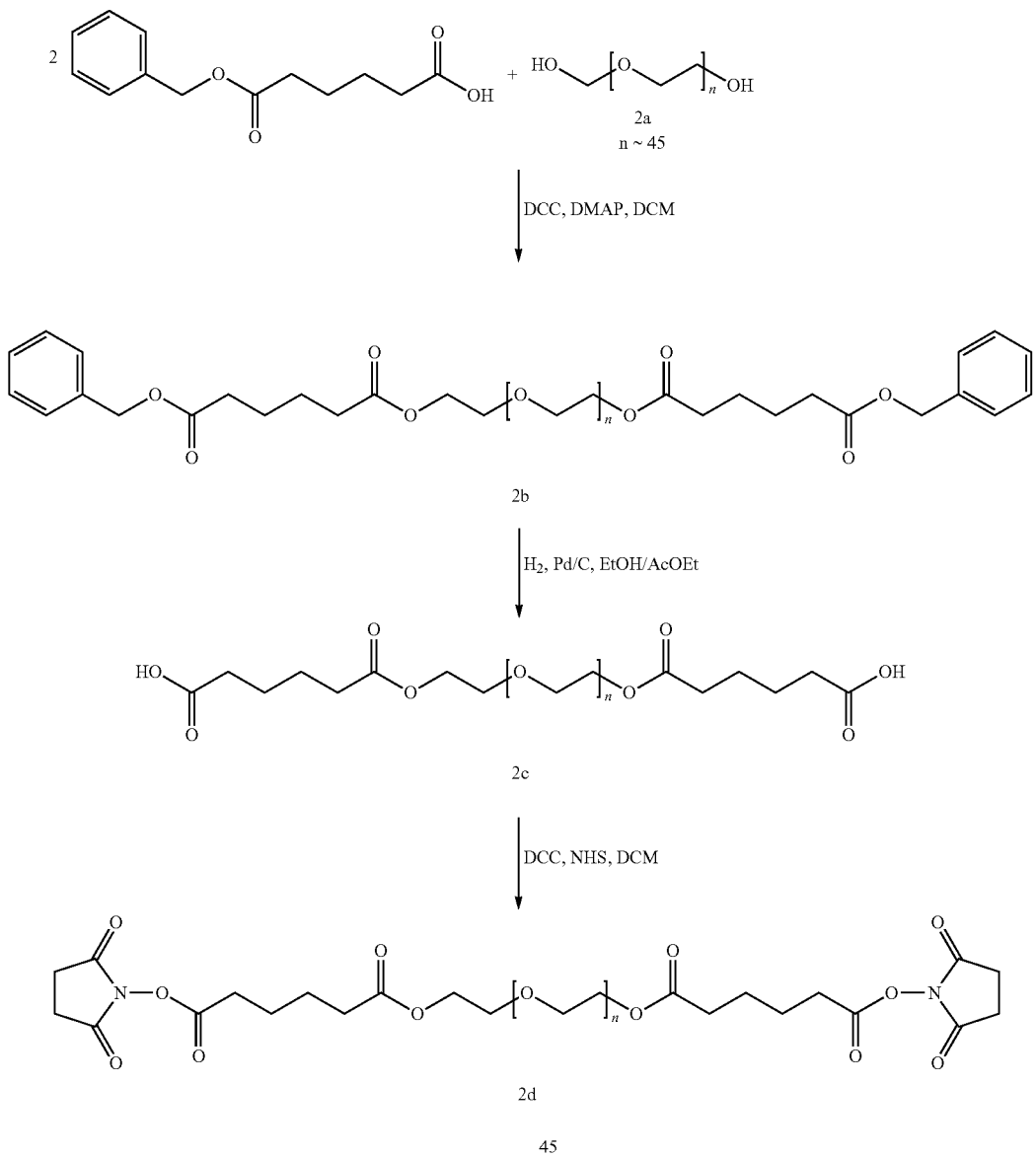

A solution of PEG 2000 (2a) (11.0 g, 5.5 mmol) and benzyl adipate half-ester (4.8 g, 20.6 mmol) in DCM (90.0 mL) was cooled to 0° C. Dicyclohexylcarbodiimide (4.47 g, 21.7 mmol) was added followed by a catalytic amount of DMAP (5 mg) and the solution was stirred and allowed to reach room temperature overnight (12 h). The flask was stored at +4° C. for 5 h. The solid was filtered and the solvent completely removed by distillation in vacuo. The residue was dissolved in 1000 mL 1/1(v/v) diethyl ether/ethyl acetate and stored at RT for 2 hours while a small amount of a flaky solid was formed. The solid was removed by filtration through a pad of Celite®. The solution was stored in a tightly closed flask at −30° C. in the freezer for 12 h until crystallisation was complete. The crystalline product was filtered through a glass frit and washed with cooled diethyl ether (−30° C.). The filter cake was dried in vacuo.

Yield: 11.6 g (86%) 2b as a colorless solid. The product was used without further purification in the next step.

MS: m/z 813.1=[M+3H]$^{3+}$ (calculated=813.3)

In a 500 mL glass autoclave PEG2000-bis-adipic acid-bis-benzyl ester 2b (13.3 g, 5.5 mmol) was dissolved in ethyl acetate (180 mL) and 10% Palladium on charcoal (0.4 g) was added. The solution was hydrogenated at 6 bar, 40° C. until consumption of hydrogen had ceased (5-12 h). Catalyst was removed by filtration through a pad of Celite® and the solvent was evaporated in vacuo.

Yield: 12.3 g (quantitative) 2c as yellowish oil. The product was used without further purification in the next step.

MS: m/z 753.1=[M+3H]$^{3+}$ (calculated=753.2)

A solution of PEG2000-bis-adipic acid half ester 2c (9.43 g, 4.18 mmol), N-hydroxysuccinimide (1.92 g, 16.7 mmol) and dicyclohexylcarbodiimide (3.44 g, 16.7 mmol) in 75 mL of DCM (anhydrous) was stirred over night at room temperature. The reaction mixture was cooled to 0° C. and precipitate was filtered off. DCM was evaporated and the residue was recrystallized from THF.

Yield: 8.73 g (85%) crosslinker reagent 2d as colorless solid.

MS: m/z 817.8=[M+3H]$^{3+}$ (calculated=817.9 g/mol).

Synthesis of 2e
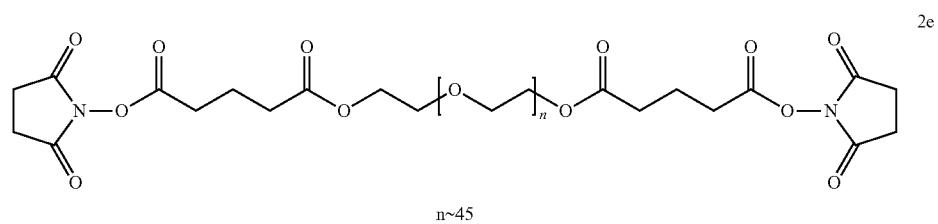
2e
n~45
2e was synthesized as described for 2d except for the use of glutaric acid instead of adipic acid
MS: m/z 764.4=[M+3H]3+ (calculated=764.5).
Crosslinker reagent 2k was prepared from isopropylmalonic acid monobenzyl ester and PEG3300 according to the following scheme:
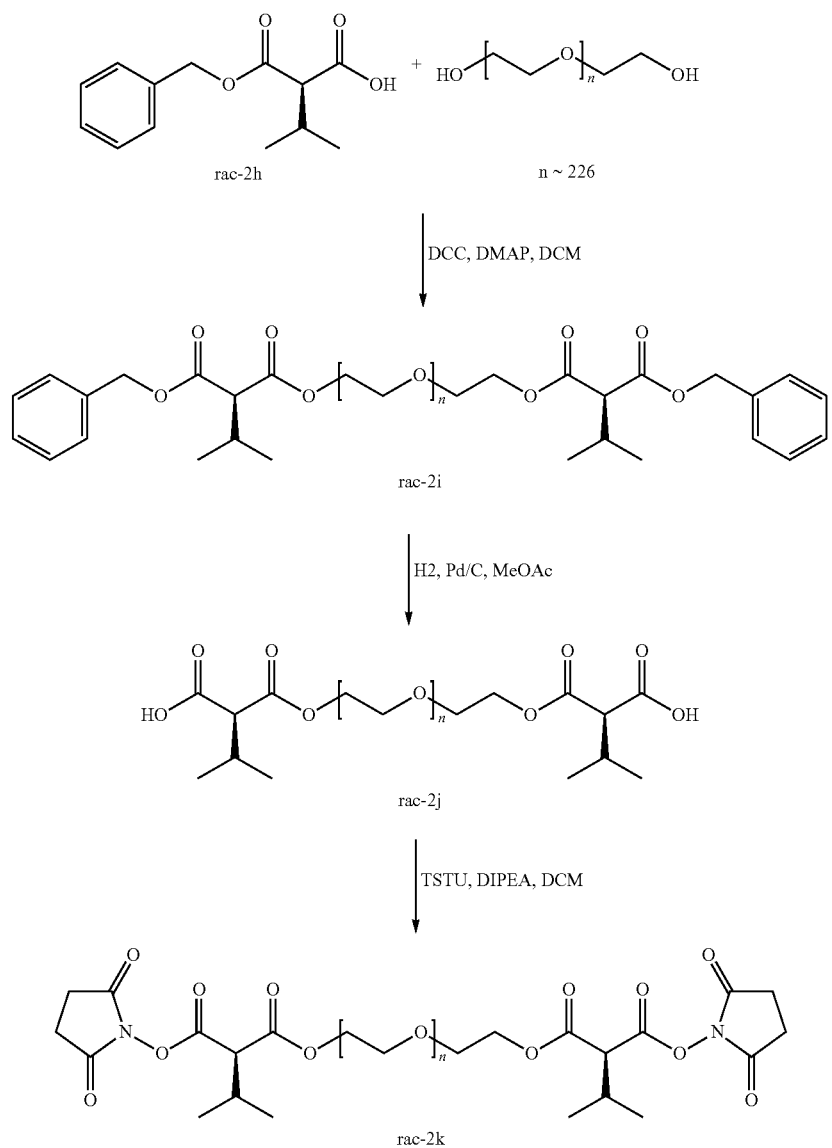

For the synthesis of isopropylmalonic acid monobenzyl ester rac-2h, isopropylmalonic acid (35.0 g, 239 mmol), benzyl alcohol (23.3 g, 216 mmol) and DMAP (1.46 g, 12.0 mmol) were dissolved in 100 mL acetonitrile. Mixture was cooled to 0° C. with an ice bath. A solution of DCC (49.4 g, 239 mmol) in 150 mL acetonitrile was added within 15 min at 0° C. The ice bath was removed and the reaction mixture was stirred over night at room temperature, then the solid was filtered off. The filtrate was evaporated at 40° C. in vacuo and the residue was dissolved in 300 mL MTBE. This solution was extracted with 2×300 mL sat. aqueous $NaHCO_3$ solution, then the combined aqueous phases were acidified to pH=1-3 using 6 N hydrochloric acid. The resulting emulsion was extracted with 2×300 mL MTBE and the solvent was evaporated. The combined organic phases were washed with 200 mL sat. aqueous NaCl and dried over $MgSO_4$. The product was purified on 340 g silica using ethyl acetate/heptane (10:90→20:80) as eluent. The eluent was evaporated and the residue was dried in vacuo over night.

Yield 9.62 g (17%) colorless oil rac-2h.

MS: m/z 237.11=$[M+H]^+$ (calculated=237.11).

For synthesis of compound 2i, isopropylmalonic acid monobenzyl ester rac-2h (5.73 g, 24.24 mmol) and PEG3300 (20.0 g, 6.06 mmol) were dissolved in 110 mL dichloromethane and cooled with an ice bath. A solution of DCC (5.00 g, 24.24 mmol) and DMAP (37 mg, 0.30 mmol) in 20 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 70 mL dichloromethane and diluted with 800 mL MTBE at room temperature. The mixture was stored over night at −20° C. The precipitate was collected by filtration through a glass filter Por. 3, and washed with 650 mL of cooled MTBE (−20° C.). The product was dried in vacuo over night. Precipitation procedure was repeated. The product was dried in vacuo over night.

Yield 20.49 g (90%) white powder rac-2i.

MS: m/z 671.39=$[M+6H]6+$ (calculated=671.47).

For synthesis of compound rac-2j, compound rac-2i (20.38 g, 5.42 mmol) was dissolved in methyl acetate (130 mL) and 242 mg of palladium on charcoal (10%) was added. Under a hydrogen atmosphere of ambient pressure, the mixture was stirred overnight at room temperature. The reaction mixture was filtered through a pad of celite and the filtrate was evaporated and dried in vacuo over night.

Yield 18.24 g (94%) glassy solid rac-2j.

MS: m/z 641.38=$[M+6H]6+$ (calculated=641.43).

For synthesis of compound rac-2k, compound rac-2j (11.98 g, 3.35 mmol) and TSTU (4.03 g, 13.39 mmol) were dissolved in 145 mL dichloromethane at room temperature. Then DIPEA (1.73 g, 13.39 mmol) was added and the mixture was stirred for 45 min. The resulting suspension was filtered and the filtrate was washed with 175 mL of a 0.5 M phosphate buffer pH=6.5. Organic phase was diluted with 350 mL ethyl acetate. The organic phase was dried over $MgSO_4$ and the solvent was evaporated in vacuo. The residue was dissolved in 100 mL toluene, diluted with 25 mL MTBE at room temperature and stored over night at −20° C. The precipitate was collected by filtration through a glass filter Por. 3, and washed with 600 mL of cooled MTBE (−20° C.). The product was dried in vacuo over night.

Yield 8.50 g (67%) white powder rac-2k.

MS: m/z 673.72=$[M+6H]6+$ (calculated=673.77).

Example 3

Preparation of Hydrogel Beads 3a, 3b, 3c and 3d Containing Free Amino Groups

Preparation of hydrogel beads 3a containing free amino groups

A solution of 1200 mg 1g and 3840 mg 2e in 28.6 mL DMSO was added to a solution of 425 mg Arlacel P135 (Croda International Plc) in 100 mL heptane. The mixture was stirred at 650 rpm with a propeller stirrer for 10 min at 25° C. to form a suspension in a 250 ml reactor equipped with baffles. 4.3 mL TMEDA was added to effect polymerization. After 2 h, the stirrer speed was reduced to 400 rpm and the mixture was stirred for additional 16 h. 6.6 mL of acetic acid were added and then after 10 min 50 mL of water and 50 mL of saturated aqueous sodium chloride solution were added. After 5 min, the stirrer was stopped and the aqueous phase was drained.

For bead size fractionation, the water-hydrogel suspension was wet-sieved on 75, 50, 40, 32 and 20 μm mesh steel sieves. Bead fractions that were retained on the 32, 40, and 50 μm sieves were pooled and washed 3 times with water, 10 times with ethanol and dried for 16 h at 0.1 mbar to give 3a as a white powder.

Amino group content of hydrogel was determined by coupling of a fmoc-amino acid to the free amino groups of the hydrogel and subsequent fmoc-determination as described by Gude, M., J. Ryf, et al. (2002) *Letters in Peptide Science* 9(4): 203-206.

The amino group content of 3a was determined to be between 0.11 and 0.16 mmol/g.

Preparation of Hydrogel Beads 3b, Containing Free Amino Groups

A solution of 2850 mg 1g and 3705 mg 2d in 32.81 mL DMSO was added to a solution of 505 mg Arlacel P135 (Croda International Plc) in 120 mL heptane. The mixture was stirred at 800 rpm with a propeller stirrer for 10 min at 25° C. to form a suspension in a 250 ml reactor equipped with baffles. 9.51 mL TMEDA was added to effect polymerization. After 2 h, the stirrer speed was reduced to 400 rpm and the mixture was stirred for additional 16 h. 14.6 mL of acetic acid were added and then after 10 min 50 mL of water and 50 mL of saturated aqueous sodium chloride solution were added. After 5 min, the stirrer was stopped and the aqueous phase was drained.

For bead size fractionation, the water-hydrogel suspension was wet-sieved on 75, 50, 40, 32 and 20 μm mesh steel sieves. Bead fractions that were retained on the 32, 40, and 50 μm sieves were pooled and washed 3 times with water, 10 times with ethanol and dried for 16 h at 0.1 mbar to give 3b as a white powder.

Preparation of Hydrogel Beads 3c, Containing Free Amino Groups 3c was synthesized according to the same procedure except for the use of 1h instead of 1g.

The amino group content of 3b and 3c was found to be 0.7-1.0 mmol/g.

Preparation of Hydrogel Beads 3d, Containing Free Amino Groups (PEG-Modified Hydrogel)

A suspension of hydrogel 3c in DMSO corresponding to 460 mg dried hydrogel (425 µmol, 1 eq) was filled into a syringe equipped with a polyethylene frit and washed six times with DMSO. A solution of PEG reagent (NHS activated Carboxy-PEG 10 kDa, 850 mg, 85 µmol, 0.2 eq, RAPP Polymere, Tübingen, Germany) in 8 mL DMSO and a 1.5 mL DMSO-solution of TMEDA (127 µL, 850 µmol, 2 eq) were added and the syringe was shaken for 22 h at RT. The PEG modified hydrogel 3d was then washed 10 times with 10 mL DMSO and aliquots were sampled for determination of free amino group content. The hydrogel suspension was stored at 4° C.

The amino group content of 3d was found to be 0.42-0.46 mmol/g.

3e was prepared as described for 3a except for the use of a 1 L reactor with 100 mm diameter, 400 mL undecane, 1000 mg 1h, 5698 mg rac-2k, 60.3 g DMSO, 595 mg Cithrol™ DPHS, 4.5 mL TMEDA, and 6.7 mL acetic acid, yielding 1.24 g (bead fraction on 100 µm sieve) 3e as a white powder.

The amino group content of 3e was found to be 0.068 mmol/g.

3f was prepared as described for 3a except for the use of 740 mg 1h, 3362 mg rac-2k, 36.9 g DMSO, 365 mg Cithrol™ DPHS, 3.3 mL ml TMEDA, and 5.1 mL acetic acid, yielding 950 mg (bead fraction on 75 µm sieve) 3f as a white powder.

The amino group content of 3f was found to be 0.179 mmol/g.

Example 4

Preparation of Maleimide Functionalized Hydrogel Suspension 4 and Determination of Maleimide Substitution

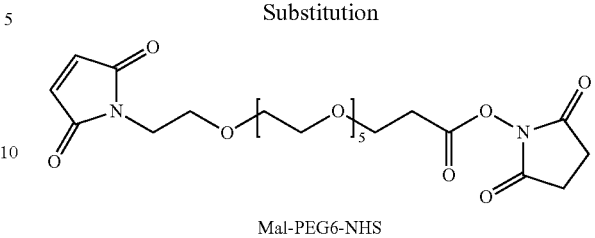

Mal-PEG6-NHS

Hydrogel 3a was pre-washed with 99/1 (v/v) DMSO/DIPEA, washed with DMSO and incubated for 45 min with a solution of Mal-PEG6-NHS (2.0 eq relative to theoretical amount of amino groups on hydrogel) in DMSO. Hydrogel were washed five times with DMSO and five times with pH 3.0 succinate (20 mM, 1 mM EDTA, 0.01% Tween-20). The sample was washed three times with pH 6.0 sodium phosphate (50 mM, 50 mM ethanolamine, 0.01% Tween-20) and incubated in the same buffer for 1 h at RT. Then hydrogel was washed five times with pH 3.0 sodium succinate (20 mM, 1 mM EDTA, 0.01% Tween-20) and kept in that buffer to yield maleimide functionalized hydrogel 4 in suspension.

For determination of maleimide content, an aliquot of hydrogel 4 was washed three times with water and ethanol each. The aliquot was dried under reduced pressure and the weight of hydrogel in the aliquot was determined. Another aliquot of hydrogel 4 was reacted with excess mercaptoethanol (in 50 mM sodium phosphate buffer, 30 min at RT), and mercaptoethanol consumption was detected by Ellman test (Ellman, G. L. et al., *Biochem. Pharmacol.*, 1961, 7, 88-95). A maleimide content of 0.10-0.15 mmol/g dried hydrogel was calculated.

Example 5

Preparation of Betamethasone Linker Reagent 5

Betamethasone linker reagent 5 is synthesized according to the following scheme:

21-Glycyl-betamethasone is prepared according to the literature (Benedini, Francesca; Biondi, Stefano; Ongini, Ennio, PCT Int. Appl. (2008), WO 2008095806 A1 20080814). To a solution of 21-glycyl-betamethasone hydrochloride (MW 486 g/mol, 600 mg, 1.2 mmol) in methylene chloride (dry, molecular sieve, 40 ml), Trt-S-PEG4-COOH (MW 480.6 g/mol, 960 mg, 2.0 mmol), EDC.HCl (191.7 g/mol, 383 mg, 2.0 mmol) and DIEA (129.2 g/mol, d 0.742 mg/mL, 0.7 ml, 4 mmol) are added. The reaction is stirred at room temperature for 24 h. The solution is treated with a 5% solution of $H_3PO_4$ (50 ml). The organic layer is dried over sodium sulfate and concentrated under reduced pressure. The residue is dissolved in 2 mL dichloro methane and 8 mL HFIP. 0.4 mL TES are added and the reaction is stirred at room temperature for 1 h. Volatiles are removed under reduced pressure and 5 is purified by RP-HPLC.

Example 6

Synthesis of Betamethasone Linker Hydrogel 6

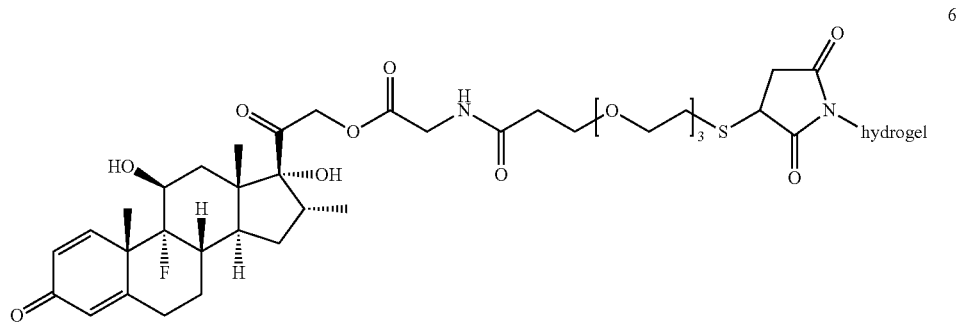

A suspension of maleimide functionalized hydrogel 4 in pH 3.0 succinate buffer (20 mM, 1 mM EDTA, 0.01% Tween-20)/acetonitrile 1/2 (v/v), (corresponding to 250 mg dried hydrogel, maleimide loading of 0.1 mmol/g dried hydrogel) is filled into a syringe equipped with a filter frit. The hydrogel is washed ten times with 2/1 (v/v) acetonitrile/water containing 0.1% TFA (v/v). A solution of betamethasone linker reagent 6 (MW 669.8 g/mol, 18.5 mg, 27.5 µmol) in 2/1 (v/v) acetonitrile/water containing 0.1% TFA (3.7 mL) is drawn up and shaken for 2 min at RT to obtain an equilibrated suspension. 334 µL phosphate buffer (pH 7.4, 0.5 M) is added and the syringe is agitated at RT. Consumption of thiol is monitored by Ellman test. The hydrogel is washed 10 times with 1/1 (v/v) acetonitrile/water containing 0.1% TFA (v/v).

Mercaptoethanol (47 µL) is dissolved in 1/1 (v/v) acetonitrile/water plus 0.1% TFA (3 mL) and phosphate buffer (0.5 mL, pH 7.4, 0.5 M). The solution is drawn into the syringe and the syringe is agitated for 30 min at RT. Hydrogel is washed ten times with 1/1 (v/v) acetonitrile/water plus 0.1% TFA and ten times with sterile succinate buffer (10 mM, 46 g/L mannitol, 0.05% Tween-20, adjusted to pH 5.0 with 5 M NaOH). Volume is adjusted to 5 mL to yield 50 mg/mL betamethasone linker hydrogel 6 as suspension in succinate buffer. Betamethasone content is determined by thiol consumption during reaction (Ellman test).

Example 7

Release Kinetics In Vitro

An aliquot of betamethasone linker hydrogel 6 is transferred in a syringe equipped with a filter frit and washed 5 times with pH 7.4 phosphate buffer (60 mM, 3 mM EDTA, 0.01% Tween-20). The hydrogel is suspended in the same buffer and incubated at 37° C. At defined time points (after 1-7 days incubation time each) the supernatant is exchanged and liberated betamethasone is quantified by RP-HPLC at 215 nm. UV-signals correlating to liberated betamethasone are integrated and plotted against incubation time.

Curve-fitting software is applied to estimate the corresponding halftime of release.

Example 8

Pharmacokinetics, Pharmacodymamics and Local Tolerably of Betamethasone after Intra-Articular Injection of Betamethasone Linker Hydrogel in Antigen Induced Arthritic Rabbit Arthritis is induced in rabbit joints by the ovalbumin method (Horisawa E, Hirota T, Kawazoe S, Yamada J, Yamamoto H, Takeuchi H, Kawashima Y. *Prolonged Anti-Inflammatory Action of DL-Lactide/Glycolide Copolymer Nanospheres Containing Betamethasone Sodium Phosphate for an Intra-Articular Delivery System in Antigen-Induced Arthritic Rabbit*, Pharm Res. 2002 April; 19(4):403-10.). 14 male New Zealand White rabbits are immunized by intradermal injection of Freud's Complete Adjuvant containing 5 mg ovalbumin/mL. At three weeks after immunization the arthritis is induced in the left knees by injecting 0.5 mL of saline containing 5 mg of ovalbumin. Simultaneously 200 µl betamethasone linker hydrogel suspension 6 containing 3 mg betamethasone are administered into the articular joint cavity. Control animals receive suspension buffer. Two animals each are euthanized 4 h and 1, 3, 7, 14, 28 and 42 days after the joint challenge. Whole blood is collected via the medial ear artery or cardiac bleed under anesthesia. Synovial fluid is collected from both knees. Betamethasone in plasma and synovial fluid is quantified by liquid chromatography-tandem mass spectrometry according to literature (Pereira Ados S, Oliveira L S, Mendes G D, Gabbai J J, De Nucci G. *Quantification of betamethasone in human plasma by liquid chromatography-tandem mass spectrometry using atmospheric pressure photoionization in negative mode*, J Chromatogr B Analyt Technol Biomed Life Sci. 2005 Dec. 15; 828(1-2):27-32.). Reduction in joint swelling and surface skin temperature, as well as cartilage quality and histological evaluation for biocompatibility is performed according to literature. (Horisawa E, Hirota T, Kawazoe S, Yamada J, Yamamoto H, Takeuchi H, Kawashima Y. *Prolonged anti-inflammatory action of DL-lactide/glycolide copolymer nanospheres containing betamethasone sodium phosphate for an intra-articular delivery system in antigen-induced arthritic rabbit*, Pharm Res. 2002 April; 19(4):403-10).

Example 9

Preparation of Dexamethasone Linker Reagents 7a, 7b, and 7c

Dexamethasone linker reagents 7a, 7b and 7c were synthesized according to the following scheme:

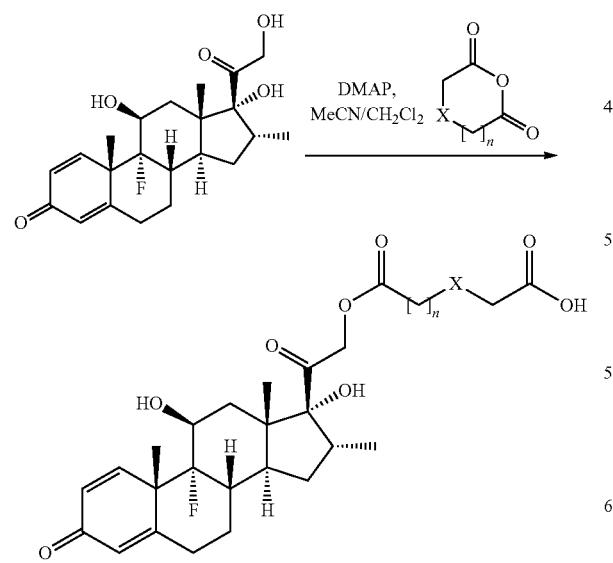

7a: n = 0, X = CH$_2$
7b: n = 1, X = CH$_2$
7c: n = 1, X = O

General Procedure A for the Synthesis of Dexamethasone Dicarboxylic Acid Hemiesters Dexamethasone (1 eq) is dissolved in a dichloromethane/acetonitrile solution (5/1, v/v, dexamethasone concentration 5 mg/mL) and cyclic anhydride (4 eq) and DMAP (2 eq) are added. The reaction mixture is allowed to stir at RT for 2 h and volatiles are then removed under reduced pressure. The residue is taken up in a water/acetonitrile (1/1, v/v)+0.1% TFA solution and purified by RP-HPLC. The collected fractions are lyophilized to afford the desired product as a white amorphous solid.

Synthesis of Dexamethasone Linker Reagent 7a

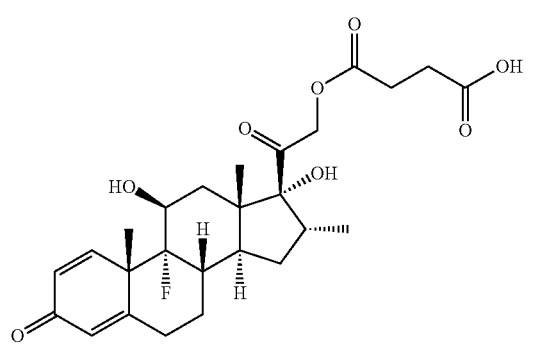

7a was synthesized from 100 mg dexamethasone according to the general procedure A by using succinic anhydride.
Yield: 123 mg (0.250 mmol, 98%).
MS: m/z 493.27=[M+H]$^+$ (MW calculated=492.22).

Synthesis of Dexamethasone Linker Reagent 7b

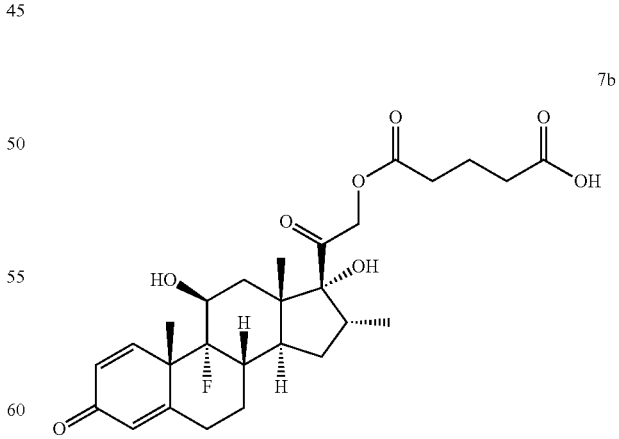

7b was synthesized from 40 mg dexamethasone according to the general procedure A by using glutaric anhydride.
Yield: 37 mg (0.073 mmol, 72%).
MS: m/z 507.29=[M+H]$^+$ (MW calculated=506.23).

Synthesis of Dexamethasone Linker Reagent 7c
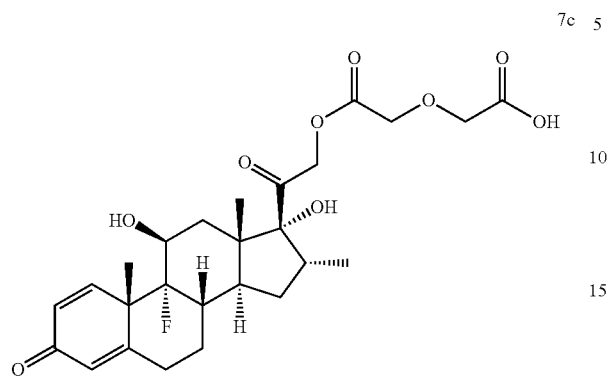
7c was synthesized from 80 mg dexamethasone according to the general procedure A by using diglycolic anhydride.
Yield: 93 mg (0.183 mmol, 90%).
MS: m/z 509.25=[M+H]$^+$ (MW calculated=508.21).
Example 10
Preparation of Dexamethasone Linker Reagents 8a, 8b and 8c
Dexamethasone linkers 8a, 8b, and 8c were synthesized according to the following scheme:
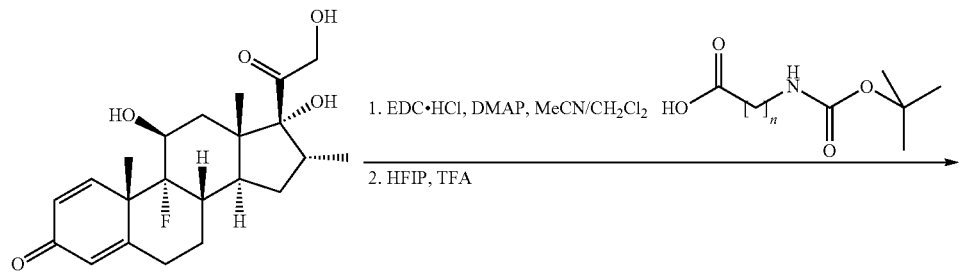
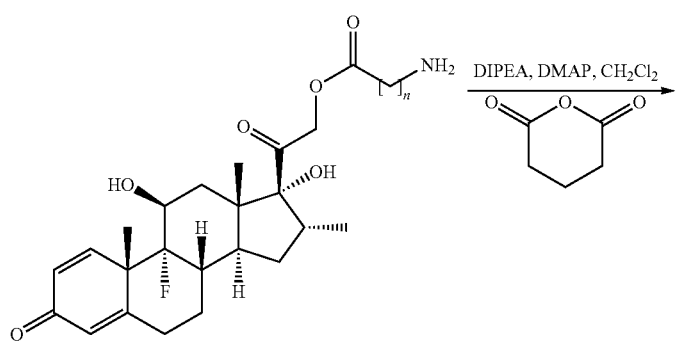

-continued

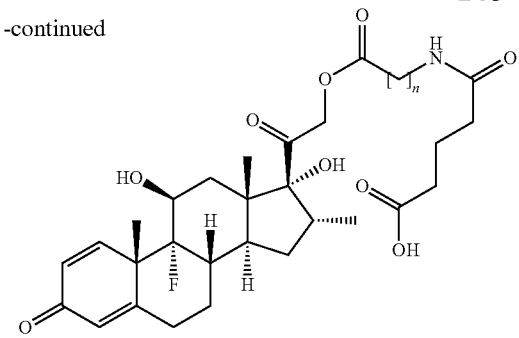

8a: n = 1
8b: n = 2
8c: n = 3

General Procedure B for Synthesis of Dexamethasone Linker Reagents

Dexamethasone (1 eq) is dissolved in a dichloromethane/acetonitrile (6/1, v/v) solution (dexamethasone concentration 8 mg/mL) and Boc-protected amino acid (1.5 eq), DMAP (2.5 eq) and EDC.HCL (2.5 eq) are successively added. The reaction mixture is allowed to stir for 1 h at RT and diluted with dichloromethane. The solution is washed three times with an aqueous hydrochloric acid solution (0.1 N) and once with brine. The organic layer is then dried over $Na_2SO_4$, filtered and volatiles are removed in vacuo. The residue is then taken up in a HFIP/TFA (1/1, v/v) solution and the resulting mixture is allowed to stir at RT for 30 min. The volatiles are removed under reduced pressure and the residue is dissolved again in dichloromethane. DIPEA (3 eq), DMAP (3 eq) and glutaric anhydride (3 eq) are then added and the resulting mixture is stirred for 2 h at RT. The reaction mixture is evaporated under reduced pressure and the residue is taken up in a water/acetonitrile (1/1, v/v) solution. Linker reagent is purified by RP-HPLC and subsequent lyophilization of the collected fractions gives the desired dexamethasone linker as a white amorphous solid.

Synthesis of Dexamethasone Linker Reagent 8a

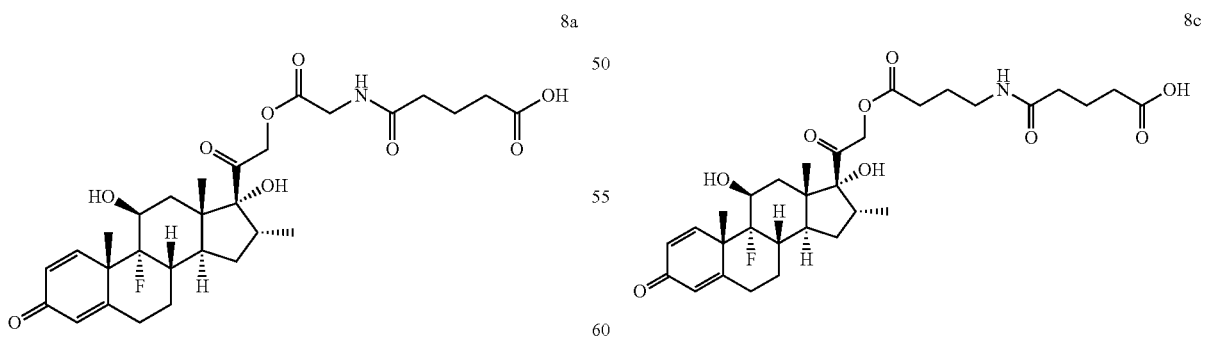

8a was synthesized from 150 mg dexamethasone according to the general procedure B by using Boc-glycine as amino acid.

Yield: 160 mg (0.284 mmol, 74%).

MS: m/z 564.34=[M+H]$^+$ (MW calculated=563.25).

Synthesis of Dexamethasone Linker Reagent 8b

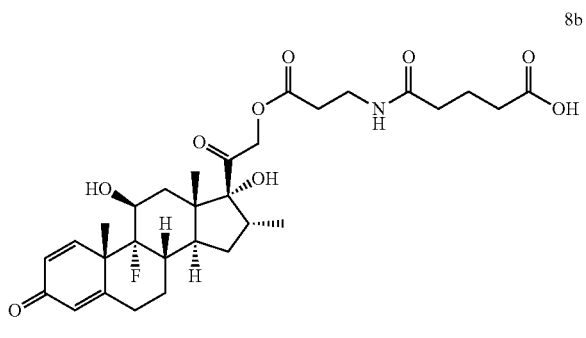

8b was synthesized from 1.4 g dexamethasone according to the general procedure B by using Boc-β-alanine as amino acid.

Yield: 1.593 g (2.758 mmol, 77%).

MS: m/z 578.19=[M+H]$^+$ (MW calculated=577.27).

Synthesis of Dexamethasone Linker Reagent 8c 8c was synthesized from 130 mg dexamethasone according to the general B by using γ-(Boc-amino)butyric acid as amino acid.

Yield: 160 mg (0.270 mmol, 82%).

MS: m/z 592.26=[M+H]$^+$ (MW calculated=591.28).

Example 11

Synthesis of Dexamethasone Linker Hydrogel Prodrugs 9a, 9b and 9c

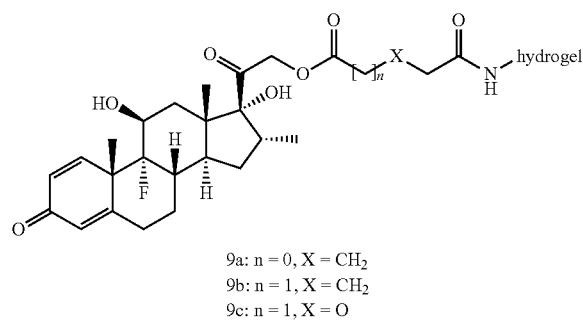

9a: n = 0, X = CH$_2$
9b: n = 1, X = CH$_2$
9c: n = 1, X = O

General Procedure C for Dexamethasone Linker Hydrogel Prodrug Synthesis

Hydrogel 3b (1 eq, amine content) is weighed into a syringe equipped with a polyethylene frit, washed five times with DMF and agitated for 2 h with 1.3 eq of dexamethasone linker reagent, 1.5 eq of PyBOP and 4 eq of DIPEA in DMF (approx. 60 mg hydrogel/mL DMF). Dexamethasone linker hydrogel prodrug is then washed with DMF (10 times), dichloromethane (10 times) and ethanol (10 times) and dried in vacuo.

Dexamethasone linker hydrogel prodrugs 9a, 9b and 9c were synthesized according to general procedure C by using dexamethasone linker reagent 7a, 7b and 7c, respectively.

Dexamethasone loading was calculated based on hydrogel weight increase after conjugation.

A dexamethasone loading of 18-23% (weight dexamethasone/total weight of dexamethasone linker hydrogel) was obtained

Example 12

Synthesis of Dexamethasone Linker Hydrogel Prodrugs 10a, 10b, 10c and 10d

General Protocol D for Dexamethasone Linker Hydrogel Prodrug Synthesis

Hydrogel 3b (1 eq amine content) is weighed into a syringe equipped with a polyethylene frit, washed five times with DMF and agitated for 2 h with 1.5 eq of dexamethasone linker reagent, 2.5 eq of PyBOP and 4 eq of DIPEA in DMF (60 mg hydrogel/mL DMF). Dexamethasone-linker hydrogel prodrug is then washed with DMF (10 times), dichloromethane (10 times) and ethanol (10 times) and dried in vacuo.

Dexamethasone linker hydrogel prodrugs 10a, 10b, 10c and 10d were synthesized according to general procedure D by using hydrogels 3b, 3b, 3d and 3b respectively, and dexamethasone linker reagent 8a, 8b, 8b and 8c respectively. NMP (90 mg hydrogel/mL NMP) was used instead of DMF for the synthesis of 10c.

Dexamethasone loading was calculated based on hydrogel weight increase after conjugation. A dexamethasone loading of 14-17% (weight dexamethasone/total weight of dexamethasone linker hydrogel) was obtained

Example 13

In Vitro Release Kinetics

In Vitro Release Kinetics at pH 7.40:

Dexamethasone linker hydrogel prodrug aliquots were weighed into a syringe equipped with a polyethylene frit and washed three times with pH 7.40 PBSTE buffer. The syringe was filled up to ca. 2 mL with the same buffer and incubated at 37° C. At defined time points (after 1-7 days incubation time each) the supernatant was exchanged and released dexamethasone was quantified by RP-HPLC at 215 nm. UV-signals correlating to liberated dexamethasone were integrated and amount of released dexamethasone was calculated by comparison with a dexamethasone calibration curve. Liberated dexamethasone was plotted against incubation time and half life of release was determined using curve-fitting software assuming first-order release kinetics.

Release half life time of dexamethasone from dexamethasone linker hydrogel prodrugs:

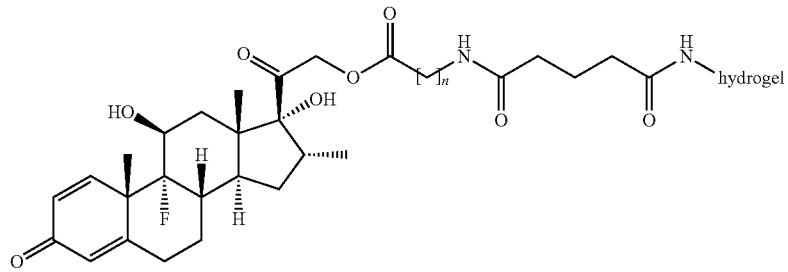

10a: n = 1, hydrogel 3b
10b: n = 2, hydrogel 3b
10c: n = 2, hydrogel 3d
10d: n = 3, hydrogel 3b

| Compound pH 7.40 | |
|---|---|
| 9a | 4.8 d |
| 9b | 300 d |
| 9c | 1.6 d |
| 10a | 7.6 d |
| 10b | 46 d |
| 10c | 49 d |
| 10d | 101 d |

Example 14

Pharmacokinetics and Pharmacodynamics of Dexamethasone after Intra-Articular Injection of Dexamethasone-Linker Hydrogel in ACLT-Induced Arthritic Rabbits Arthritis was induced in female *Hyla* NG rabbits (24 weeks old, average weight 4.4 kg) by anterior cruciate ligament transection (ACLT) of the right knee. Four days after surgery animals were injected intraarticularly with dexamethasone linker hydrogel prodrug 10c (4.6 mg dexamethasone content) in 350 µl citrate buffer pH 6.5 or with 350 µl citrate buffer alone. At time points blood was withdrawn and dexamethasone plasma concentration was determined as described in Materials and Methods. Eight weeks after injection, animals were sacrificed. The severity of macroscopic changes on cartilage of the right knee were graded by India Ink uptake. Intact cartilage shows no ink uptake, while increasing damage of cartilage correlates with increasing uptake of ink. In the dexamethasone group, the evaluable animals showed less signs of cartilage degradation compared to the control group. Furthermore hardly any signs of osteophyte formation was observed in dexamethasone group in contrast to the control group, which showed clear and intense formation of osteophytes. PK data show a burstless and steady dexamethasone release profile over eight weeks (FIG. 1).

Example 15

Synthesis of Linker Reagent 11c

Linker reagent 11c was synthesized according to the following scheme:

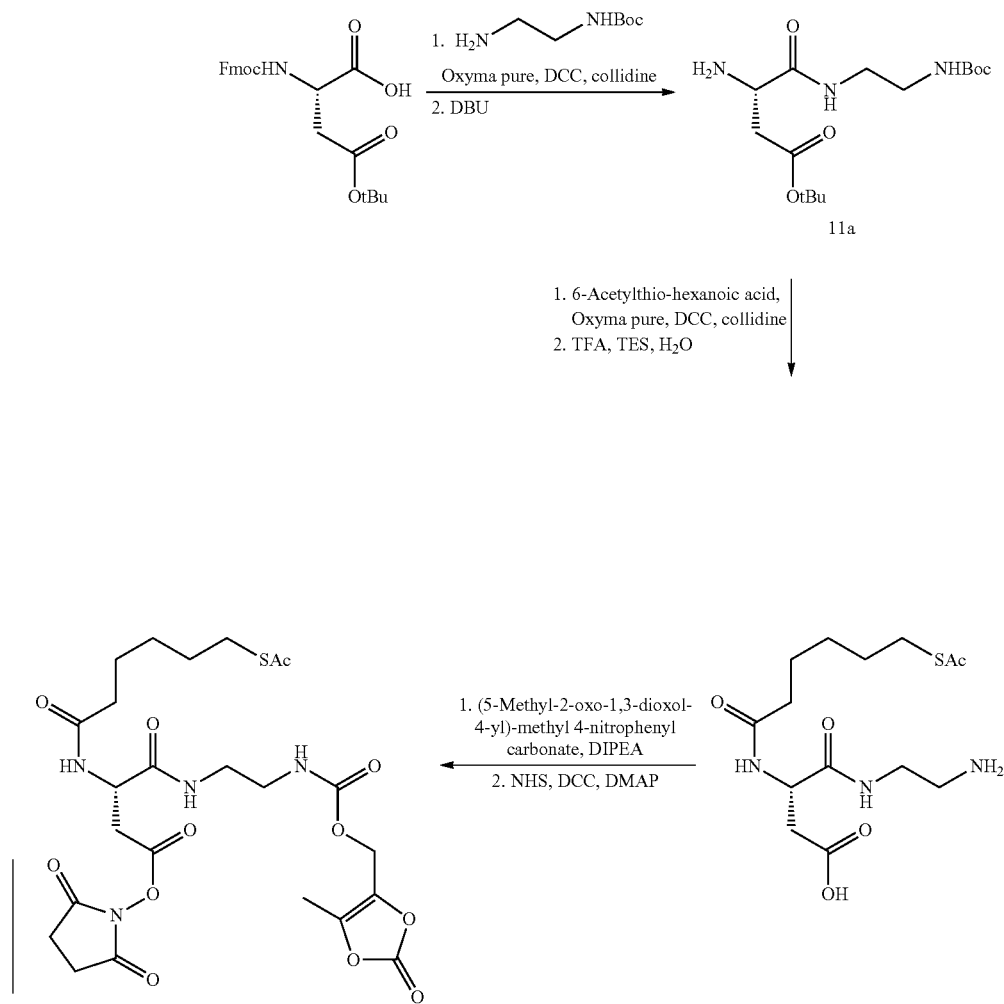

Synthesis of 11a

Fmoc-L-Asp(OtBu)-OH (1.00 g, 2.43 mmol) was dissolved with DCC (0.70 g, 3.33 mmol) in DCM (25 mL). Oxyma pure (0.51 g, 3.58 mmol) and collidine (0.50 mL, 3.58 mmol) were added in one portion and a solution of N-Boc-ethylenediamine (0.41 g, 2.56 mmol) in DCM (15 mL) was added slowly. After stirring the mixture for 90 min at RT the formed precipitate was filtered off and the filtrate washed with aqueous HCl (0.1 M, 50 mL). The aqueous layer was extracted with DCM (2×20 mL) and the combined organic fractions were washed with sat. aqueous $NaHCO_3$ (3×25 mL) and brine (1×50 mL), dried over $Na_2SO_4$, filtered and concentrated in vacuo. The crude solid was purified by flash chromatography. The intermediate N-boc-N'—(N-fmoc-4-tert.-butyl-L-aspartoyl)-ethylenediamine was obtained as white solid (0.98 g, 1.77 mmol, 73%).

MS: m/z 554.29=[M+H], (calculated=554.29).

N-boc-N'—(N-fmoc-4-tert.-butyl-L-aspartoyl)-ethylenediamine (0.98 g, 1.77 mmol) was dissolved in THF (15 mL), DBU (0.31 mL) was added and the solution was stirred for 12 min at RT. The reaction was quenched with AcOH (0.5 ml), concentrated in vacuo and the residue purified by flash chromatography to give 11a (0.61 g, 1.77 mmol, 73% over 2 steps) as white solid.

MS: m/z 332.38=[M+H]$^+$, (calculated=332.22).

Synthesis of 11b

6-Acetylthiohexanoic acid (0.37 g, 1.95 mmol) was dissolved in DCM (19.5 mL) and Oxyma pure (0.35 g, 2.48 mmol) and DCC (0.40 g, 1.95 mmol) added in one portion. The solution was stirred for 30 min at RT, filtered, and the filtrate added to a solution of 11a (0.61 g, 1.77 mmol) in DCM (10.5 mL). DIPEA (0.46 mL, 2.66 mmol) was added to the solution and the reaction stirred for 2 h at RT. The solution was washed with aqueous $H_2SO_4$ (0.1 M, 2×30 mL), sat. aqueous $NaHCO_3$ (2×20 mL) and brine (1×20 mL). The organic layer was dried over $Na_2SO_4$, filtered and concentrated in vacuo. The crude material was purified by flash chromatography to give N-boc-N'—(N-6-acetylthiohexyl-4-tert.-butyl-L-aspartoyl)-ethylenediamine (0.65 g, 1.30 mmol, 73% over 2 steps) as white solid.

MS: m/z 504.27=[M+H]$^+$, (calculated=504.28).

N-boc-N'—(N-6-Acetylthiohexyl-4-tert.-butyl-L-aspartoyl)-ethylenediamine (0.60 g, 1.18 mmol) was dissolved in TFA (5 mL) and TES (0.13 mL) and water (0.13 ml) were added. The mixture was stirred for 30 min at RT. TFA was removed in a stream of $N_2$, and crude 11b dissolved in $H_2O$/ACN 1:1 and purified by RP-HPLC.

Yield: 0.39 g, 0.85 mmol (TFA salt), 72%.

MS: m/z 348.25=[M+H]$^+$, (calculated=348.16).

Synthesis of 11c 11b (TFA salt, 0.38 g, 0.80 mmol) was dissolved in DMF (5 mL) and (5-methyl-2-oxo-1,3-dioxol-4-yl)-methyl 4-nitrophenyl carbonate (0.26 g, 0.88 mmol) and DIPEA (0.28 mL, 1.6 mmol) were added. The resulting suspension was diluted with DCM (5 mL) and stirred for 3 h at RT. More DIPEA (0.28 mL 1.6 mmol) was added and stirring continued for 2 h. DCM was concentrated in vacuo, the residue diluted with $H_2O$/ACN 3:1 and purified by RP-HPLC to give N-(5-methyl-2-oxo-1,3-dioxol-4-yl)-methyl-oxocarbonyl-N'—(N-6-acetylthiohexyl-L-aspartyl)-ethylenediamine (0.31 g, 0.62 mmol, 77%) as colorless oil.

MS: m/z 504.16=[M+H]$^+$, (calculated=504.17).

N-(5-methyl-2-oxo-1,3-dioxol-4-yl)-methyl oxocarbonyl-N'—(N-6-acetylthiohexyl-L-aspartyl)-ethylene-diamine (150 mg, 0.30 mmol) was dissolved in DCM (17.5 mL) and NHS (41 mg, 0.36 mmol), DCC (74 mg, 0.36 mmol) and DMAP (4 mg, 0.03 mmol) were added in one portion. The reaction was stirred for 1 h at RT and the resulting suspension filtered. The precipitate was washed with a small amount of DCM and the combined filtrates concentrated in vacuo. 11c was purified by RP-HPLC to give a colorless oil (144 mg, 0.24 mmol, 80%).

MS: m/z 601.18=[M+H]$^+$, (calculated=601.18).

Example 16

Preparation of Gamma Sterilized Hydrogel Beads 12

A suspension of 523 mg hydrogel beads 3e in 10 mL 1% n-propylamine in NMP was gamma irradiated ($^{60}$Co) with a dose of 30 kGy at room temperature.

Example 17

Preparation of PEGylated hydrogel beads 13a and 13b

A suspension of 523 mg of hydrogel beads 12 in 1% n-propylamine in NMP was washed five times with NMP and five times with DMSO. 189 mg NHS activated carboxy PEG 20 kDa was dissolved in 3 mL DMSO (37° C.) and added to the hydrogel beads. 52 µl TMEDA in 1.5 mL DMSO was added and the mixture was shaken for 48 h at room temperature. Resulting PEGylated hydrogel beads 13a were washed five times each with DMSO and NMP and used in the next reaction without further treatment.

13b was prepared as described for 13a except for the use of 499 mg hydrogel beads 3f, 390 mg NHS activated carboxy PEG 20 kDa and 134 µl of TMEDA.

Example 18

Preparation of Maleimide Functionalized Hydrogel Beads 14a and 14b

Hydrogel beads 13a in NMP were washed two times with 2% DIPEA in NMP. 340 mg of Mal-PEG6-PFP was dissolved in 2 mL NMP and added to the washed hydrogel beads 6a. The hydrogel suspension was incubated for 2 h at room temperature. Resulting maleimide functionalized hydrogel beads 14a were washed five times each with NMP, water, water/ethanol p.a. 1/1 and ethanol p.a. Hydrogel beads 14a were dried at 0.1 mbar to constant weight. A maleimide content of 0.048 mmol/g was obtained.

14b was prepared as described for 14a except for the use of hydrogel beads 13b and 450 mg of Mal-PEG6-PFP. A maleimide content of 0.104 mmol/g was obtained.

Example 19

Synthesis of Deprotected IL-1ra-Linker 15c

Deprotected IL-1ra-linker 15c was synthesized according to the following scheme:

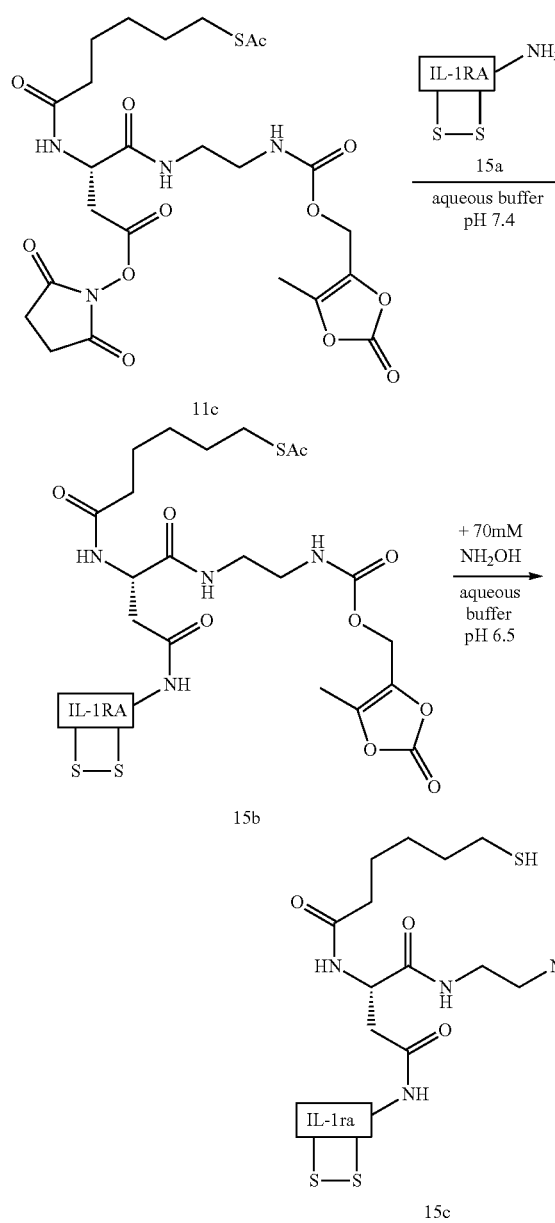

Synthesis of Oxidized IL-1ra 15a 1000 mg IL-1ra (Kineret®, 10 ready to use syringes, 7450 µL solution) was diluted with 30 mL PBSTE buffer. A solution of 57.4 mg 5,5'-Dithiobis(2-nitrobenzoic acid) in 3.54 mL of 0.5 M phosphate buffer pH 7.4 was added. Mixture was incubated for 1 h at room temperature and oxidized IL-1ra 15a (formation of internal disulfide bridge) was buffer exchanged to PBSTE buffer.

MS: m/z 1726.54=[M+10H]$^{10+}$, (calculated=1726.56).

Complete IL-1ra oxidation (formation of internal disulfide bridge) can be confirmed in the maleimide reactivity test. Oxidized IL-1ra 15a lacks maleimide reactivity due to blocking of a reactive cysteine, while IL-1ra shows complete conversion with a maleimide reagent in a 1/1 ratio.

Maleimide readyctivity test: 2 µl IL-1ra solution (23.9 mg/mL) is diluted with 30 and reacted for 10 min with 1.2 solution of 7.5 mg N-Maleoyl-beta-alanine/mL 0.5 M phosphate buffer pH 7.4). As determined by LCMS, IL-pH 7.4 was ra showed complete conversion with the maleimide in a 1/1 ratio, while oxidized IL-1ra 15a lacked reactivity.

MS (IL-1ra+maleimide reagent): m/z 1743.61=[M+10H]$^{10+}$, (calculated=1743.67).

MS (oxidized IL-1ra 15a): m/z 1726.54=[M+10H]$^{10+}$, (calculated=1726.56).

Synthesis of Deprotected IL-1ra-Linker 15c 6 mg of linker reagent 11c was dissolved in 100 µL DMSO to yield a concentration of 100 mM. 115 µl (0.5 molar equivalent of linker reagent 11c relative to the amount of IL-1ra) was added to a solution of IL-1ra 15a in PBSTE buffer (17.98 mg/mL, 22.3 mL). The reaction mixture was mixed carefully and incubated for 5 min at room temperature. Subsequently, 2 additional 0.5 molar equivalents of linker reagent 11c were added and after addition of each equivalent the reaction mixture was incubated for 5 min at room temperature yielding a mixture of IL-1ra 15a and the protected IL-1ra-linker monoconjugate 15b. The ratio of IL-1ra 15a and the protected IL-1ra-linker monoconjugate 15b is approx. 2/1 as determined by MS [M+10H]$^{10+}$. Buffer was exchanged to pH 6.5 citrate buffer. A final volume of 22 mL was obtained.

MS (protected IL-1ra-linker 15b): m/z 1775.05=[M+10H]$^{10+}$, (calculated=1775.07).

To remove the protecting groups from 15b, 0.5 M NH$_2$OH in pH 6.5 citrate buffer (NH$_2$OH Hydrochloride dissolved in pH 6.5 citrate buffer, adjusted to pH 6.50 by adding 4 N NaOH) was added to a final concentration of 70 mM NH$_2$OH to the solution of 15b in 22 mL citrate buffer pH 6.5. The deprotection reaction was incubated at room temperature for 6 h yielding a mixture of deprotected IL-1ra-linker conjugate 15c and IL-1ra 15a. The mixture was concentrated (Centrifugal Filter Units, Amicon Ultra 15, MWCO 10 kDa), buffer exchanged to pH 6.5 citrate buffer and filtered sterile through 0.22 µm syringe filter.

A final volume of 15 mL and an overall protein concentration of 22.06 mg/mL of the different IL-1ra species were obtained. The ratio of IL-1ra 15a and the deprotected IL-1ra-linker conjugate 15c is approx. 2/1 as determined by MS [M+10H]$^{10+}$.

MS (deprotected IL-1ra-linker 15c): m/z 1755.29=[M+10H]$^{10+}$, (calculated=1755.24).

Example 20

Synthesis of IL-1ra-Linker-Hydrogel Prodrug 16a and 16b 33 mg maleimide functionalized hydrogel beads 14a were washed five times with pH 6.5 citrate buffer. 3.4 mL of the IL-1ra 15a/IL-1ra-linker conjugate 15c mixture in pH 6.5 citrate buffer (22.06 mg overall protein content/mL) were added to the hydrogel and shaken overnight at room temperature. Hydrogel was washed 5 times with pH 6.5 citrate buffer. In order to quench residual maleimide groups, a solution of 2.4 µl mercaptoethanol in 3 mL pH 6.5 citrate buffer was added to the hydrogel and shaken for 1 h. Hydrogel was washed five times with pH 6.5 citrate buffer. Reduction of IL-1ra disulfide was performed by washing the hydrogel three times with DTT solution (0.1 M DTT in 90% PBSTE and 10% 0.5 M phosphate buffer pH 7.4, adjusted to pH 7.4). 3 mL DTT solution were drawn to the hydrogel and the suspension was incubated for 1 d at 37° C. Hydrogel was washed twelve times with pH 6.5 citrate buffer. IL-1ra linker hydrogel prodrug 16a was transferred in a tared vial and diluted with pH 6.5 citrate buffer in order to obtain a free flowing suspension.

IL-1RA loading of hydrogel was determined by analyzing aliquots of IL-1ra linker hydrogel prodrug 16a by quantitative amino acid analysis (QAAA).

A loading of 0.67 mg IL1RA/mg hydrogel was obtained.

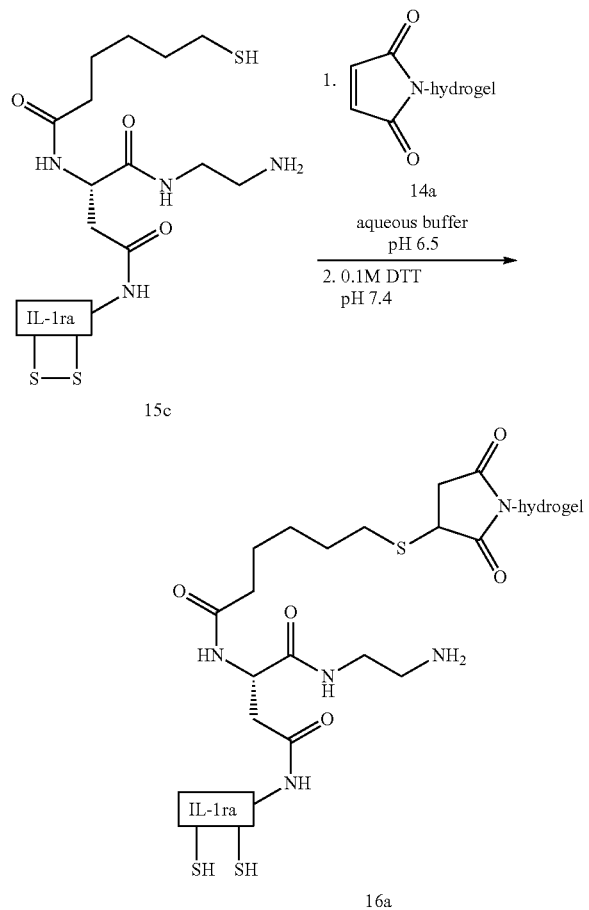

IL-1ra linker hydrogel prodrug 16b was synthesized accordingly except for the use of 11 mg hydrogel beads 14b, 3.5 mL of the IL-1ra 15a/IL-1ra-linker conjugate 15c mixture in pH 6.5 citrate buffer (22.06 mg/mL) and 0.8 µl mercaptoethanol.

A loading of 1.64 mg IL1RA/mg hydrogel was obtained.

Example 21

In Vitro Release Kinetics

Determination of In Vitro Half-Life

Aliquots of IL-1ra-linker-hydrogel prodrug 16a or 16b (containing approximately 5 mg IL-1ra) were washed five times with PBSTE buffer and incubated in ca. 1 mL PBSTE at 37° C. The buffer was exchanged after different time intervals and released IL-1ra was quantified by SEC-HPLC at 220 nm. Peaks corresponding to liberated IL-1ra were integrated and the total amount of liberated IL-1ra was plotted against total incubation time. Curve fitting software (Graphpad Prism 5.04) was applied to determine first-order cleavage rates. A release half life time of 6 weeks was obtained.

Identity of released IL-1ra was confirmed by SEC-HPLC and MS. Released IL-1ra was reactive in the maleimide test (Example 19), thus confirming successful reduction of disulfide bond of oxidized IL-1ra on hydrogel.

Example 22

Chondroprotective Effect of Intra-Articular Injection of IL-1ra Linker Hydrogel Prodrug in ACLT-Induced Arthritic Rabbits Arthritis was induced in 24 weeks old female *Hyla* NG rabbits (average weight 4.4 kg) by anterior cruciate ligament transection (ACLT) of the right knee. Four days after surgery animals were injected intraarticularly with IL-1ra linker hydrogel prodrug 16a (7.5 mg IL-1ra content) in 350 µl citrate buffer pH 6.5 or with 350 µl citrate buffer alone. Eight weeks after injection, animals were sacrificed. The severity of macroscopic changes on cartilage of the right knee were graded by India Ink uptake. Intact cartilage shows no ink uptake, while increasing damage of cartilage correlates with increasing uptake of ink. In the IL-1ra group, the cartilage showed much less signs of degradation compared to the control group. Osteophyte formation on the medial condyle was less intense in the IL-1ra group compared to control group. In contrast to the control group, no signs of osteophyte formation were observed in the tibial plateau of the IL-1ra group.

ABBREVIATIONS

ACLT anterior crutiate ligament transection
AcOH acetic acid
AcOEt ethyl acetate
Bn benzyl
Boc t-butyloxycarbonyl
DBU 1,3-diazabicyclo[5.4.0]undecene
DCC N,N-dicyclohexylcarbodiimid
DCM dichloromethane
DIPEA diisopropylethylamine
DMAP dimethylamino-pyridine
DMF N,N-dimethylformamide
DMSO dimethylsulfoxide
DTT DL dithiotreitol
EDC 1-Ethyl-3-(3-dimethylaminopropyl)carbodiimid
EDTA ethylenediaminetetraacetic acid
eq stoichiometric equivalent
EtOH ethanol
Fmoc 9-fluorenylmethoxycarbonyl
HPLC high performance liquid chromatography
HOBt N-hydroxybenzotriazole
iPrOH 2-propanol
LCMS mass spectrometry-coupled liquid chromatography
Mal 3-maleimido propyl
Mal-PEG6-NHS N-(3-maleimidopropyl)-21-amino-4,7,10,13,16,19-hexaoxa-heneicosanoic acid NHS ester
Me methyl
MeOH methanol Mmt 4-methoxytrityl
MS mass spectrum/mass spectrometry
MTBE methyl tert. -butyl ether
MW molecular mass
NHS N-hydroxy succinimide
PBSTE Phosphate buffered saline with Tween and EDTA
PEG poly(ethylene glycol)
PyBOP benzotriazole-1-yl-oxy-tris-pyrrolidino-phosphonium hexafluorophosphate
RP-HPLC reversed-phase high performance liquid chromatography
rpm rounds per minute
RT room temperature
SEC size exclusion chromatography
TCEP tris(2-carboxyethyl)phosphine hydrochloride
TES triethylsilane
TFA trifluoroacetic acid
THF tetrahydrofurane
TMEDA N,N,N'N'-tetramethylethylene diamine
Trt triphenylmethyl, trityl
UPLC ultra performance liquid chromatography
v volume

The invention claimed is:
1. A method of administering a biologically active moiety to a subject in need of treatment of a disease of the joint, the method comprising:
  administering a polymeric prodrug via intra-articular injection;
  wherein the polymeric prodrug comprises, as a polymeric carrier, a water-insoluble hydrogel to which at least one biologically active moiety is covalently conjugated through a reversible prodrug linker moiety;
  wherein, upon cleavage of said reversible prodrug linker moiety, the biologically active moiety is released as the corresponding drug in its free form;
  wherein the at least one biologically active moiety is selected from the group consisting of (i) non-steroidal anti-inflammatory drugs (NSAIDs), (ii) disease modifying anti rheumatic drugs (DMARDs), (iii) corticosteroids, and (iv) antibodies and fragments thereof, fusion proteins, binding proteins, peptides and recombinant proteins;
  wherein the reversible prodrug linker moiety is of formula (VII):

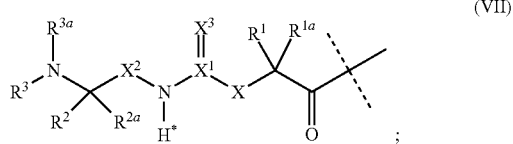

(VII)

wherein the dashed line indicates the attachment to a primary or secondary amino group of an amine-containing biologically active moiety D by forming an amide bond; and
  wherein X, $X^1$, $X^2$, $X^3$, $R^1$, $R^{1a}$, $R^2$, $R^{2a}$, $R^3$, and $R^{3a}$ of formula (VII) have the following meaning:
    X is $C(R^4R^{4a})$, $N(R^4)$, O, $C(R^4R^{4a})$—$C(R^5R^{5a})$, $C(R^5R^{5a})$—$C(R^4R^{4a})$, $C(R^4R^{4a})$—$N(R^6)$, $N(R^6)$—$C(R^4R^{4a})$, $C(R^4R^{4a})$—O, or O—$C(R^4R^{4a})$;
    $X^1$ is C or S(O);
    $X^2$ is $C(R^7R^{7a})$ or $C(R^7R^{7a})$—$C(R^8R^{8a})$;
    $X^3$ is O, S, or N—CN;
    $R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, and $R^{8a}$ are independently selected from the group consisting of H and $C_{1-4}$ alkyl; or
    optionally, one or more of the pairs $R^{1a}/R^{4a}$, $R^{1a}/R^{5a}$, $R^{4a}/R^{5a}$, and $R^{7a}/R^{8a}$ form a chemical bond;
    optionally, one or more of the pairs $R^1/R^{1a}$, $R^2/R^{2a}$, $R^4/R^{4a}$, $R^5/R^{5a}$, $R^7/R^{7a}$, and $R^8/R^{8a}$ are joined together with the atom to which they are attached to form a $C_{3-7}$ cycloalkyl; or 4-membered to 7-membered heterocyclyl;
    optionally, one or more of the pairs $R^1/R^4$, $R^1/R^5$, $R^1/R^6$, $R^4/R^5$, $R^7/R^8$, and $R^2/R^3$ are joined together with the atoms to which they are attached to form a ring A;
    optionally, $R^3/R^{3a}$ are joined together with the nitrogen atom to which they are attached to form a 4-membered to 7-membered heterocycle;
    A is selected from the group consisting of phenyl, naphthyl, indenyl, indanyl, tetralinyl, $C_{3-10}$ cycloalkyl, 4-membered to 7-membered heterocyclyl, and 9-membered to 11-membered heterobicyclyl;
  wherein the reversible prodrug linker moiety of formula (VII) is connected to one group $L^2$-Z and optionally more groups $L^2$-Z, provided that the hydrogen marked with the asterisk in formula (VII) is not replaced by $L^2$-Z; and
  wherein:
    $L^2$ is a single chemical bond or a spacer; and
    Z is the water-insoluble hydrogel.

2. The method of claim 1;
wherein when the reversible prodrug linker moiety of formula (VII) is connected to $L^2$-Z at $R^3$ or $R^{3a}$, $R^3$ and $R^{3a}$ independently are H or are connected to N through an $SP^3$-hybridized carbon atom.

3. The method of claim 1;
wherein the polymeric carrier comprises a PEG-based hydrogel.

4. The method of claim 1;
wherein the water-insoluble hydrogel is a hyaluronic acid-based hydrogel.

5. The method of claim 1;
wherein the water-insoluble hydrogel is polymerized through radical polymerization, ionic polymerization, or ligation reaction.

6. The method of claim 1;
wherein the at least one biologically active moiety comprises IL-1ra.

7. The method of claim 1;
wherein the at least one biologically active moiety is selected from the group consisting of non-steroidal anti-inflammatory drugs (NSAIDs), fenamic acid derivatives, biphenylcarboxylic acid derivatives, oxicams, methotrexate, cyclooxygenase-2 (COX-2) inhibitors, anti-tumor necrosis factor (TNF) agents, anti-IL-1 agents, anti-IL-6 agents, anti-IL-12 agents, anti-IL-15 agents, anti-IL-18 agents, anti-IL-21 agents, anti-IL-23 agents, fasinumab, tanezumab, anti-nerve growth factor (NGF) antibodies and antibody derivatives, anti-nerve growth factor receptor (NGFR) antibodies and antibody derivatives, TrkA antagonists, glucocorticoids, leflunomide, D-penicillamine, sulfasalazine, chloroquine derivatives, anti-CD20 antibodies, RANKL inhibitors, growth hormone, bone morphogenetic proteins, fibroblast growth factors, transforming growth factor-β, insulin-like growth factor, vascular endothelial growth factor, platelet-derived growth factor, growth/differentiation factor 5, NELL peptides, LIM mineralization proteins, matrix metalloproteinases, aggrecanases, cysteine-dependent cathepsins, and cell adhesion molecules (CAMs).

8. The method of claim 1;
wherein the polymeric prodrug is in the form of microparticles.

9. The method of claim 1;
wherein the polymeric prodrug is comprised in a pharmaceutical composition, the pharmaceutical composition further comprising one or more pharmaceutically acceptable excipients.

10. The method of claim 9;
wherein the pharmaceutical composition additionally comprises at least one other biologically active moiety, either in its free form or as a prodrug.

11. The method of claim 1;
wherein the disease of the joint is selected from the group consisting of infectious arthropathies (M00 to M03) (codes of International Classification of Disease).

12. The method of claim 1;
wherein the disease of the joint is selected from the group consisting of osteoarthritis, rheumatoid arthritis, Achilles tendinitis, acromegalic arthropathy, ankylosing spondylitis, bursitis, crystal deposition disease, chronic synovitis, chronic recurrent multifocal osteomyelitis, degenerative joint disease, diabetic finger sclerosis, discitis, discoid lupus erythematosus, drug-induced lupus, epicondylitis, Farber's lipogranulomatosis, Felty's syndrome, foreign body synovitis, Freiberg's disease, fungal arthritis, gonococcal arthritis, Goodpasture's syndrome, gout, granulomatous arteritis, hemarthrosis, hemochromatosis, Henoch-Schonlein purpura, hip dysplasia, hypertrophic osteoarthropathy, impingement syndrome, Jaccoud's arthropathy, juvenile ankylosing spondylitis, Lyme disease, malignant synovioma, medial plica syndrome, metastatic carcinomatous arthritis, multiple epiphyseal dysplasia, olecranon bursitis, Osgood-Schlatter's disease, osteomyelitis, palindromic rheumatism, patellofemoral pain syndrome, pigmented villonodular synovitis, popliteal cysts, posterior tibial tendonitis, Pott's disease, prepatellar bursitis, prosthetic joint infection, psoriatic arthritis, reactive arthritis/Reiter's syndrome, retrocalcaneal bursitis, rheumatoid vasculitis, rotator cuff tendonitis, *Salmonella* osteomyelitis, saturnine gout, septic arthritis, sickle cell arthropathy, spinal stenosis, tennis elbow, Tietse's syndrome, and trochanteric bursitis.

13. The method of claim 1;
wherein the disease of the joint is arthritis.

14. The method of claim 1;
wherein the disease of the joint is selected from osteoarthritis and rheumatoid arthritis.

15. The method of claim 1;
wherein the disease of the joint is selected from the group consisting of erosive inflammatory osteoarthritis, juvenile rheumatoid arthritis, seronegative arthritis, *Shigella* arthritis, *Staphylococcus* arthritis, syphilitic arthritis, traumatic arthritis, tuberculosis arthritis, arthritis of ulcerative colitis, viral arthritis, and *Yersinia* arthritis.

* * * * *